(12) United States Patent
Fanson et al.

(10) Patent No.: US 11,865,008 B2
(45) Date of Patent: *Jan. 9, 2024

(54) METHOD AND SYSTEM FOR DETERMINING A RELATIVE POSITION OF A TOOL

(71) Applicant: INTELLIJOINT SURGICAL INC., Kitchener (CA)

(72) Inventors: Richard Tyler Fanson, Stoney Creek (CA); Andre Novomir Hladio, WATERLOO (CA); Armen Garo Bakirtzian, Kitchener (CA)

(73) Assignee: Intellijoint Surgical Inc., Kitchener (CA)

( * ) Notice: Subject to any disclaimer, the term of this patent is extended or adjusted under 35 U.S.C. 154(b) by 0 days.

This patent is subject to a terminal disclaimer.

(21) Appl. No.: 18/111,235

(22) Filed: Feb. 17, 2023

(65) Prior Publication Data
US 2023/0200997 A1  Jun. 29, 2023

Related U.S. Application Data

(63) Continuation of application No. 17/558,151, filed on Dec. 21, 2021, which is a continuation of application
(Continued)

(51) Int. Cl.
*A61B 5/00* (2006.01)
*A61F 2/32* (2006.01)
(Continued)

(52) U.S. Cl.
CPC ............... *A61F 2/32* (2013.01); *A61B 34/20* (2016.02); *A61B 34/25* (2016.02); *A61B 90/39* (2016.02);
(Continued)

(58) Field of Classification Search
CPC . A61F 2/32; A61F 2/46; A61F 2/4609; A61B 34/20; A61B 34/25; A61B 90/39;
(Continued)

(56) References Cited

U.S. PATENT DOCUMENTS 4,994,064 A 2/1991 Aboczky
5,122,145 A 6/1992 Fishbane
(Continued)

FOREIGN PATENT DOCUMENTS

EP 1563810 B1 3/2010
FR 2684287 A 6/1993
(Continued)

OTHER PUBLICATIONS

Birrell et al, "Projecting the need for hip replacement over the next three decades: influence of changing demography and threshold for surgery," Annals of the Rheumatic Diseases, vol. 58, pp. 569-572 (1999).
(Continued)

*Primary Examiner* — May A Abouelela

(57) ABSTRACT

Presented are methods and systems for determining, monitoring, and displaying the relative positioning of two rigid bodies such as during a surgery. In particular, the present disclosure relates to methods and systems for positioning a prosthesis relative to a bone during a surgery as well as to systems and methods for verifying resulting relative positioning of adjacent bones.

30 Claims, 31 Drawing Sheets

Related U.S. Application Data

No. 16/180,517, filed on Nov. 5, 2018, now Pat. No. 11,229,520, which is a continuation of application No. 14/799,909, filed on Jul. 15, 2015, now Pat. No. 10,117,748, which is a continuation of application No. 13/328,997, filed on Dec. 16, 2011, now Pat. No. 9,138,319.

(60) Provisional application No. 61/424,447, filed on Dec. 17, 2010.

(51) Int. Cl.
| | |
|---|---|
| *A61F 2/46* | (2006.01) |
| *A61B 34/20* | (2016.01) |
| *A61B 34/00* | (2016.01) |
| *A61B 90/00* | (2016.01) |
| *A61B 17/17* | (2006.01) |
| *A61B 5/11* | (2006.01) |
| *A61B 6/03* | (2006.01) |
| *A61B 34/10* | (2016.01) |

(52) U.S. Cl.
CPC ............. *A61F 2/46* (2013.01); *A61B 5/0077* (2013.01); *A61B 5/11* (2013.01); *A61B 5/1114* (2013.01); *A61B 5/1127* (2013.01); *A61B 5/4528* (2013.01); *A61B 6/032* (2013.01); *A61B 17/17* (2013.01); *A61B 17/1703* (2013.01); *A61B 17/1746* (2013.01); *A61B 17/1764* (2013.01); *A61B 34/10* (2016.02); *A61B 90/37* (2016.02); *A61B 2034/107* (2016.02); *A61B 2034/2048* (2016.02); *A61B 2034/2055* (2016.02); *A61B 2034/2057* (2016.02); *A61B 2034/2065* (2016.02); *A61B 2034/2068* (2016.02); *A61B 2090/3945* (2016.02); *A61B 2090/3983* (2016.02); *A61F 2/4609* (2013.01)

(58) Field of Classification Search
CPC ....... A61B 5/0077; A61B 5/11; A61B 5/1114; A61B 5/1127; A61B 5/4528; A61B 6/032; A61B 17/17; A61B 17/1703; A61B 17/1746; A61B 17/1764; A61B 34/10; A61B 90/37; A61B 2034/107; A61B 2034/2048; A61B 2034/2055; A61B 2034/2057; A61B 2034/2065; A61B 2034/2068; A61B 2090/3945; A61B 2090/3983

See application file for complete search history.

(56) References Cited

U.S. PATENT DOCUMENTS

| | | | |
|---|---|---|---|
| 5,141,512 A | | 8/1992 | Farmer et al. |
| 5,227,985 A | * | 7/1993 | DeMenthon ............ G01S 5/163 |
| | | | 345/158 |
| 5,249,581 A | * | 10/1993 | Horbal ................. A61B 5/1077 |
| | | | 600/595 |
| 5,480,439 A | | 1/1996 | Bisek et al. |
| 5,611,353 A | | 3/1997 | Dance et al. |
| 5,700,268 A | | 12/1997 | Bertin |
| 5,772,610 A | | 6/1998 | McGorry et al. |
| 5,807,252 A | | 9/1998 | Hassfeld et al. |
| 5,854,843 A | | 12/1998 | Jacknin et al. |
| 5,880,976 A | | 3/1999 | DiGioia, III et al. |
| 5,956,660 A | | 9/1999 | Neumann |
| 5,966,827 A | | 10/1999 | Horvath et al. |
| 6,009,189 A | * | 12/1999 | Schaack ................. A61B 5/065 |
| | | | 348/42 |
| 6,061,644 A | | 5/2000 | Leis |
| 6,161,032 A | | 12/2000 | Acker |
| 6,395,005 B1 | | 5/2002 | Lovell |
| 6,450,978 B1 | | 9/2002 | Brosseau et al. |
| 6,529,765 B1 | | 3/2003 | Franck et al. |
| 6,607,487 B2 | | 8/2003 | Chang et al. |
| 6,711,431 B2 | | 3/2004 | Sarin et al. |
| 6,917,827 B2 | | 7/2005 | Kienzle, III |
| 6,925,339 B2 | | 8/2005 | Grimm et al. |
| 6,978,167 B2 | | 12/2005 | Dekel et al. |
| 6,988,009 B2 | | 1/2006 | Grimm et al. |
| 7,001,346 B2 | * | 2/2006 | White .................... A61B 90/06 |
| | | | 600/587 |
| 7,130,676 B2 | * | 10/2006 | Barrick .................. A61B 90/36 |
| | | | 606/130 |
| 7,302,355 B2 | | 11/2007 | Jansen et al. |
| 7,314,048 B2 | | 1/2008 | Couture et al. |
| 7,392,076 B2 | | 6/2008 | Moctezuma de La Barrera |
| 7,400,246 B2 | | 7/2008 | Breeding |
| 7,407,054 B2 | | 8/2008 | Seiler et al. |
| 7,412,777 B2 | | 8/2008 | Pelletier et al. |
| 7,419,492 B2 | | 9/2008 | Yoon et al. |
| 7,427,272 B2 | | 9/2008 | Richard et al. |
| 7,431,736 B2 | | 10/2008 | Maroney et al. |
| 7,559,931 B2 | | 7/2009 | Stone |
| 7,588,571 B2 | | 9/2009 | Olsen |
| 7,594,933 B2 | | 9/2009 | Kammerzell et al. |
| 7,611,520 B2 | * | 11/2009 | Broers ................. A61B 5/1079 |
| | | | 606/88 |
| 7,634,306 B2 | | 12/2009 | Sarin et al. |
| 7,657,298 B2 | * | 2/2010 | Moctezuma de la Barrera .......... |
| | | | A61B 34/20 |
| | | | 600/407 |
| 7,668,584 B2 | | 2/2010 | Jansen |
| 7,769,429 B2 | | 6/2010 | Hu |
| 7,753,921 B2 | | 7/2010 | Leitner |
| 7,780,681 B2 | | 8/2010 | Sarin et al. |
| 7,840,256 B2 | * | 11/2010 | Lakin ..................... A61B 90/39 |
| | | | 600/421 |
| 7,876,942 B2 | | 1/2011 | Gilboa |
| 7,877,131 B2 | | 1/2011 | Jansen et al. |
| 7,885,705 B2 | | 2/2011 | Murphy |
| 7,927,338 B2 | | 4/2011 | Laffargue et al. |
| 7,970,190 B2 | | 6/2011 | Steinle et al. |
| 7,995,280 B2 | | 8/2011 | Kuss et al. |
| 8,000,926 B2 | | 8/2011 | Roche et al. |
| 8,007,448 B2 | | 8/2011 | Moctezuma de La Barrera |
| 8,034,057 B2 | | 10/2011 | Penenberg |
| 8,152,726 B2 | | 4/2012 | Amiot et al. |
| 8,165,659 B2 | * | 4/2012 | Sheffer .................. A61B 34/20 |
| | | | 600/407 |
| 8,167,823 B2 | | 5/2012 | Nycz et al. |
| 8,177,850 B2 | | 5/2012 | Rudan et al. |
| 8,202,324 B2 | | 6/2012 | Meulink et al. |
| 8,206,405 B2 | | 6/2012 | Beverland et al. |
| 8,231,554 B2 | * | 7/2012 | Tuma ................... A61F 2/4657 |
| | | | 600/595 |
| 8,308,663 B2 | | 11/2012 | Tuma et al. |
| 8,337,426 B2 | | 12/2012 | Nycz |
| 8,400,312 B2 | | 3/2013 | Hotokebuchi et al. |
| 8,425,557 B2 | | 4/2013 | Kuiper et al. |
| 8,467,851 B2 | * | 6/2013 | Mire ..................... A61B 90/39 |
| | | | 600/407 |
| 8,482,606 B2 | * | 7/2013 | Razzaque ............... A61B 1/042 |
| | | | 348/77 |
| 8,554,307 B2 | * | 10/2013 | Razzaque ............... A61B 8/483 |
| | | | 600/407 |
| 8,585,598 B2 | * | 11/2013 | Razzaque ............... A61B 90/39 |
| | | | 600/439 |
| 8,641,621 B2 | * | 2/2014 | Razzaque .......... A61B 18/1477 |
| | | | 600/407 |
| 8,657,809 B2 | | 2/2014 | Schoepp |
| 8,670,816 B2 | * | 3/2014 | Green .................. A61B 17/221 |
| | | | 600/424 |
| 8,690,776 B2 | * | 4/2014 | Razzaque ............... A61B 34/20 |
| | | | 600/407 |
| 2002/0077540 A1 | * | 6/2002 | Kienzle, III ........ A61B 17/1703 |
| | | | 606/130 |
| 2002/0087101 A1 | | 7/2002 | Barrick et al. |
| 2002/0198451 A1 | | 12/2002 | Carson |

(56) References Cited

U.S. PATENT DOCUMENTS

| | | |
|---|---|---|
| 2003/0069591 A1 | 4/2003 | Carson et al. |
| 2003/0105470 A1 | 6/2003 | White |
| 2003/0153978 A1* | 8/2003 | Whiteside .............. A61B 34/20 73/172 |
| 2003/0163142 A1* | 8/2003 | Paltieli .................. A61B 34/20 606/130 |
| 2003/0208296 A1 | 11/2003 | Brisson et al. |
| 2004/0102792 A1 | 5/2004 | Sarin et al. |
| 2004/0106861 A1* | 6/2004 | Leitner ................ A61B 5/4528 600/407 |
| 2004/0143340 A1* | 7/2004 | Tuma .................... A61B 34/20 623/914 |
| 2004/0147926 A1 | 7/2004 | Iversen |
| 2004/0254586 A1 | 12/2004 | Sarin et al. |
| 2005/0015002 A1 | 1/2005 | Dixon et al. |
| 2005/0021044 A1 | 1/2005 | Stone et al. |
| 2005/0049524 A1* | 3/2005 | Lefevre .................... A61F 2/46 600/595 |
| 2005/0065617 A1* | 3/2005 | Moctezuma de la Barrera .......... A61B 5/4528 623/908 |
| 2005/0149050 A1 | 7/2005 | Stifter et al. |
| 2005/0245820 A1 | 11/2005 | Sarin |
| 2005/0251026 A1 | 11/2005 | Stone |
| 2005/0288609 A1 | 12/2005 | Warner et al. |
| 2006/0004284 A1 | 1/2006 | Grunschlager et al. |
| 2006/0036324 A1* | 2/2006 | Sachs ................. A61B 17/7064 623/17.11 |
| 2006/0084889 A1 | 4/2006 | Drumm et al. |
| 2006/0089657 A1* | 4/2006 | Broers .................. A61B 5/103 600/595 |
| 2006/0095047 A1 | 5/2006 | de la Barrera |
| 2006/0100508 A1* | 5/2006 | Morrison ............. A61B 5/0064 600/414 |
| 2006/0142657 A1* | 6/2006 | Quaid .................... A61B 90/37 600/424 |
| 2006/0155382 A1 | 7/2006 | Katzman |
| 2006/0161052 A1* | 7/2006 | Colombet .............. A61B 34/10 600/300 |
| 2006/0189864 A1* | 8/2006 | Paradis .................. A61B 90/36 600/407 |
| 2006/0190011 A1 | 8/2006 | Ries |
| 2006/0293614 A1 | 12/2006 | Radinsky et al. |
| 2007/0118139 A1 | 5/2007 | Cuellar et al. |
| 2007/0179568 A1 | 8/2007 | Nycz et al. |
| 2007/0225731 A1 | 9/2007 | Couture et al. |
| 2007/0239281 A1 | 10/2007 | Gotte et al. |
| 2007/0270686 A1 | 11/2007 | Ritter et al. |
| 2008/0027312 A1 | 1/2008 | Dick |
| 2008/0033442 A1 | 2/2008 | Amiot et al. |
| 2008/0077004 A1* | 3/2008 | Henning ................ A61B 90/39 60/426 |
| 2008/0125785 A1 | 5/2008 | Chana |
| 2008/0132783 A1 | 6/2008 | Revie et al. |
| 2008/0146969 A1 | 6/2008 | Kurtz |
| 2008/0172055 A1 | 7/2008 | Mollard et al. |
| 2008/0194997 A1* | 8/2008 | Zhang .................. A61B 5/1071 600/595 |
| 2008/0195109 A1 | 8/2008 | Hunter et al. |
| 2008/0214960 A1 | 9/2008 | Hodgson et al. |
| 2008/0228188 A1 | 9/2008 | Birkbeck et al. |
| 2008/0249394 A1* | 10/2008 | Giori .................... A61B 5/4528 600/407 |
| 2008/0255584 A1 | 10/2008 | Beverland et al. |
| 2008/0269596 A1 | 10/2008 | Revie et al. |
| 2008/0294265 A1 | 11/2008 | Warkentine et al. |
| 2008/0312529 A1 | 12/2008 | Amiot et al. |
| 2008/0319313 A1* | 12/2008 | Boivin .................. A61B 34/20 600/424 |
| 2009/0068620 A1 | 3/2009 | Knobel et al. |
| 2009/0087050 A1* | 4/2009 | Gandyra ............. G01B 11/2545 382/128 |
| 2009/0099570 A1 | 4/2009 | Paradis et al. |
| 2009/0105714 A1 | 4/2009 | Kozak |
| 2009/0125117 A1 | 5/2009 | Paradis et al. |
| 2009/0143670 A1 | 6/2009 | Daigneault et al. |
| 2009/0163930 A1* | 6/2009 | Aoude .................. A61B 34/20 606/130 |
| 2009/0171370 A1 | 7/2009 | Yoon et al. |
| 2009/0209343 A1 | 8/2009 | Foxlin et al. |
| 2009/0209884 A1* | 8/2009 | Van Vorhis ............ G16H 50/50 600/595 |
| 2009/0248044 A1 | 10/2009 | Amiot et al. |
| 2009/0281545 A1 | 11/2009 | Stubbs |
| 2009/0289806 A1 | 11/2009 | Thornberry |
| 2009/0306499 A1* | 12/2009 | Van Vorhis ............ A61B 34/20 606/130 |
| 2009/0314925 A1 | 12/2009 | Van Vorhis et al. |
| 2009/0316967 A1 | 12/2009 | Dardenne et al. |
| 2010/0016705 A1 | 1/2010 | Stone |
| 2010/0063419 A1* | 3/2010 | Mostafavi ............. A61B 5/1135 600/587 |
| 2010/0069911 A1 | 3/2010 | Borja et al. |
| 2010/0076505 A1* | 3/2010 | Borja .................... A61B 5/1077 606/86 R |
| 2010/0100011 A1* | 4/2010 | Roche .................. A61B 5/4528 623/20.14 |
| 2010/0137869 A1* | 6/2010 | Borja .................... A61B 17/154 606/88 |
| 2010/0137871 A1 | 6/2010 | Borja |
| 2010/0153081 A1 | 6/2010 | Bellettre et al. |
| 2010/0191100 A1* | 7/2010 | Anderson ................ G06T 7/246 600/424 |
| 2010/0192961 A1 | 8/2010 | Amiot et al. |
| 2010/0261998 A1 | 10/2010 | Stiehl |
| 2010/0268067 A1* | 10/2010 | Razzaque ............. A61B 8/4245 600/424 |
| 2010/0299101 A1 | 11/2010 | Shimada et al. |
| 2010/0312247 A1* | 12/2010 | Tuma .................... A61B 17/175 606/89 |
| 2011/0004224 A1* | 1/2011 | Daigneault ............. A61B 34/20 606/130 |
| 2011/0092858 A1 | 4/2011 | Burger et al. |
| 2011/0160583 A1* | 6/2011 | Roche .................... A61B 34/20 606/88 |
| 2011/0190637 A1 | 8/2011 | Knobel et al. |
| 2011/0213379 A1 | 9/2011 | Blau et al. |
| 2011/0257653 A1* | 10/2011 | Hughes .................. A61B 34/20 606/86 R |
| 2011/0264009 A1* | 10/2011 | Walter .................. A61F 2/4657 600/595 |
| 2011/0275957 A1* | 11/2011 | Bhandari .............. A61B 5/1114 600/595 |
| 2012/0022406 A1 | 1/2012 | Hladio et al. |
| 2012/0029389 A1* | 2/2012 | Amiot .................... A61B 34/20 600/595 |
| 2012/0053594 A1* | 3/2012 | Pelletier ................ A61B 17/157 606/86 R |
| 2012/0065926 A1 | 3/2012 | Lee et al. |
| 2012/0143084 A1 | 6/2012 | Shoham |
| 2012/0157887 A1 | 6/2012 | Fanson et al. |
| 2012/0209117 A1 | 8/2012 | Mozes et al. |
| 2012/0232802 A1 | 9/2012 | Haimerl et al. |
| 2012/0283599 A1 | 11/2012 | Borja |
| 2013/0030250 A1 | 1/2013 | Findeisen et al. |
| 2013/0116574 A1 | 5/2013 | Knobel et al. |
| 2014/0135658 A1* | 5/2014 | Hladio .................. A61F 2/4609 600/595 |
| 2019/0290378 A1 | 9/2019 | Schwägli et al. |
| 2021/0038276 A1 | 2/2021 | Schwägli et al. |

FOREIGN PATENT DOCUMENTS

| | | |
|---|---|---|
| FR | 2977164 A1 | 2/2012 |
| WO | 2006109983 A | 10/2006 |
| WO | 2006128301 | 12/2006 |
| WO | 2007084893 | 7/2007 |
| WO | 2007095248 A2 | 8/2007 |
| WO | 2008151446 | 12/2008 |
| WO | 2009062314 | 5/2009 |

(56) References Cited

FOREIGN PATENT DOCUMENTS

| WO | 2009117833 | | 10/2009 |
|---|---|---|---|
| WO | 2010030809 | A1 | 3/2010 |
| WO | 2010063117 | A1 | 6/2010 |
| WO | 2012080840 | | 6/2012 |
| WO | 2012080840 | A1 | 6/2012 |
| WO | 2014057352 | A1 | 4/2014 |

OTHER PUBLICATIONS

Seidel et al, "Hip joint center location from palpable bony landmarks—a cadaver study," Journal of Biomechanics, vol. 28, No. 8, pp. 995-998 (1995).

Digioia III et al, "Comparison of a Mechanical Acetabular Alignment Guide With Computer Placement of the Socket," The Journal of Arthroplasty, vol. 17, No. 3, pp. 359-363 (2002).

Digioia III et al, "Surgical Navigation for Total Hip Replacement With the Use of HIPNAV," Operative Techniques in Orthopaedics, vol. 10, No. 1, pp. 3-8 (2000).

Nogler, Michael, et al., "Reduced variability in cup positioning: the direct anteror surgical approach using navigation", Nov. 6, 2009, Informa Healthcare, Acta Orthapaedica, 79:6, 789-793.

Kanoh et al, "Accurate Acetabular Component Orientation After Total Hip Arthroplasty Using an Acetabular Alignment Guide," The Journal of Arthroplasty, vol. 00, No. 0, pp. 1-6 (2009).

International Preliminary Report on Patentability dated Jun. 7, 2011, relating to PCT International Patent Application No. PCT/CA2009/001765 issued from the International Bureau of WIPO.

Written Opinion of the International Search Authority dated Feb. 18, 2010, relating to PCT International Patent Application No. PCT/CA2009/001765 issued from the Canadian Intellectual Property Office.

Toshiya Kanoh, MD, et al., "Accurate Acetabular Component Orientation After Total Hip Arthroplasty Using an Acetabular Alignment Guide", The Journal of Arthroplasty, vol. 25, No. 1, 2010, p. 81-85.

Solomon et al, "Surgical Anatomy for Pelvic External Fixation," Clinical Anatomy, vol. 21, pp. 674-682 (2008).

International Search Report dated Feb. 18, 2010 in International Application No. PCT/CA2009/001765.

International Search Report issued by the Canadian Intellectual Property Office for International PCT Patent Application No. PCT/IB2011/003246.

* cited by examiner

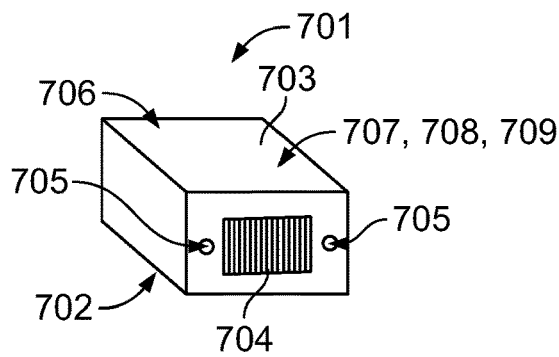
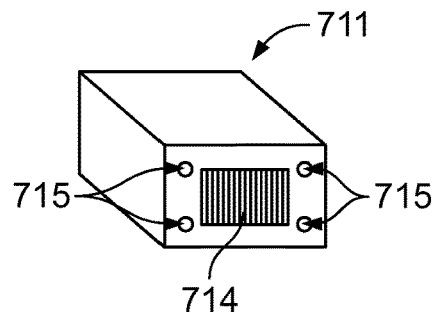
FIG. 7A    FIG. 7B
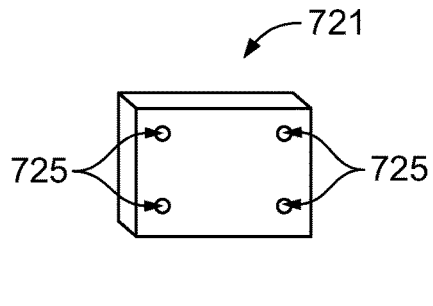
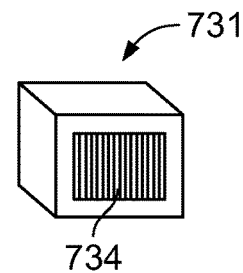
FIG. 7C    FIG. 7D
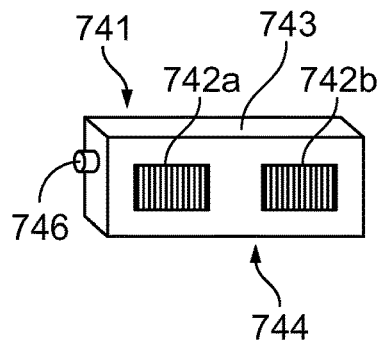
FIG. 7E
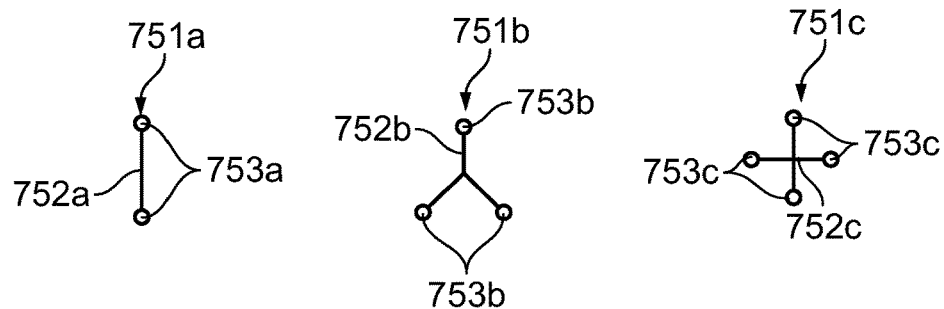
FIG. 7F

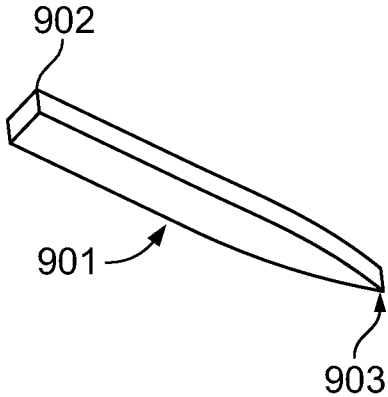
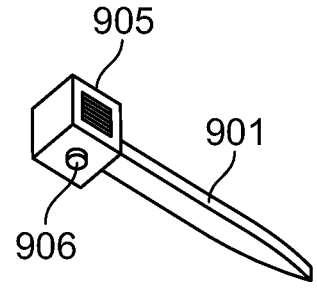
FIG. 9A  FIG. 9B
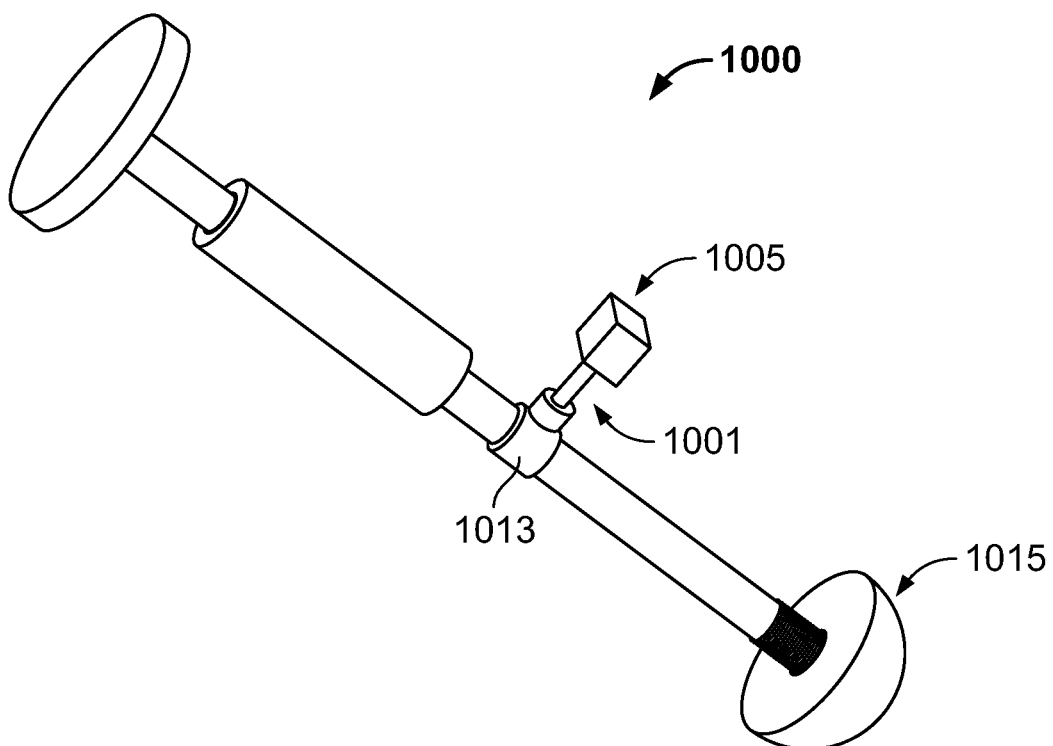
FIG. 10

METHOD AND SYSTEM FOR DETERMINING A RELATIVE POSITION OF A TOOL

CROSS-REFERENCE TO RELATED APPLICATION

This application is a continuation of U.S. application Ser. No. 17/558,151, filed Dec. 21, 2021, (the "'151 application"), the entire contents of which is incorporated herein by reference. The '151 application is a continuation of U.S. application Ser. No. 16/180,517, filed Nov. 5, 2018, (the "'517 application"), the entire contents of which is incorporated herein by reference. The '517 application is a continuation of U.S. application Ser. No. 14/799,909 (patented), filed Jul. 15, 2015, (the "'909 application"). The '909 application is a continuation of U.S. application Ser. No. 13/328,997 (patented), filed Dec. 16, 2011 (the "'997 Application"). The '997 application claims the benefit under 35 U.S.C. § 119(e) of U.S. Provisional Patent Application No. 61/424,447, filed Dec. 17, 2010, the entire disclosure of which is herein incorporated by reference in its entirety.

TECHNICAL FIELD

The present disclosure relates generally to determining, monitoring and displaying the relative positioning of two rigid bodies during surgery. In particular, the present disclosure relates to methods and systems for positioning a prosthesis relative to a bone during a surgery as well as to systems and methods for verifying resulting relative positioning of adjacent bones.

BACKGROUND

Joint replacement surgery involves replacing an existing joint with artificial prosthetic components. Examples of common joint replacements include hip replacements and knee replacements. Hip replacement may be segmented into three types: primary, revision and resurfacing. Primary hip replacement, also called Total Hip Arthroplasty (THA), involves the surgical excision of the head and proximal neck of the femur and removal of the acetabular cartilage and subchondral bone. Commonly, an artificial canal is created in the proximal medullary region of the femur, and a metal femoral prosthesis is inserted into the femoral medullary canal. An acetabular component or implant is then inserted proximally in the enlarged acetabular space.

Hip resurfacing, like THA, involves the surgical removal of the acetabular cartilage and subchondral bone, and the subsequent insertion of an acetabular prosthetic. Unlike THA, resurfacing does not involve the excision of the femoral head, but rather covering the existing femoral head with a prosthetic cap, which mates with the acetabular prosthetic. Hip resurfacing is often done with younger patients to preserve femoral bone stock for future revisions.

Revision hip surgery is typically performed when an artificial hip joint fails, due to factors such as infection, loosening, fracture, mechanical failure or instability. Revision hip surgery typically involves the replacement of one or more of the failed artificial prosthetics, depending on the reasons for failure.

Nearly 1,000,000 hips are replaced in North America and Europe every year. Approximately 75% of these procedures are primary, with 15% revision and 10% resurfacing. Studies indicate that the number of hip replacements will increase over the coming years due to many factors.

An important aspect of hip replacement is ensuring proper alignment of the acetabular component or implant with respect to the pelvis. Specifically, studies have shown that failure to properly align the acetabular component or implant with the pelvis may lead to premature wear, propensity to dislocate and patient discomfort.

Another important aspect of hip replacement is ensuring the change in leg length and offset resulting from the procedure is acceptable. Typically, the goal is to leave the leg length and offset unchanged as a result of the procedure. However, surgeons will often incorporate a small change in leg length as a corrective measure.

BRIEF DESCRIPTION OF THE DRAWINGS

For a better understanding of embodiments of the systems, methods and devices described herein, and to show more clearly how they may be carried into effect, reference will be made, by way of example, to the accompanying drawings in which:

FIG. 7A is one embodiment of a sensor unit;

FIG. 7B is another embodiment of a sensor unit;

FIG. 7C is another embodiment of a sensor unit;

FIG. 7D is another embodiment of a sensor unit;

FIG. 7E is another embodiment of a sensor unit;

FIG. 7F is an embodiment of a marker array;

FIG. 9A is an isometric view of a stylus;

FIG. 9B is an isometric view of the stylus of FIG. 9A having a sensor unit coupled thereto;

FIG. 10 is an isometric view of the acetabular implant insertion tool with a stylus and sensor unit attached;

DETAILED DESCRIPTION

Figure 1:
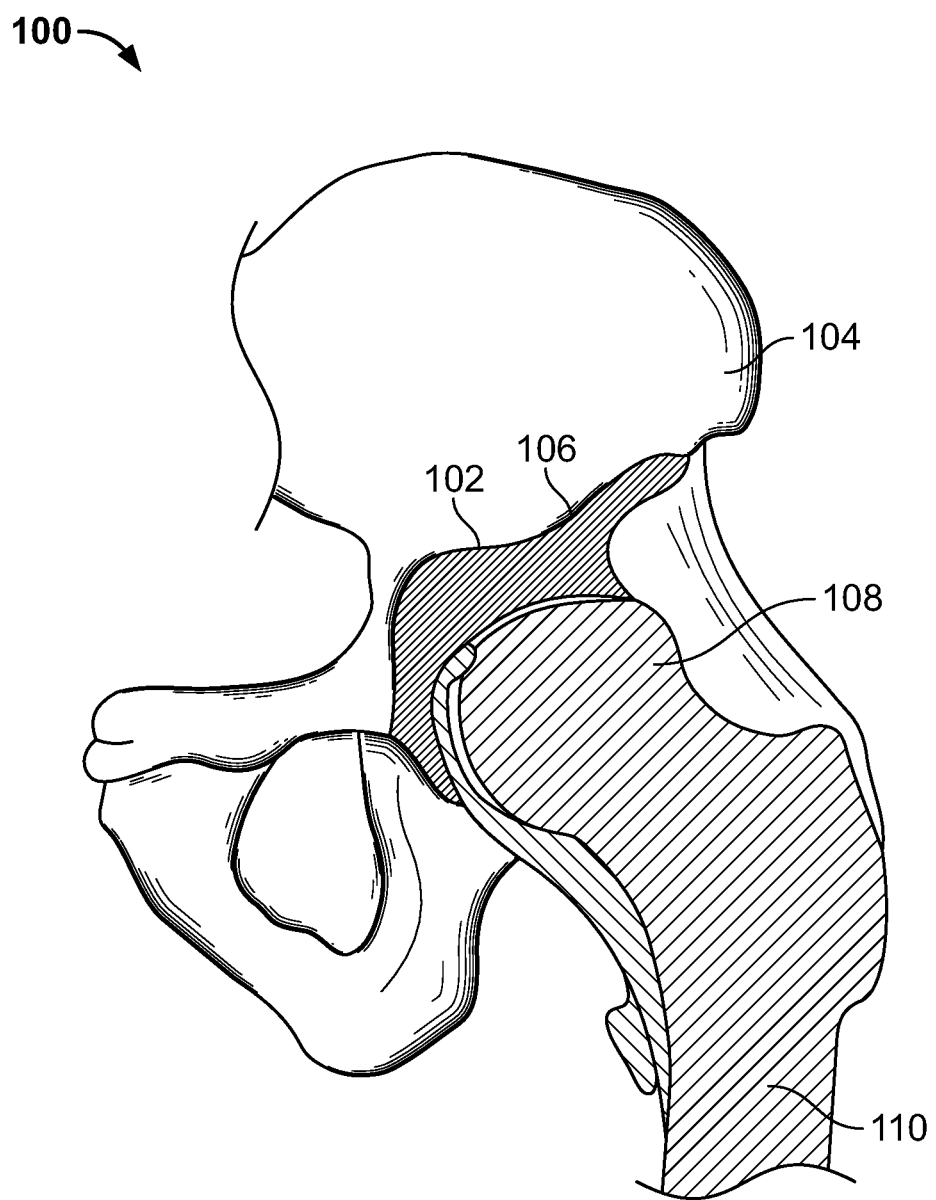
FIG. 1 is a front view of a healthy hip joint.

It will be appreciated that numerous specific details are set forth in order to provide a thorough understanding of the exemplary embodiments described herein. However, it will be understood by those of ordinary skill in the art that the embodiments described herein may be practiced without these specific details. In other instances, well-known methods, procedures and components have not been described in detail so as not to obscure the embodiments described herein. Furthermore, this description is not to be considered as limiting the scope of the embodiments described herein in any way, but rather as merely describing the implementation of the various embodiments described herein.

The described embodiments relate to methods and systems for aligning, positioning and sizing prostheses during surgery. The exemplary methods and systems relate to determining the positional relationship of body parts with prostheses, body parts with other body parts, body parts with tools and prostheses with tools. The term "positional relationship" refers to a rigid-body transformation between coordinate systems (e.g. a homogenous transformation). In Cartesian space (i.e, 3D space), the rigid-body transformation consists of 6 Degrees-of-Freedom (DOF): 3-DOF for translational position and 3-DOF for rotational position, or orientation. In this document, the terms "positional relationship" or "relative position" encompass 1 to 6 DOF. The number of DOF of a positional relationship may be explicitly stated (e.g., 2-DOF), or implied by the context (e.g., 3-DOF are needed to describe orientation in general). In some instances, positional relationship is determined by first determining the 6-DOF positioning, then extracting the desired positional information described by less than 6-DOF. More generally, "positional relationship" implies determining the positioning between two rigid bodies and their corresponding coordinate systems, neither of the rigid bodies being considered "fixed" to a global coordinate system.

In one embodiment, a first (or reference) sensor unit is attached to a body part, for example, the pelvis. The relative position of the body part (i.e., pelvis) with the first sensor unit must be determined. This is commonly referred to as "registration" to those skilled in the art. There are known methods to perform pelvis registration. One registration method involves using intra-operative imaging. Another method of registration involves measuring the positioning of the sensor unit with at least three landmarks (or reference locations) on the body part. A surgical tool having a second sensor unit may contact three landmarks (or reference locations) simultaneously or successively. The combination of the first sensor unit attached to the body part, and the second sensor unit on the surgical tool, may permit the relative positioning of the first sensor unit on the body part with respect to the at least three landmarks or reference locations (and therefore the body part itself), to be determined. In one embodiment, the registration determines only the 3-DOF relative rotational position (i.e., orientation) of the first sensor unit with the pelvis.

In another embodiment, the orientation of a prosthesis with respect to a body part is determined using sensor units. Such sensor units may include without limitation emitters or markers, and/or sensors. One sensor unit may be attached to the body part, with another sensor unit attached to the surgical tool. The combination of the sensors/markers may allow the relative three-dimensional orientation of the surgical tool (with the prosthesis attached) and the body part to be measured.

In another embodiment, the relative positioning of two body parts are determined using two sensor units. For example, in hip replacement surgery, one may wish to determine the relative positioning of the pelvis with respect to the femur, or point on the femur. This may be accomplished by attaching a first (or reference) sensor unit to one body part (i.e., the pelvis), and another sensor unit to the other body part (i.e., the femur), such that the combination of sensor units are able to measure the relative positioning between the two body parts.

For ease of explanation, the methods and systems will be described with reference to aligning an acetabular and femoral implant during THA. However, it will be evident to a person of skill in the art that the methods and systems described herein may be applied to other types of hip replacement, i.e., hip resurfacing, revision hip replacement, as well as to other surgical procedures where a prosthesis is implanted, such as, for example, knee replacement surgery.

I. Description of Total Hip Replacement

Before proceeding to a detailed description of the embodiments of methods and systems for aligning a prosthetic component or implant, a brief description of total hip replacement (THR) or THA will be provided with reference to FIGS. 1-4.

Reference is first made to FIG. 1, in which a healthy human hip joint 100 is illustrated. As can be seen from FIG. 1, the hip joint 100 includes a socket 102, referred to as the acetabulum, in the pelvic bone 104, which is lined with acetabular cartilage 106. In a healthy individual, the femoral head 108 at the upper end of the femur 110 is received in the acetabulum 102.

Figure 2:
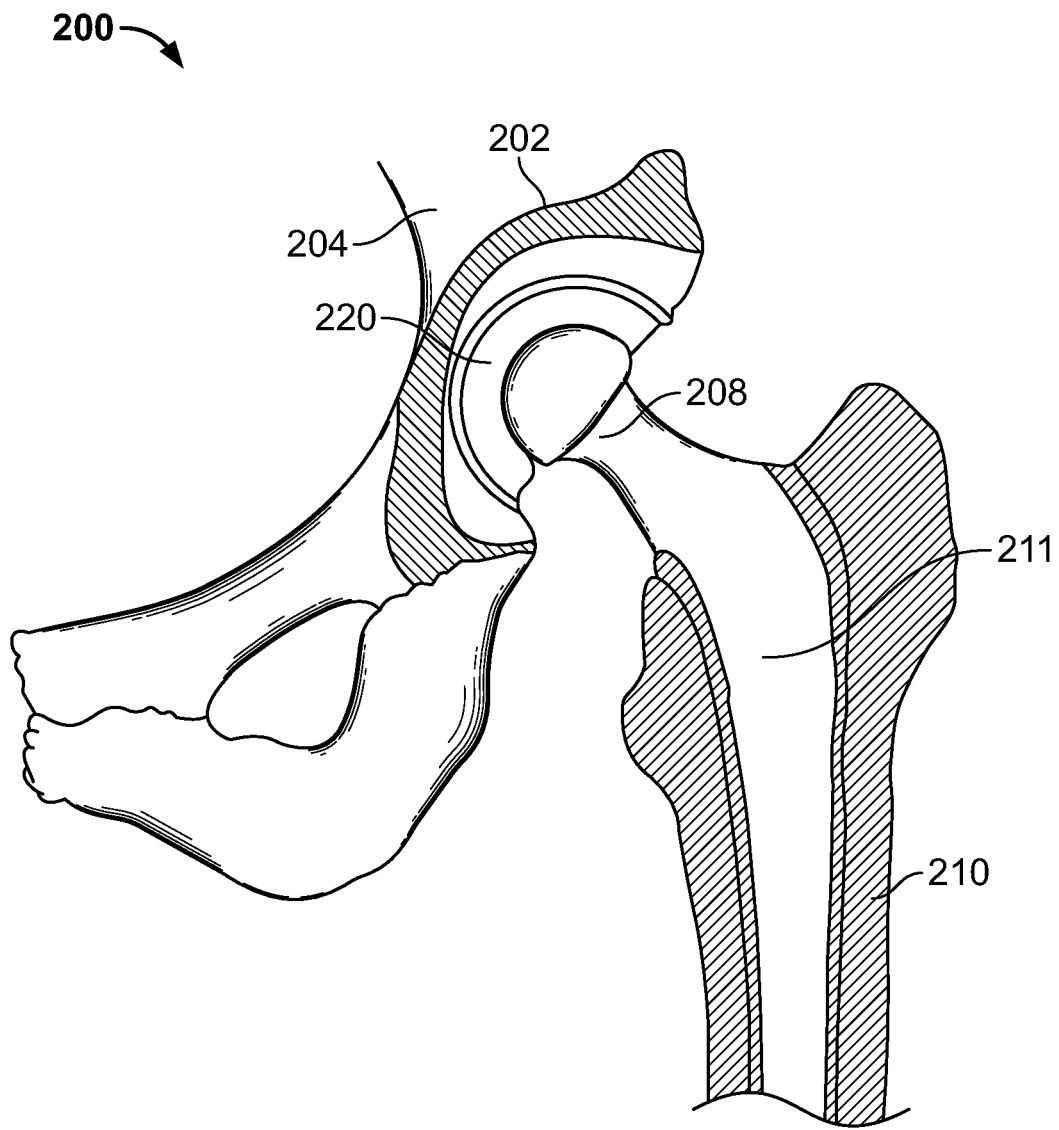
FIG. 2 is a front view of a hip joint after THA.

Reference is now made to FIG. 2, in which a human hip joint 200 after THR or THA surgery is illustrated. During THR or THA, the acetabulum 202 is reamed out (i.e. acetabular cartilage 106 of FIG. 1 is removed), and an acetabular component or implant 220 is attached to the acetabulum 202. The femoral head (e.g. femoral head 108 of FIG. 1) of the femur 210 is also removed. Specifically, the femur 210 is opened out according to known methods, and a ball and stem component 211, referred to as the femoral component, is inserted into the opened-out femur 210.

An important aspect of THA is ensuring proper alignment of the acetabular component or implant with respect to the pelvis. Specifically, studies have shown that failure to properly align the acetabular component or implant with the pelvis may lead to premature wear, propensity to dislocate and patient discomfort.

Figure 3A:
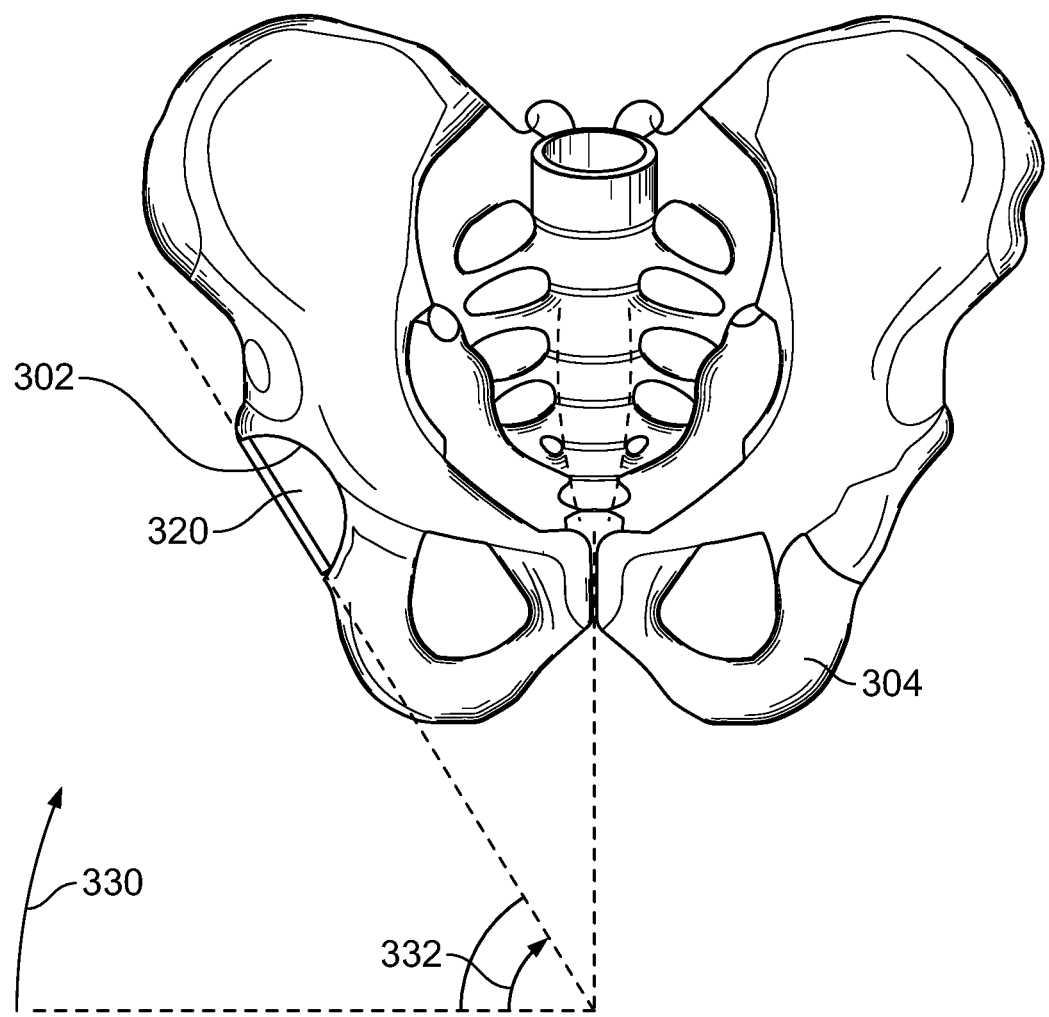
FIG. 3A is a front view of a pelvis illustrating the angle of abduction.
Figure 3B:
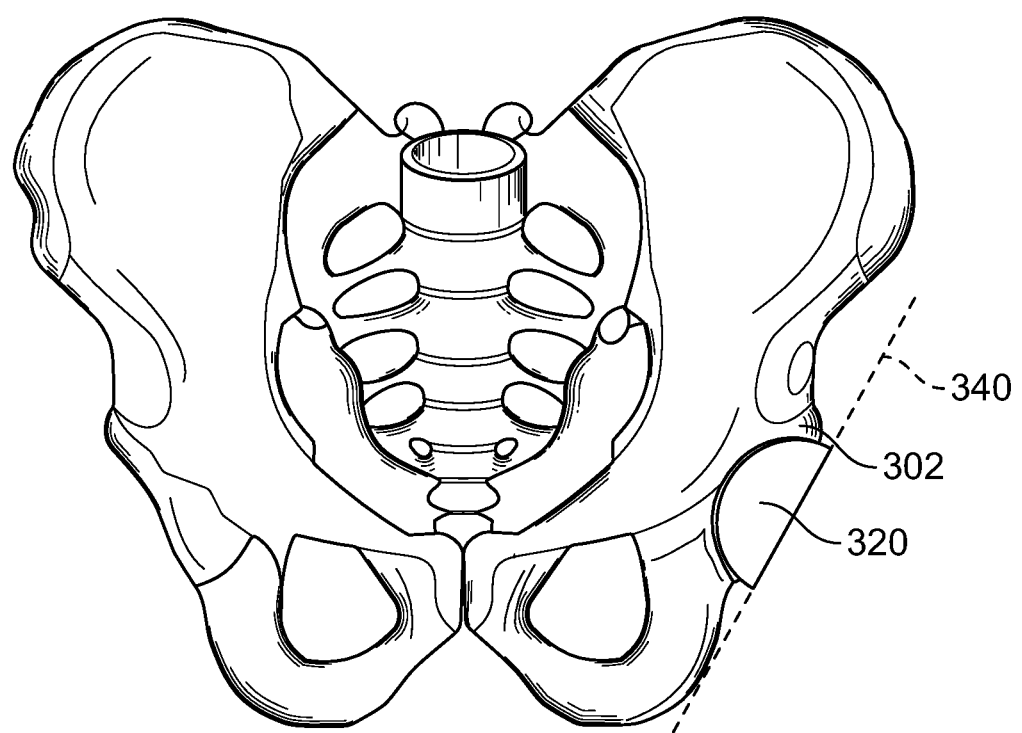
FIGS. 3B and 3C are front views of a pelvis illustrating the angle of anteversion.
Figure 3C:
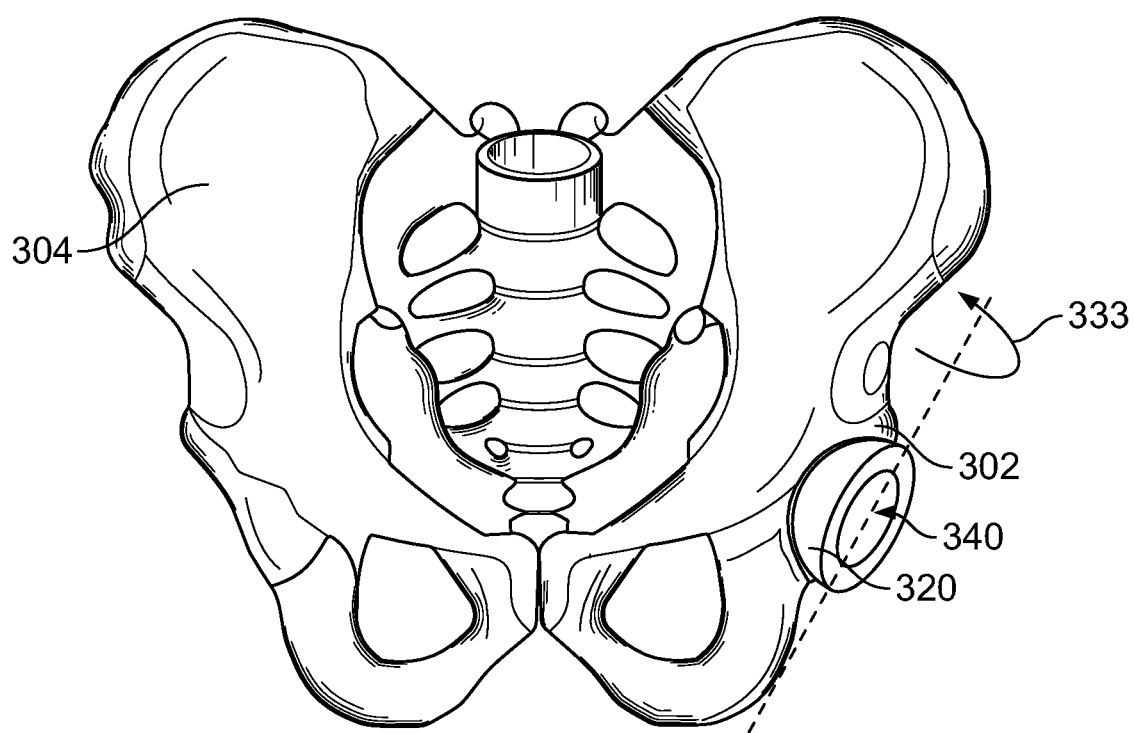

The orientation of an acetabular component or implant 220 with respect to the pelvis anatomy is defined by angles of abduction and anteversion. Reference is now made to FIGS. 3A, 3B, and 3C, which all depict a front view of a pelvis with an acetabular implant 320 to illustrate angles of abduction and anteversion. In FIG. 3A, the direction of abduction is indicated by arrow 330, and the angle of abduction is indicated by angle 332. Generally speaking, abduction relates to the sideways pivoting of the acetabular component or implant 320 within the acetabulum 302.

Referring now to FIGS. 3A-3C, the direction of anteversion is indicated by arrow 333. FIG. 3B shows the acetabular implant 320 with zero degrees of anteversion. Rotation of the acetabular implant 320 about the axis 340 such that the socket of the implant is visible to the reader constitutes a positive angle of anteversion. For example, the acetabular implant 320 of FIG. 3C has a positive angle of anteversion. Generally speaking, anteversion relates to the tilting of the acetabular component or implant 320 within the acetabulum 302 in a vertical direction (i.e. a vertical direction with respect to a patient lying face up on an operating table). Abduction and anteversion may be defined operatively, radiographicly, and anatomically.

Studies have shown that for a typical healthy patient, the range of abduction is ideally between 30 and 50 degrees, and the range of anteversion is ideally between 5 and 25 degrees.

Figure 4B:
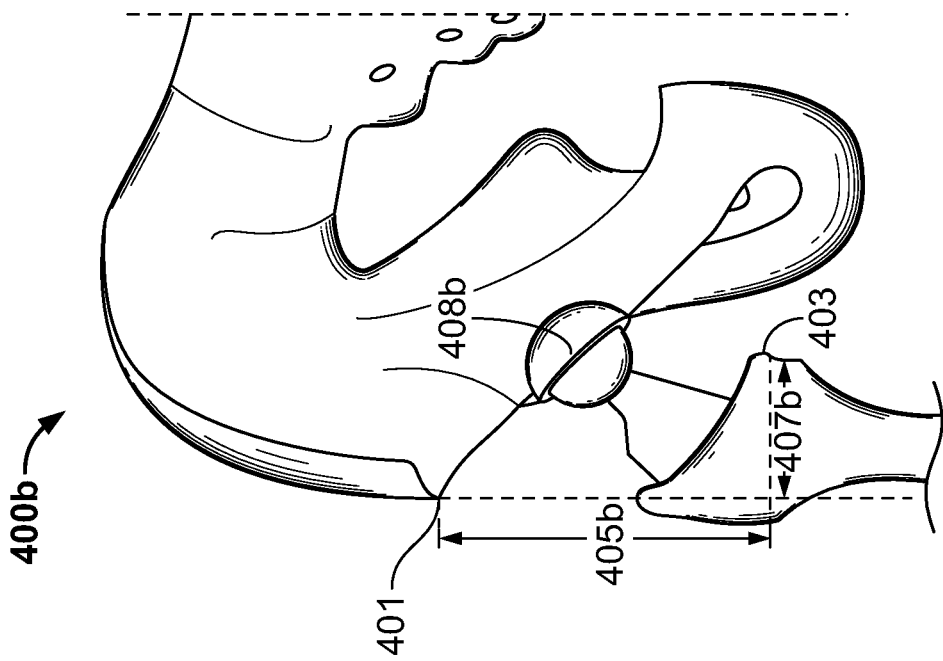
FIGS. 4A and 4B are comparative diagrams of a hip joint, illustrating the measures of leg length and offset before and after the hip replacement procedure, respectively.
Figure 4A:
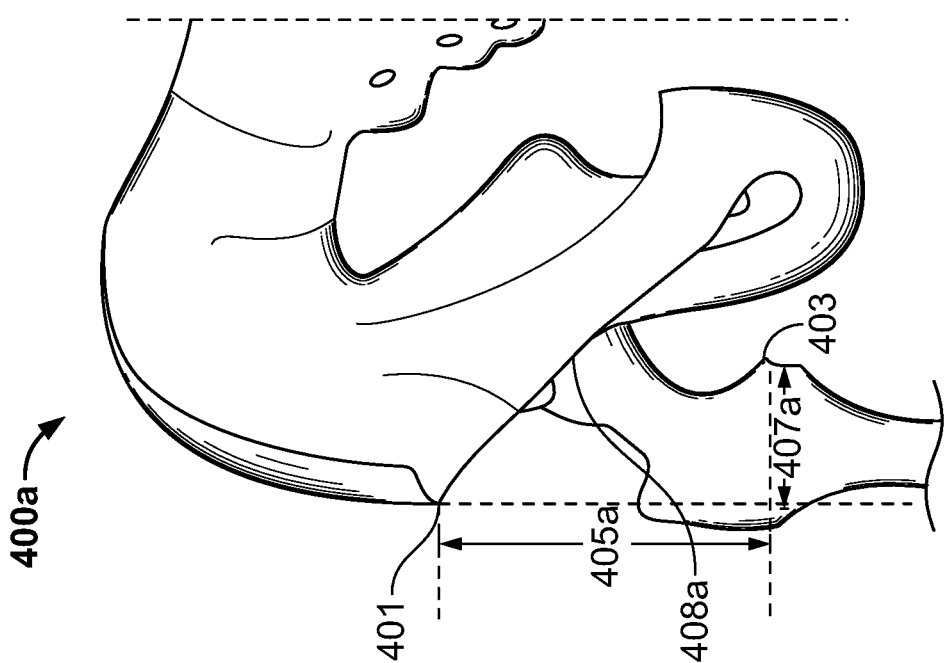

Also highly desirable to the successful outcome of a hip replacement is achieving a desired resulting leg length, offset and center of rotation of the femur. The definition of leg length and offset with respect to the anatomy of a body is documented in the literature and is known to those skilled in the art. With reference to FIGS. 4A and 4B, a hip and femur before replacement 400a (FIG. 4A) and after replacement 400b (FIG. 4B) are shown from an anterior-posterior view. The original leg length 405a and offset 407a are components of the vector between a landmark (or reference location) on the pelvis 401 and a landmark on the femur 403. The resulting leg length 405b and offset 407b are components of the vector between the same landmarks: on the pelvis 401 and the femur 403. The resulting leg length 405b and offset 407b are determined by the location of the center of rotation (COR) of the femur 408b, as well as the dimensions of the femoral implant. The original leg length 405a and offset 407a may be measured using a pre-operative scan (e.g. x-ray, CT scan, and MRI), as well as the original femoral COR 408a. A desired change in leg length and offset may be calculated based on a desired resulting leg length and offset and the original leg length 405a and offset 407a.

It may be important that the resulting leg length 405b and offset 407b match the pre-operatively determined desired values, with respect to the original leg length 405a and offset 407a, in order to help ensure a successful surgery and desired mobility and durability of the prosthetic joint. A desired resulting leg length and offset may be achieved by monitoring the leg length and offset during surgery (using sensor units) and effecting the desired change in leg length and offset. It may also be desirable to determine the pre and post operative femoral COR position, including the Anterior-Posterior change of the femoral COR position. This may be accomplished using sensor units.

II. System Level Description of Apparatus

Figure 5:
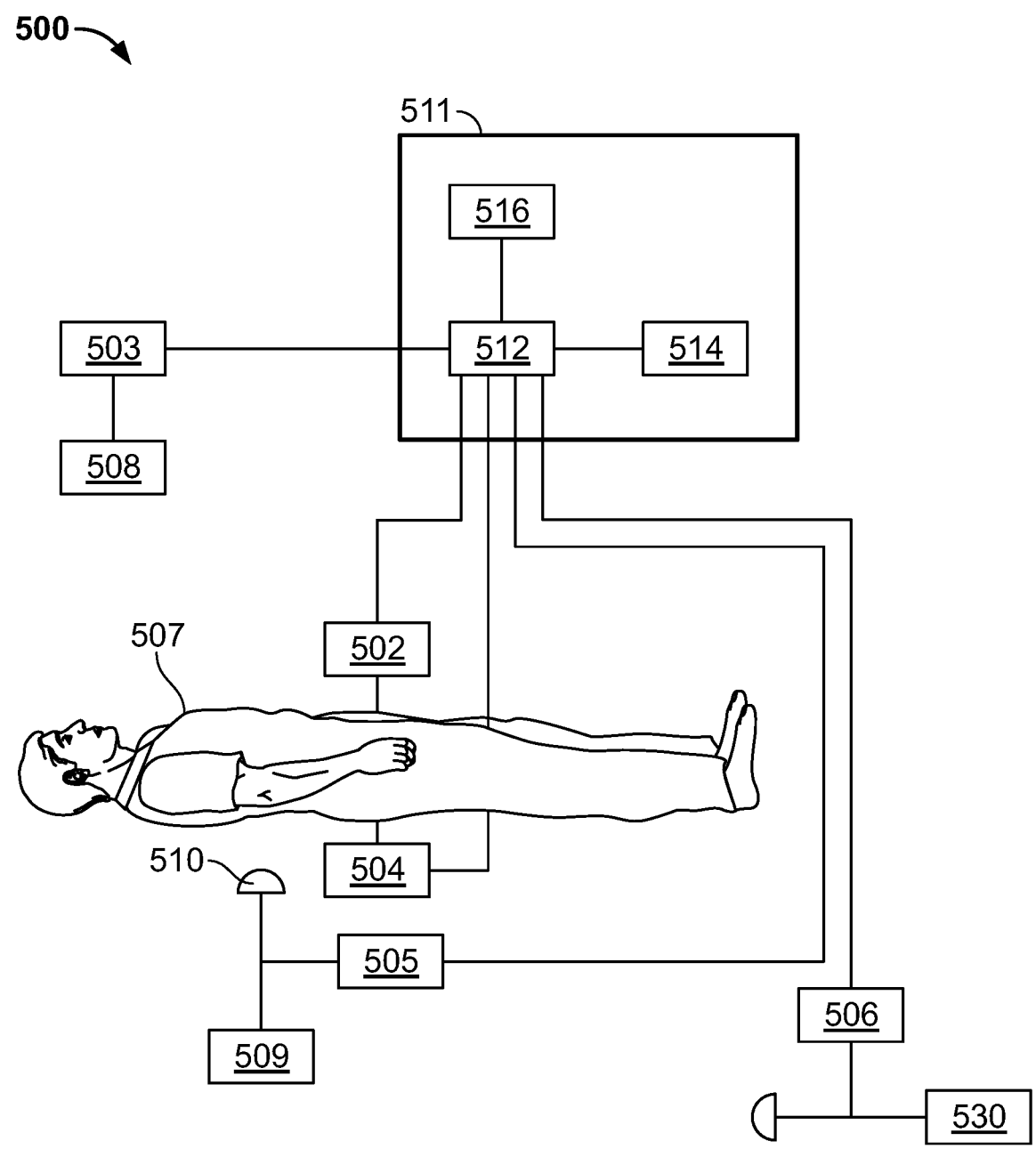
FIG. 5 is a block diagram of a system for a surgical navigation system for hip replacement in accordance with at least one embodiment.

Reference is now made to FIG. 5, in which a system 500 for measuring the relative positioning of body parts with body parts, body parts with prostheses, body parts with tools and tools with prostheses in accordance with an embodiment of the present invention is illustrated. The exemplary system 500 includes a plurality of sensor units 502, 503, 504, 505, and 506, that cooperate to measure relative positioning between the components to which they are connected (wherein the connections shown in FIG. 5 denote wired or wireless transmissions). A first sensor unit (or reference sensor unit) 502 is operatively connected to the pelvis of a patient 507, for example by fixing a pin or bone screw into the patent's pelvis and by screwing, clipping or otherwise mounting the first (or reference sensor unit) 502 to the pin or bone screw, as will be discussed further below. A second sensor unit 503 is operatively connected to a sensor positioning device 508. Additional sensor units 504, 505, and 506 are operatively connected to a femur of the patient 507, an acetabular prosthesis insertion tool 509, and a reaming device 530, respectively. As will be described in further detail below, each of sensors 503, 504, 505, and 506 may be substituted for a marker or marker array.

Acetabular prosthesis insertion tool 509 and reaming device 530 are merely examples of surgical tools (or rigid bodies) that may form part of the system 500, and are commonly used during hip replacement surgery. The ordinary skilled person will appreciate that different surgical tools used to attach other medical prostheses to corresponding body parts or bones of the patient are also contemplated herein. The system 500 may also include a computing device 511 which may comprise a processor 512, a display device 514, and a database 516.

The display device 514 may display information related to the surgical procedure. Typically the displayed information is intended for the surgeon, for example, the orthopaedic surgeon during hip replacement. The display device 514 may be a computer monitor, television, LCD touchscreen, seven segment display, tablet, smart phone or any other type of display. The display device 514 may be a stand-alone unit, currently integrated in the operating room, or may be attached to a surgical tool, e.g., 509, 530. The information being displayed may include, but is not limited to, relative positioning information of body parts, tools, or prostheses. In one embodiment, the display device 514 shows the angles of abduction and anteversion of the acetabular component. In another embodiment, the display device 514 shows reaming depth and angle information. In another embodiment, the display device 514 shows the change in leg length and offset. Other relevant information to the surgery may also be displayed. For example, medical imaging, where available, may be displayed, along with a representation (e.g. an augmented reality representation) tracking the real time movement the various surgical tools and bones involved in the surgical procedure.

In the exemplary embodiment, the computing device 511 interfaces with at least one of the sensor units 502, 503, 504, 505, 506 and the display device 514. The computing device 511 receives sensor data, and processes it to determine relative positioning information. In one embodiment, the processing includes using the Extended Kalman Filter (EKF), or a variation of it (i.e., the Iterative EKF). In another embodiment, the processor 512 includes a nonlinear iterative solver such as the Levenberg-Marquardt method. The sensor data that computing device 511 receives contains enough information to determine the desired relative positioning data (in other words, the desired relative positioning data is preferably at least locally observable given the sensor information— the term "locally observable" being used as it is commonly understood in the art of control and estimation). The computing device 511 formats the data and, in some embodiments, may relay the formatted data to a database 516 for storage. Additional information relevant to the surgical procedure, but not necessary for determining relative positioning (e.g. date, time, and personal information about the patient), may also be sent to a database 516 for storage. The database 516 may be located in the operating room, in the hospital, in a central medical information repository, or any other location where storing data securely is possible.

The computing device 511 may also send processed data to a display 514, and may comprise other user input devices, such as a keyboard or mouse (not shown), which may be used to interact with information displayed on 514. Furthermore, the computing device 511 may interface with medical imaging data (e.g. x-rays, CT scans, MRI), and may in turn display this data to the display 514.

A. Hip prosthetic alignment system and method.

Figure 6:
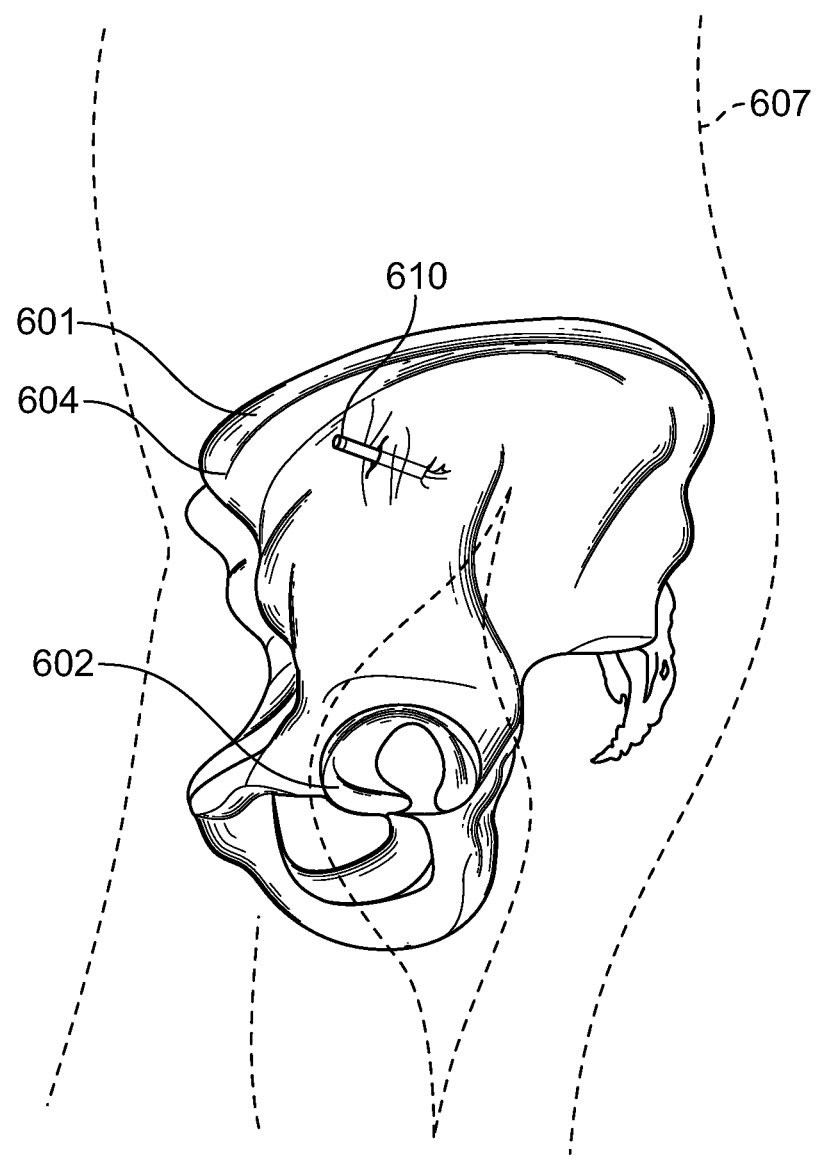
FIG. 6 is a side view of a patient's hip having a pin or bone screw inserted in the pelvis through skin or other soft tissue.

Many orthopaedic surgeons fasten a pin or bone screw to the pelvis during hip replacement. With reference to FIG. 6, an example of a pin or bone screw 610 rigidly fastened to the ilium 601 of the pelvis 604 of a patient 607 (represented by a dashed line) is shown. In this instance, the pin or bone screw 610 has been inserted through skin and other soft tissue of the patient 607 and fixed to the patient's ilium 601 by screwing or impacting, though operatively connecting 610 may be done on other locations on the pelvis (e.g., in the surgical wound). As will be further described below, the pin or bone screw 610 may be used as an interface to mount a sensor unit. For example, pin or bone screw 610 may be used to mount a first (or reference or pelvis) sensor unit (e.g. sensor unit 502 of FIG. 5) to the pelvis 604 of the patient 607. A similar pin or bone screw may also be used to mount a separate (or second) sensor unit (e.g. sensor 504 of FIG. 5) to a femur (not shown) of the patient 607. A sensor unit may be mounted to a pin or bone screw, for example, by screwing the sensor onto a threaded end of the pin or bone screw extending from patient's pelvis, or by clipping, or otherwise fastening the sensor unit onto the end of the bone screw or pin. It will be apparent to those skilled in the art that other means of operatively connecting a sensor unit to a bone may be used (e.g., a bio-compatible adhesive).

With reference to FIGS. 7A to 7D, four different sensor units 701, 711, 721, 731 are described. FIGS. 7A, 7B, and 7D provide examples of sensor units (701, 711, and 731, respectively) having at least one optical sensor embedded (704, 714, and 734, respectively).

An optical sensor refers to any sensor capable of receiving light, and determining the direction of the light source. A typical optical sensor may be a CMOS, CCD, or other type of camera. Another example of an optical sensor is a photo-sensitive device (PSD). Another example of an optical sensor is a product called Shadow Sense, offered by Baanto Inc. (Mississauga, ON). Other examples of optical sensors will be apparent to those skilled in the art. In one embodiment, the optical sensor receives infra-red (IR) light; however, optical sensors are not to be limited herein to sensing light in the IR spectrum.

FIGS. 7A to 7C provide examples of sensor units 701, 711, and 721, respectively, having markers (705, 715, and 725, respectively). In one embodiment (particularly, where IR optical sensors are used), the markers are IR markers. An ordinarily skilled person will appreciate that a marker is not required to be of the IR variety, but rather may comprise any object which appears as an identifiable feature on an image taken by a corresponding optical sensor. Other examples of markers include, but are not limited to, retro-reflective markers (which preferably accompany a light-energy source directed towards the marker), and light emitting diodes (LED). Markers 705, 715, and 725 have been illustrated as point light sources. It will be apparent to those skilled in the art that non-point light sources may be used, and may have benefits over point light sources.

With reference to the sensor unit 701 of FIG. 7A, sensor unit 701 may be coupled to a rigid body (e.g. a bone or surgical tool) via mounting bracket 702. For example, sensor unit 701 may be coupled to a bone screw or pin (e.g. 610 of FIG. 6) via mounting bracket 702. Sensor unit 701 is enclosed by housing 703. Sensor unit 701 contains at least one optical sensor 704, not obstructed by the housing 703. Sensor unit 701 contains two markers 705. Sensor unit 701 may also contain additional sensors 706 within the housing. The additional sensors 706 may include but are not limited to accelerometers, gyroscopes, and magnetometers.

A processor 707 may be embedded within the sensor unit 701. The embedded processor 707 may convert analog data to digital data, and may filter or otherwise condition data and prepare said data for transmission via the communication channel 709. Communication channel 709 may be wired, or wireless, and may communicate over any suitable protocol (e.g. RS-232, BlueTooth®, WiFi, USB, SPI, I2C, IR). Sensor unit 701 is powered by a power source 708, which may include but is not limited to an internal battery, or an external power cable. In embodiments where a battery is used as the power source 708, the sensor unit 701 may also be equipped with recharge terminals (not shown).

A sensor unit in general may have a plurality of markers. For example, FIG. 7B illustrates an exemplary sensor unit 811, which has four markers 715. Sensor unit 711 is otherwise similar to sensor unit 701. When more than 3 markers are placed on a sensor unit, it may be advantageous for the markers to be positioned such that they do not lie in the same plane (e.g., sensing may be more robust).

FIG. 7C illustrates a sensor unit 721 having four markers 725, but no optical sensor. Sensor unit 721 is otherwise similar to sensor units 701 and 711. As mentioned, it may be advantageous that, where greater than 3 markers are used, the markers are not all co-planar.

FIG. 7D illustrates a sensor unit 731 having an optical sensor but no markers. Sensor unit 731 is otherwise similar to sensor units 701, 711, and 721.

In general, to measure 6-DOF relative positioning between 2 sensor units, at least one optical sensor and at least three markers are required between the two sensor units. It is preferable to have more than the minimum combination of optical sensors and markers. To measure relative positioning in less than 6-DOF, fewer markers may be required.

Figure 8:
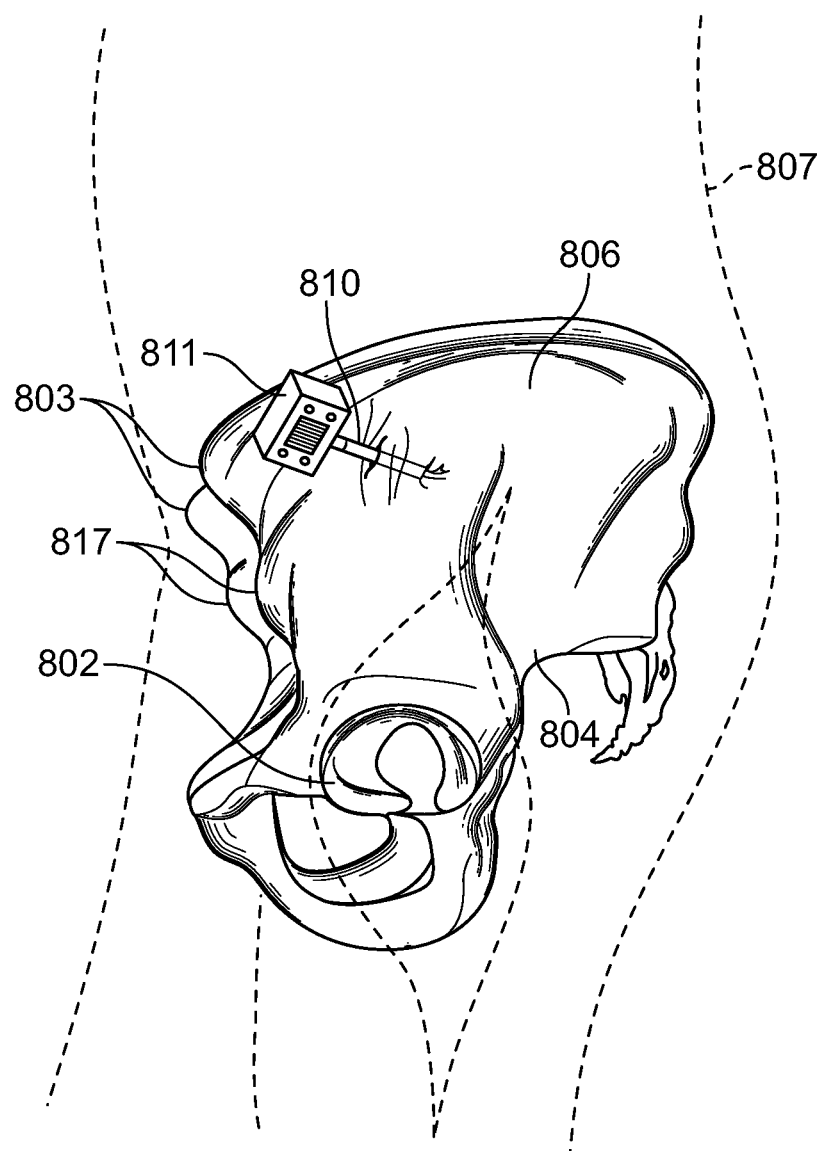
FIG. 8 is a side view of a patient's hip with a sensor unit coupled to the pelvis via a pin or bone screw in the pelvis.

Reference is now made to FIG. 8, in which the pelvis 804 of a patient 807 (shown as a dashed line) is illustrated. A pin or bone screw 810 is attached to the patient's pelvis 804 and sensor unit 811 is mounted thereto and functions as a first (or reference or pelvis) sensor unit. Sensor unit 711 (FIG. 7) has been selected as the first (or reference or pelvis) sensor unit 811 for exemplary purposes.

The purpose of the first (or reference or pelvis) sensor unit 811 is to provide sensor measurements (in a pelvis frame of reference) to a computing device (e.g. 511 of FIG. 5), to ultimately determine relative positioning information between other components of the system (e.g. the pelvis bone, the femur, surgical tools, and prosthetics). The pelvis frame of reference is related to sensor unit 811 by a method such as registration. In one embodiment, registration is performed by locating a plurality of landmarks or reference locations (e.g. the anterior superior iliac spine (ASIS) 803, the anterior inferior iliac spine (AIIS) 817, and points along the iliac crest 806) on the patient's pelvis with respect to the first (or reference or pelvis) sensor 811.

With reference to FIGS. 9A and 9B, a stylus 901 that may be used (along with a sensor), in one embodiment, to locate landmarks (or reference locations) on the patient's pelvis with respect to the first (or reference or pelvis) sensor unit (e.g. 811 of FIG. 8) is described. Stylus 901 comprises a rigid body having a proximal end 902 and a distal end 903. The distal end 903 has a well-defined contact point to be used to contact body parts and/or other features or landmarks (or reference locations), and the proximal end 902 is adapted to receive a sensor unit 905. Sensor unit 905 may be one of sensor units 701, 711, 721, or 731, illustrated in FIG. 7 and may additionally be equipped with at least one human interface sensor, such as button 906. The button 906 may be interfaced with a processor (not shown) internal to the sensor unit 905. In one embodiment, the stylus 901 is used to determine the positioning of landmarks or reference locations (e.g. 803, 817, and 806 of FIG. 8) on the pelvis with respect to the first (or reference or pelvis) sensor unit 811 (FIG. 8). Depression of the button 906 may signal to the computing device (e.g. 511 of FIG. 5) and/or first (or reference or pelvis) sensor (e.g. 811 of FIG. 8) that the stylus is in contact with a landmark or reference location, and accordingly that the sensor unit 905 is in a pre-determined location with respect to the landmark or reference location. Depression of the button 906 may also cause the relative positioning of the sensor unit 905 to be registered/saved.

With reference to FIG. 10, an acetabular cup insertion tool 1000 having a sensor unit 1005 attached thereto, according to one embodiment, is described. The sensor unit 1005 is secured to the tool 1000. In one embodiment, the sensor unit 1005 is the same sensor as sensor 905 (FIG. 9). In one embodiment the sensor unit 1005 is the same sensor as sensor 905, also attached to stylus 901 (FIG. 9), and the stylus 901 is directly attached to the acetabular cup insertion tool 1000—in this embodiment, the stylus 901 may be secured to the tool 1000 by securing a free end 903 of the stylus 901 within a coupler 1013, for example using a set screw (not shown). In alternative embodiments, the coupler 1013, which may be integrally formed with the tool 1000, may be provided with threads for mating with complementary threads on one end of a couple (e.g. a pin) 1001, and the other end of the coupler (e.g. a pin) 1001 may be provided with threads for mating with complementary threads provided to sensor unit 1005. Alternatively to using threads, a mechanical clip, for example, may also be used to couple the sensor unit 1005 to the coupler 1001 and the coupler 1001 to coupler 1013 of the tool 1000. The sensor unit 1005 may comprise any one of the sensor units 701, 711, 721, and 731 described with reference to FIG. 7. Furthermore, sensor 1005 may be coupled to the insertion tool 1000 via a coupler 1001, which, in one embodiment, may be the stylus 901. The end of the insertion tool 1000 holds the acetabular prosthetic implant (or acetabular cup) 1015. The sensor unit 1005 is connected to the tool 1000 in a known or measurable orientation such that the relative position of the sensor unit 1005 with respect to the insertion tool 1000 is known when the two elements are connected. For example, where an insertion tool, coupler, and sensor are manufactured to known dimensional specifications, and such that the three components may only be assembled in one particular fashion, the three components may be assembled in a predictable manner according to calculated relative positioning. Where the dimensions of one or more of the components used are adjustable (e.g. the pelvis registration device described directly below), the relative position of the components may be determined by measuring distances and angular orientations between the components.

In another embodiment described with reference to FIG. 11, a pelvis registration device 1100 may be used to contact three landmarks (or reference locations) on the pelvis. In one embodiment, the first and second contact members 1117, 1106 are used to contact the respective ASIS points 1103 at first and second contact points 1107, 1109, respectively, on the contact members 1117, 1106, and a third contact member 1110 to contact a palpable location on the iliac crest 1105 at a third contact point 1111 on third contact member 1110. Other pelvic landmarks (reference locations) may be used, and would be apparent to those ordinarily skilled in the art (e.g. the Anterior Inferior Iliac Spine, the pubic tubercles, the acetabular rim, the attachment point of the ligamentum teres, etc.). An example device is disclosed in PCT publication number WO/2010/063117, which is incorporated by reference herein in its entirety. The first and second contact members 1117, 1106 are attached to first and second adjustable stand-offs 1114, 1116, which are themselves secured to a cross-member 1124. The rigid member (or shaft) 1102 is free to rotate about the axis of its length, or alternatively may be clamped such that it may not rotate, and extends beyond stand-off 1114 (the portion of the rigid member or shaft extending beyond stand-off 1114 being indicated as 1122).

The third contact member 1110 is attached to a third stand-off 1108, which is coupled to the extended portion 1114 of the rigid member (or shaft) 1102 via joint 1118. The third stand-off 1108 is preferably operatively coupled to the rigid member (or shaft) 1102 such that the rotation of the rigid member (or shaft) 1102 about the axis of its length causes a similar rotation of the third stand-off 1108 about said axis. By way of non-limiting example, the third stand-off may be integrally formed or welded with the rigid member (or shaft) 1102 (or portion 1122 of the rigid member or shaft extending beyond stand-off 1114).

The third contact member 1110 is suitably shaped to contact a palpable point along the iliac crest 1105. A coupler 1131 is connected to the third stand-off 1108 and a second sensor unit 1130 is connected to the coupler 1131. By way of non-limiting example, the coupler 1131 may be a pin with two threaded ends adapted to mate with complementary threads in the third stand-off 1108 and the second sensor 1105. It will be appreciated by those skilled in the art that, although it is preferable that the coupler 1131 be connected to the third stand-off 1114, the coupler may alternatively be connected to a separate component of the registration device 1100, provided that the separate component of the registration device to which the coupler 1131 (and the second sensor 1130 when coupled to the coupler 1131) is coupled is operatively connected to the third stand-off 1108 (i.e. a rotation of the third stand-off 1108 about an axis of rotation will cause a similar rotation of the separate component about the same axis of rotation). It is also preferable that the relative position of the second sensor unit 1130 with respect to the first, second, and third contact points 1107, 1109, 1111, is known when the second sensor unit 1130 is coupled to a component of the pelvis registration device 1100 via the coupler 1131 (i.e. the second sensor unit 1130, when coupled to the pelvis registration device 1100, has a pre-determined relationship to each of the first, second, and third contact points 1107, 1109, 1111).

As such, all of the mechanical dimensions of the pelvis registration device 1100 are either fixed and known, or adjustable and measurable. Furthermore, at least one human interface sensor (e.g. button 1132), which may be located anywhere on the pelvis registration device 1100, may be interfaced to the sensor unit 1130 for the purpose of communicating to the computing device (e.g. 511 of FIG. 5) that the device 1100 is in position with respect to the patient's pelvis. In one embodiment, the button 1132 comprises three pressure sensors at each of the first, second, and third contact points 1107, 1109, 1111, such that a particular pressure at each point will indicate to the computing device (e.g. 511 of FIG. 5) that the pelvis registration device 1100, is in the desired position with respect to the pelvis.

The pelvis registration device 1100 may be used to determine the positioning of landmarks or reference locations (e.g. 803, 817, and 806 of FIG. 8) on the pelvis with respect to the first (or reference or pelvis) sensor unit 811 instead of the stylus embodiment described with reference to FIGS. 9A and 9B. Similarly to second sensor unit 905 of FIG. 9, second sensor 1130 may be one of sensor units 701, 711, 721, or 731, illustrated in FIG. 7.

Figure 12:
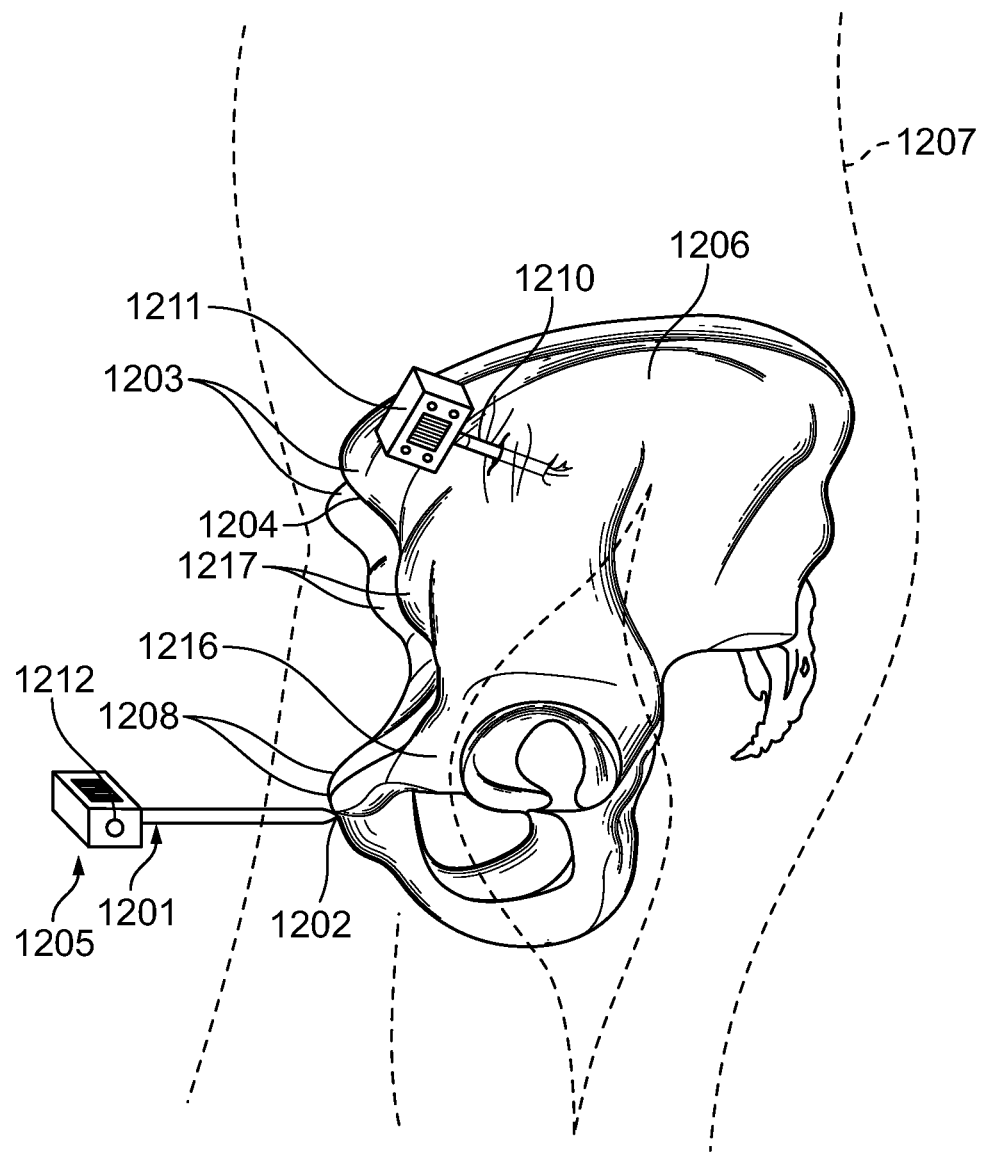
FIG. 12 is a side view of the patient's pelvis having a sensor unit attached thereto along with a stylus having a sensor unit contacting a landmark on the pelvis.

With reference to FIG. 12, a method for determining the relative positioning of a first (or reference or pelvis) sensor unit 1211 with respect to the pelvis 1204 of a patient 1207 (shown in dashed lines) using the stylus/sensor unit combination of FIG. 9, is described. With the first (or reference or pelvis) sensor unit 1211 operatively connected to the pelvis 1204 of the patient 1207 (for example, as described above), the stylus 1201 is brought into contact with a pubic tubercle 1208 (a bony landmark on the pelvis 1204) using the distal end 1202 of the stylus 1201 (as illustrated in FIG. 12). When the stylus 1201 is appropriately engaged with a bony landmark (either directly on the bone, or through skin and other soft tissue), button 1212 may be depressed to indicate that the stylus 1201 is engaged, which initiates a communication transmission from second sensor unit 1205 to either a computing device (e.g. 511 of FIG. 5) or the first (or reference or pelvis) sensor unit 1211. In one embodiment, first (or reference or pelvis) sensor unit 1211 and second sensor unit 1205 will be selected and positioned such that one of the sensors comprises at least one camera and the other sensor comprises corresponding markers that lie within the at least one camera's field of view at the time of communication transmission. At the time of communication transmission, the aggregate information available to sensor units 1211 and 1205 is sufficient to determine the relative 6-DOF positioning between the sensor units 1211 and 1205. Therefore the 6-DOF positioning of the first (or reference or pelvis) sensor 1211 relative to the bony landmark in contact with the stylus 1201 at the time of communication transmission, may be determined.

In one embodiment, it may be desirable to register the femur (often for use in determining leg length/offset). In such an embodiment, it is possible to contact landmarks along the femur using stylus 1201.

Those skilled in the art will appreciate that certain combinations of sensor units 1211 and 1205 will be deficient for the purpose of providing sufficient information to determine relative positioning. For example, if sensor unit 721 of FIG. 7 (comprising only markers, and no camera) is used as sensor unit 1211, then sensor unit 721 may not be used as sensor unit 1205, and vice versa. If sensor 731 (comprising a camera and no markers) is used as either of sensor units 1211 or 1205, then the remaining sensor unit is preferably of type 711 or 721 (i.e. one which preferably comprises at least three markers). There are many combinations of sensor unit types which will not provide sufficient aggregate information to determine relative positioning, which will also include sensors with no corresponding measurements (i.e., a camera on one sensor, with no markers on the corresponding sensor). It will be clear to those skilled in the art which sensor unit combinations are appropriate (i.e. the desired relative positioning is locally observable).

In order to determine the relative positioning of the first (or reference or pelvis) sensor unit 1211 with respect to the patient's pelvis 1204, the positioning of at least three separate known landmarks (or reference locations) on the pelvis are identified and stored in the computing device (e.g. 511 of FIG. 5). Some examples of possible bony landmarks (or reference locations) include the pubic tubercles 1208, the ASIS points 1203, the AIIS points 1217, points along the iliac crest 1206 or bony landmarks (or reference locations) associated with the acetabulum 1216, such as the attachment point of the ligamentum teres.

Figure 11:
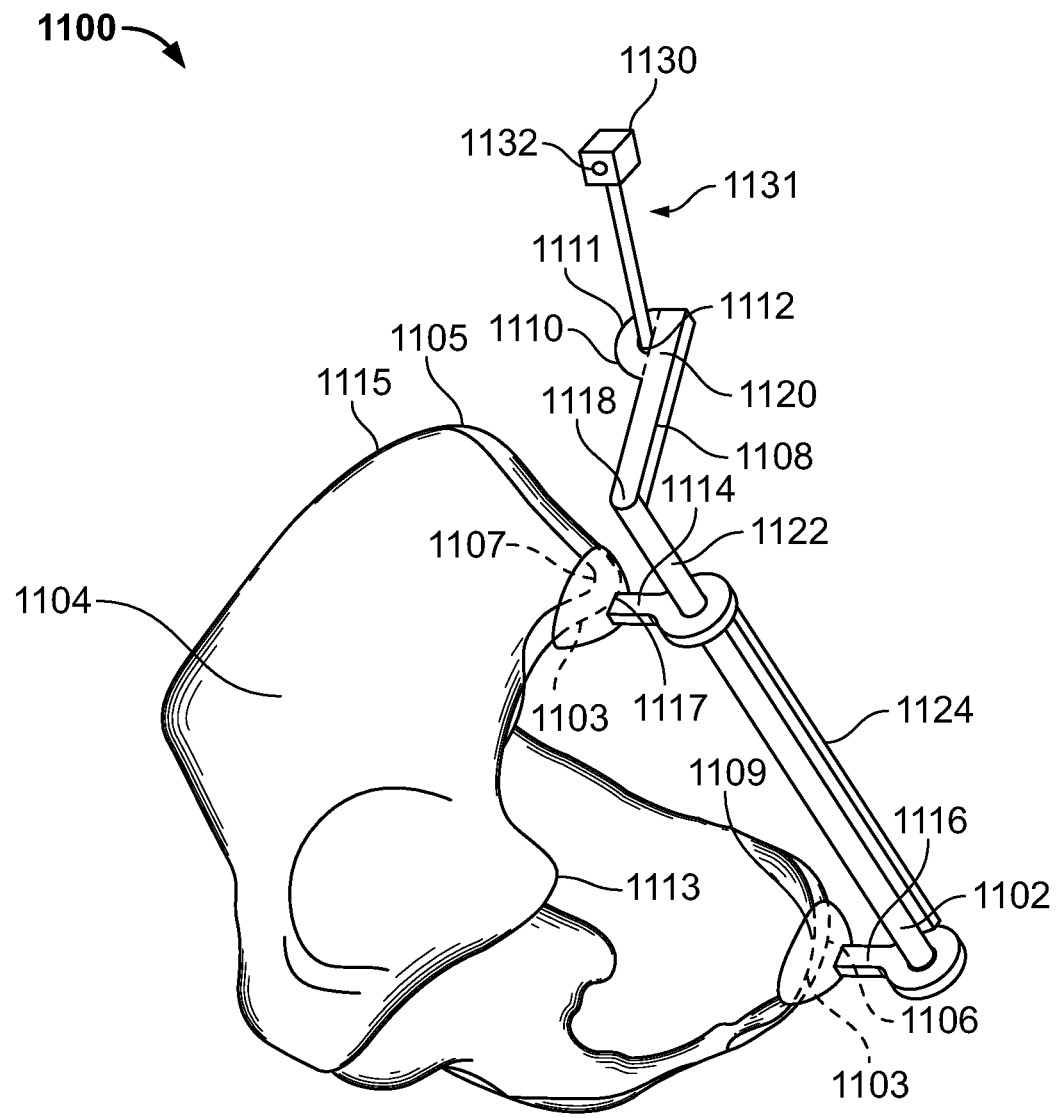
FIG. 11 is a pelvis registration device in contact with a pelvis having a sensor unit on one arm of the device, according to an embodiment.

Reference is now made to FIGS. 11 and 12. As previously discussed, in another embodiment, the pelvis registration device 1100 of FIG. 11 may be used to determine the relative positioning of a first (or reference or pelvis) sensor unit 1211 with respect to the pelvis 1204 of a patient 1207 (shown in dashed lines in FIG. 12). With the first (or reference or pelvis) sensor unit 1211 operatively connected to the pelvis 1204 of the patient 1207 (for example, as described above), the pelvis registration device 1100 is brought into contact with at least three known landmarks (or reference locations) on the pelvis. By virtue of the second sensor unit 1130 having a pre-determined relationship or measurable to each of the first, second, and third contact points 1107, 1109, and 1111, the relative positioning of the first (or reference or pelvis) sensor unit 1211 with respect to the second sensor 1130 may be used to determine the relative positioning of the pelvis bone 1204 with respect to the first (or reference or pelvis) sensor unit 1211, when the pelvis registration device 1100 is in contact with the at least three landmarks (or reference locations).

Figure 13:
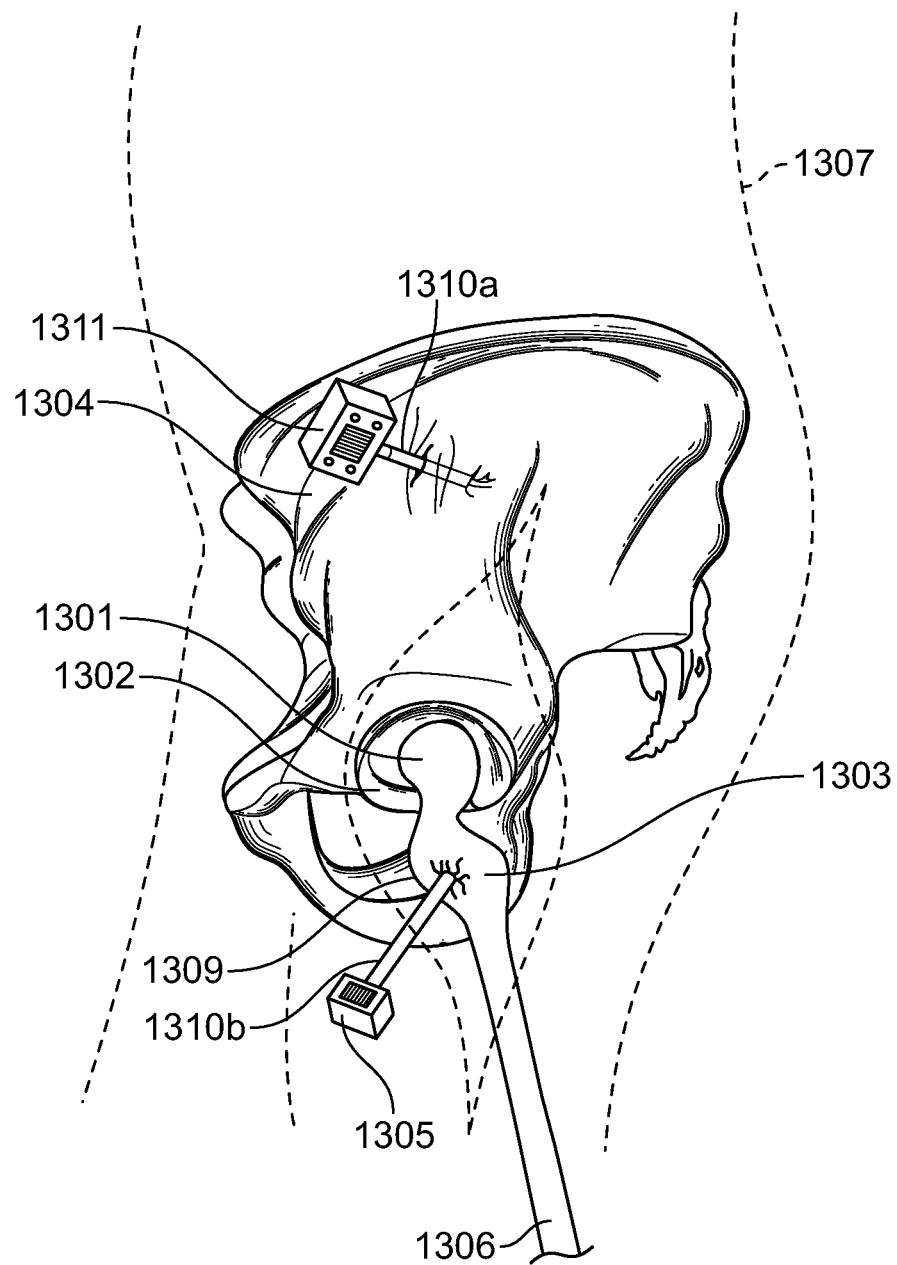
FIG. 13 is a side view of a patient's pelvis with a sensor unit attached thereto, and a femur having a sensor unit attached thereto via a bone screw or pin.

As previously discussed with reference to FIGS. 4A and 4B, in hip replacement, obtaining a desired change in leg length and offset before and after surgery may be highly desirable. Reference is now made to FIG. 13 to illustrate how a desired leg length and offset (e.g. 405*b* and 407*b*) may be effected through a hip surgery. A patient's pelvis 1304 and femur 1306 are illustrated, where the head of the femur 1301 and the region of the acetabulum 1302 are exposed within the surgical wound. In order to measure the positioning of the femur 1306 with respect to the pelvis 1304, a femur sensor unit 1305 is coupled to the femur 1306 (for example, but not limited to, using a pin having two threaded ends, one end for screwing into the femur, and the other end for mating with complementary threads on the femur sensor unit 1305, or alternatively by driving a pin into the femur and mechanically clipping the sensor onto the pin). In one embodiment, the sensor unit 1305 is coupled to the femur 1306 using a pin or bone screw 1310*b* proximate the greater trochanter 1309. In another embodiment, the sensor unit 1305 positioned so that it lies along either the mechanical or anatomical femoral axis (e.g., it may be percutaneously coupled near the distal femur).

There are several methods of measuring the changes in pre and post operative leg length and offset. In the art of hip navigation, some methods rely on determining the location of the center of rotation of the femoral head (referred to as head center). Such methods include articulating the femur or registering the femoral head and/or the acetabulum. Some methods rely on resolving a distance measurement into components representative of leg length and offset. Such methods include performing a femoral registration to determining the mechanical and/or anatomical femoral axis.

The information measured by the femur sensor unit 1305 and the first (or reference or pelvis) sensor unit 1311 is transmitted to a computing device (e.g. 511 of FIG. 5), and contains enough information to determine the relative positioning of the sensor units, and therefore the relative positioning of the femur 1306 with the pelvis 1304. This information, possibly in conjunction with information regarding the femur head center and/or the femoral axis, may be measured both before and after the surgery. A comparison of the information measured after the surgery and the information measured before the surgery (i.e., hip reduction with prosthetic components) may yield the actual changes in leg length and offset as a result of the surgery. Similarly, the anterior-posterior change in femur position may be determined. It may be said that the desired resulting leg length and offset has been effected if the actual changes in leg length and offset match the pre-determined desired changes in leg length and offset. The sensor unit options for the femur sensor unit 1305 are the same options previously discussed as available for selection as the stylus sensor unit 905 (of FIG. 9).

Figure 14:
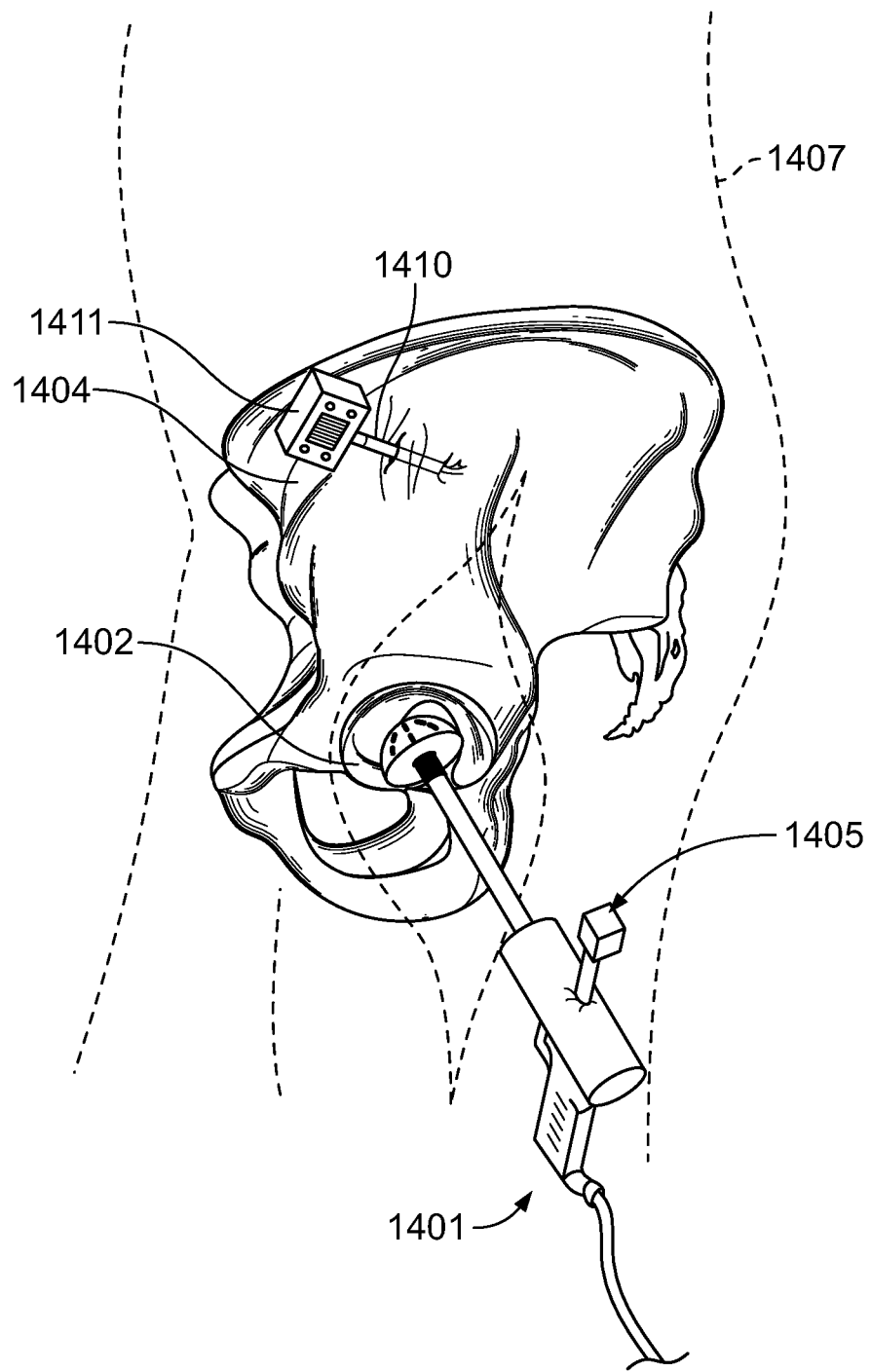
FIG. 14 is a side view of a patient's pelvis having a sensor unit attached thereto, and an acetabular reaming tool having a sensor unit attached thereto, located near the patient's acetabulum.

With reference to FIG. 14, prior to inserting the acetabular implant (e.g. 1015 of FIG. 10), the acetabulum 1402 is reamed, which entails the removal of bone, cartilage and other tissue. Reaming of the acetabulum may be performed, for example, using a reaming tool 1401. A reaming sensor unit 1405 may be coupled to the reaming tool 1401, such that the combination of the first (or reference of pelvis) sensor unit 1411 and the reaming sensor 1405 measure enough information to determine the relative positioning of the reaming tool 1401 with respect to the pelvis 1404 (this requires, for a given first (or reference or pelvis) sensor 1411, that the reaming sensor unit 1405 be selected in the same way as the femur sensor 1305). One exemplary purpose of measuring the relative positioning of the reaming tool 1401 with respect to the pelvis bone 1401 is to determine the depth, angle, etc. of the reaming procedure. The reaming sensor unit 1405 may be coupled using a pin having two threaded ends, one for mating with complementary threads on the reaming tool 1401, and another for mating with complementary threads on the reaming sensor unit 1405. Alternatively, a pin may be integrally formed with the reaming sensor unit 1405 or a marker array (see, e.g., reaming tool 2301 of FIG. 23) and may have threads complementary to threads in the reaming tool 1401. Another alternative includes forming a pin integral with the reaming tool, having threads complementary to threads in the reaming sensor unit 1405. A mechanical clip may also be used in the place of threads.

Figure 15:
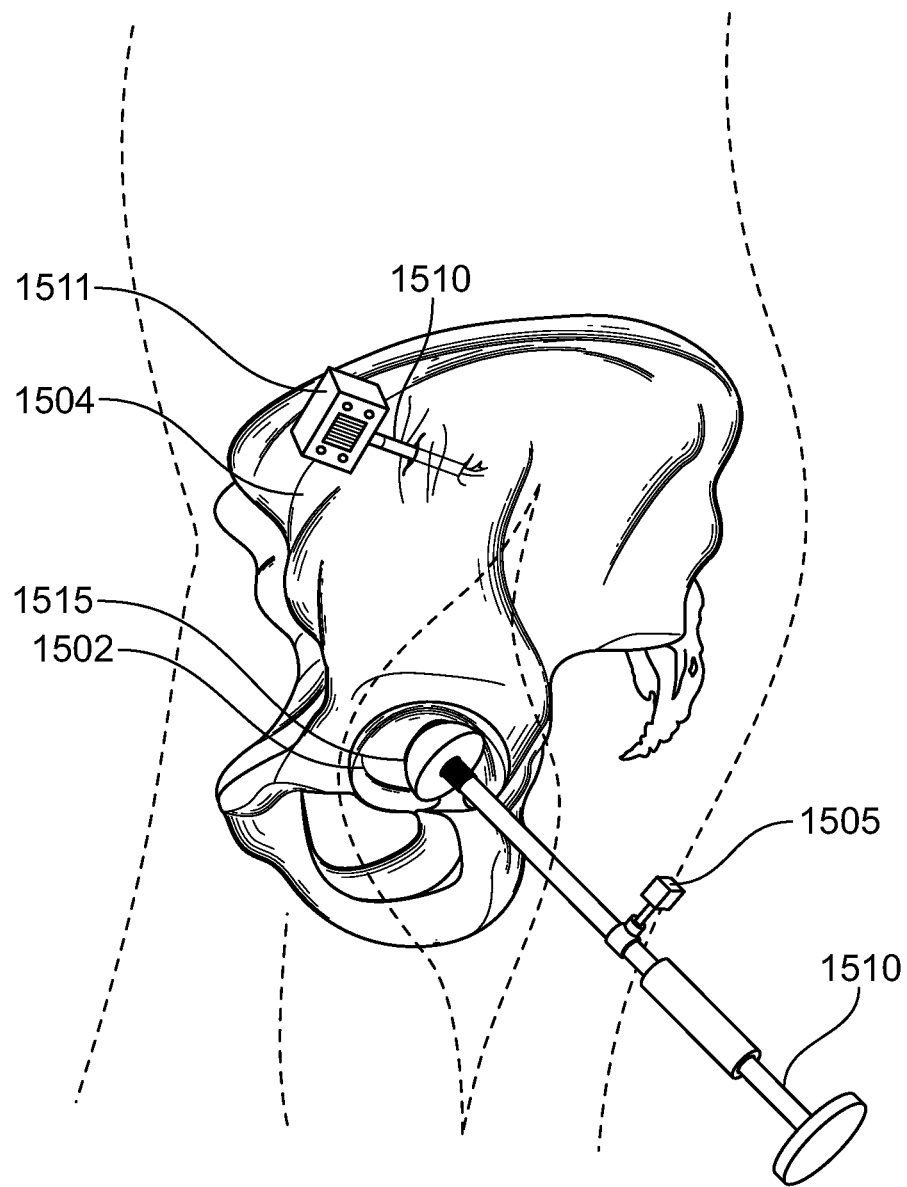
FIG. 15 is a side view of a patient's pelvis having a sensor unit attached thereto, and an acetabular implant insertion tool having a sensor unit attached thereto.

Another important factor in hip replacement is the alignment of the acetabular implant (e.g. 1015 of FIG. 10) with respect to the pelvis (particularly with reference to the angles of abduction (e.g. 332 of FIG. 3A) and anteversion (e.g. 333 of FIG. 3C)). With reference to FIG. 15, once the acetabulum 1502 has been appropriately reamed, the acetabular implant 1515 is inserted into the acetabulum 1502 using insertion tool 1510, and impacted into the acetabulum 1502 using a surgical hammer (not shown). Until insertion into the acetabulum 1502, the acetabular implant 1515 is coupled to the insertion tool 1510 in a known position (i.e. knowing the position of the tool 1510 implies knowing the position of the acetabular implant 1515). Similarly to the insertion tool 1000 of FIG. 10, a tool sensor unit 1505 is coupled to the insertion tool 1510 in a known position. Using information from sensor units 1511 and 1505 communicating with a computing device (e.g. 511 of FIG. 5), the relative positioning of the acetabular implant 1515 with respect to the pelvis 1504 may be determined. Particularly, the relative orientation of the acetabular implant 1515 with respect to the pelvis 1504 (i.e. the angles of abduction and anteversion) may be determined. Once the surgeon achieves the desired orientation of the acetabular implant 1515 with respect to the pelvis, the surgeon may secure the implant 1515 within the acetabulum 1502.

Figure 16:
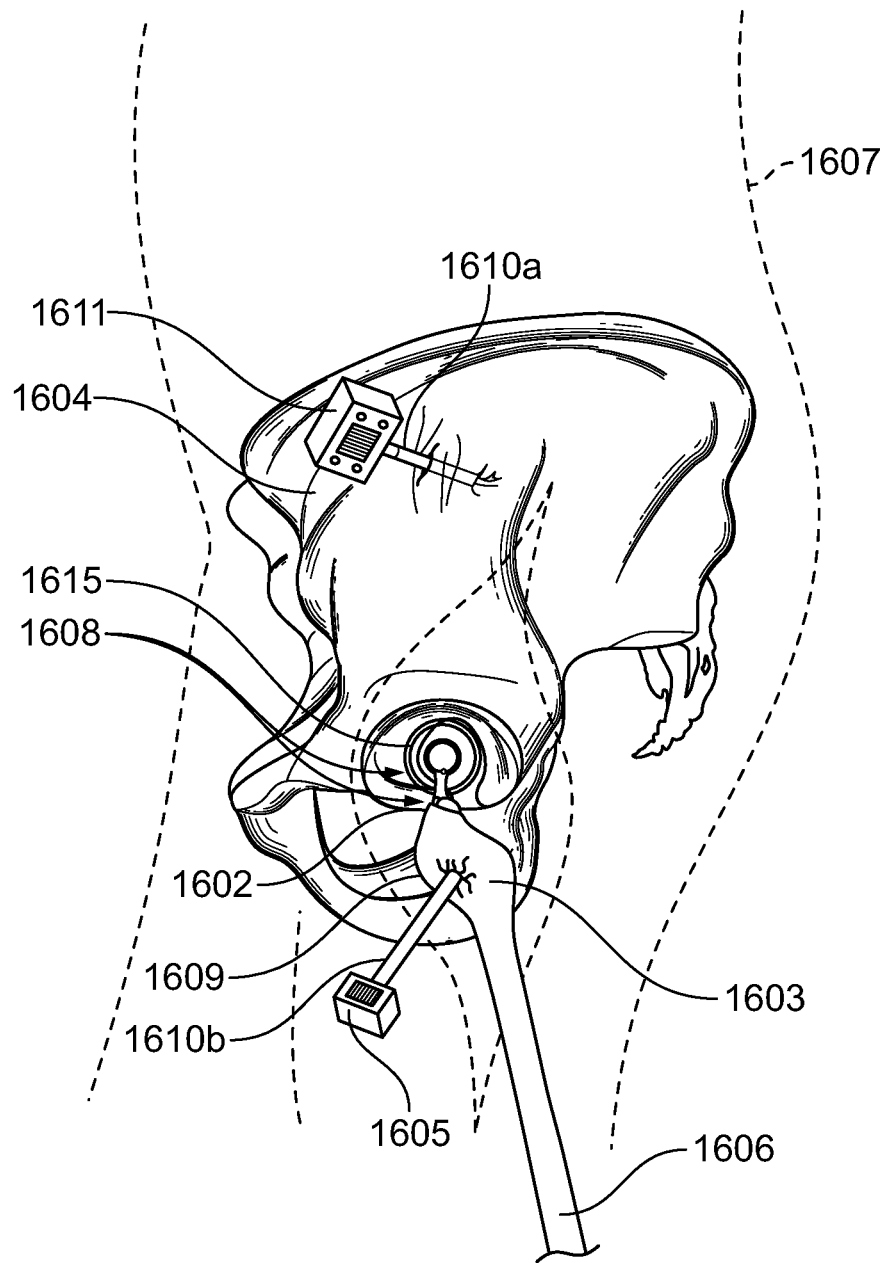
FIG. 16 is a side view of a patient's pelvis having a sensor unit attached thereto, and a patient's femur having a sensor unit attached thereto via a bone screw or pin after the prosthetic femoral components have been installed and artificial joint assembled.

Measurement of a change in leg length and offset using a plurality of sensors was previously discussed with reference to FIG. 13. To reiterate, it may be important to measure any changes in leg length or offset during the procedure intraoperatively. FIG. 16 illustrates how a desired resulting leg length and offset may be effected using a plurality of sensor units. After the implantation of the acetabular prosthetic 1615 and the femoral prosthetic 1608 (see also 208 of FIG. 2), the artificial joint is assembled, or reduced (typically first with trial components to allow for changes in sizing). The resulting positioning includes actual resulting leg length (e.g. 405*b* of FIG. 4B) and actual resulting offset (e.g. 407*b* of FIG. 4B). The change between initial reference measurement of the positioning of a point on the femur with respect to the pelvis and the positioning of the same point after the artificial joint has been assembled may be calculated. This means that the change in leg length and offset may be determined from the aggregate information from sensors 1611 (in the pelvis 1604) and 1605 (in the femur), recorded both before and after the surgery. In order to accurately determine leg length and offset, it may be advantageous to also calculate the femoral head center location, or to use a femoral positioning procedure (which may include determination of head center location) to facilitate the comparison between initial and post-reduction measurements (e.g., to guide the surgeon in restoring the initial femur orientation).

B. Stereoscopic One Active Sensor Unit Embodiment.

In the previous section, an apparatus for measuring relative positioning of tools with body parts, body parts with other body parts, and body parts with prosthetics was disclosed, in the context of, among other things, aligning and sizing prosthetic components for hip replacement surgery. In this section, one embodiment of this apparatus with similar functionality is disclosed.

In this embodiment, only one sensor unit contains optical sensors. With reference to FIG. 7E, a sensor unit 741 is shown, having a housing 743 and two optical sensors 742a, 742b, a known distance apart, unobstructed by the housing 743. The sensor unit 741 may contain other types of sensors (not shown) within the housing 743, such as accelerometers or gyroscopes. Furthermore, the sensor unit 741 may include a human interface sensor (e.g. a button) 746 (multiple human interface sensors are contemplated), interfaced to its internal processor. This sensor unit 741 may be mounted to, for example, a pelvis, via mounting bracket 744 adapted to mate with a complementary mounting bracket on the surgical tool (for example by way of a snap fit, or via mating threads). Reference is now made to FIG. 7F, in which three different marker configurations 751a, 751b, 751c are shown. Each configuration is a sensor unit which has a rigid body 752a, 752b, 752c connecting the markers 753a, 753b, 753c, respectively. The markers may emit or reflect electro-magnetic energy (e.g. visible light, IR light). In one embodiment, the type of energy that the markers emit or reflect corresponds to the type of sensor unit 741 being used. Sensor units comprising markers, but no processing or sensing capability are alternatively referred to as "arrays". Any number of markers 753 may make up a single "array" 751, depending on the positioning degrees-of-freedom that the application is required to determine (e.g. to determine all 6-DOF, at least three markers are needed per array).

Figure 17:
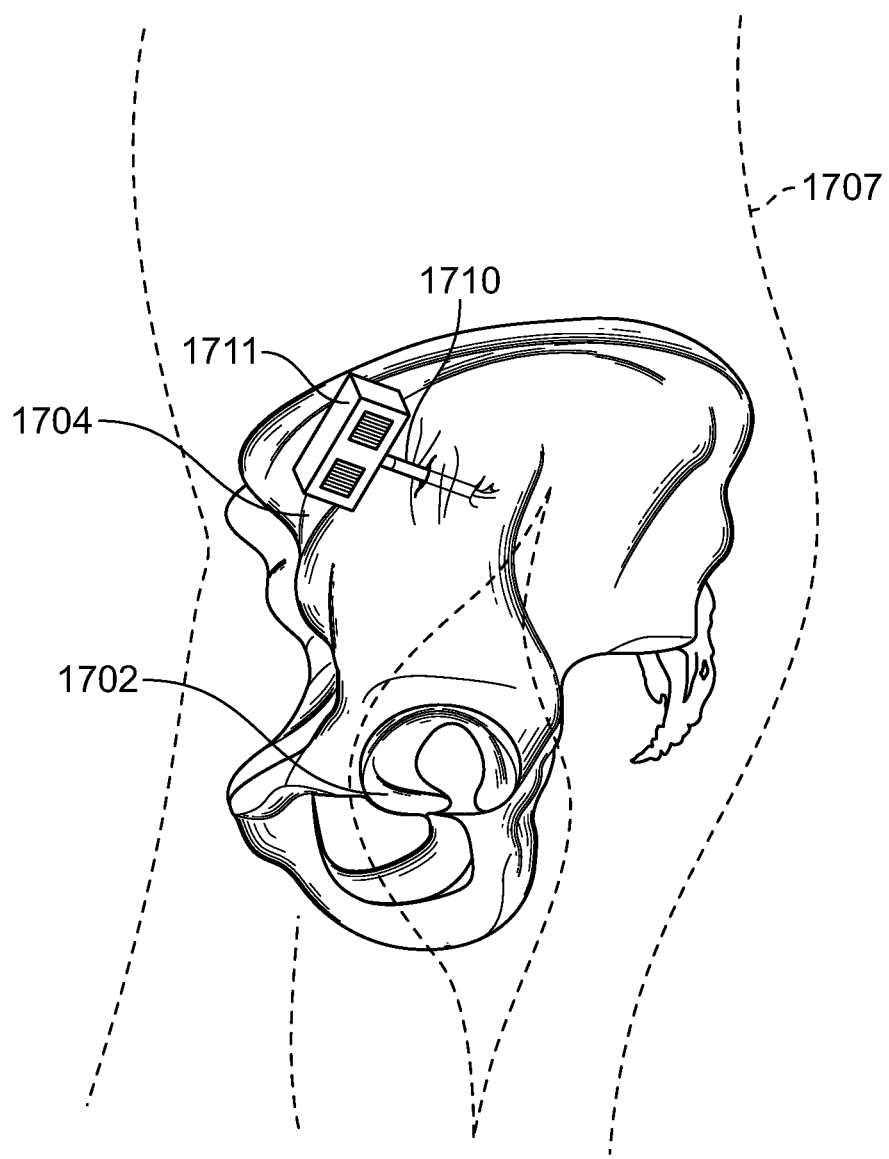
FIG. 17 is a side view of a patient's pelvis with one embodiment of a sensor unit coupled to the pelvis via the pin or bone screw in the pelvis.

With reference to FIG. 17, a sensor unit 1711 attached to a pin or bone screw 1710, which is attached to the pelvis bone 1704 of a patient 1707, is discussed. In practice, the sensor unit is preferably connected to the bone such that the field of view of the sensor unit 1711 encompasses the general area of the surgical wound.

Figure 18A:
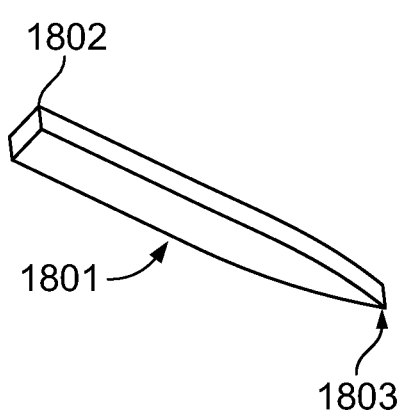
FIG. 18A is an isometric view of another stylus.
Figure 18B:
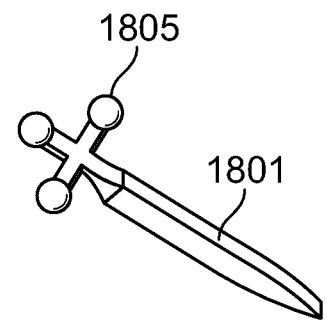
FIG. 18B is an isometric view of the stylus of FIG. 18A having a marker array coupled thereto.

FIG. 18A illustrates a stylus 1801 similar to stylus 901 of FIG. 9A. FIG. 18B illustrates the stylus of FIG. 18A with a marker array 1805 coupled thereto. Array 1805 comprises three markers (but may comprise more) as 6-DOF positioning will be required in the exemplary embodiment.

Figure 19:
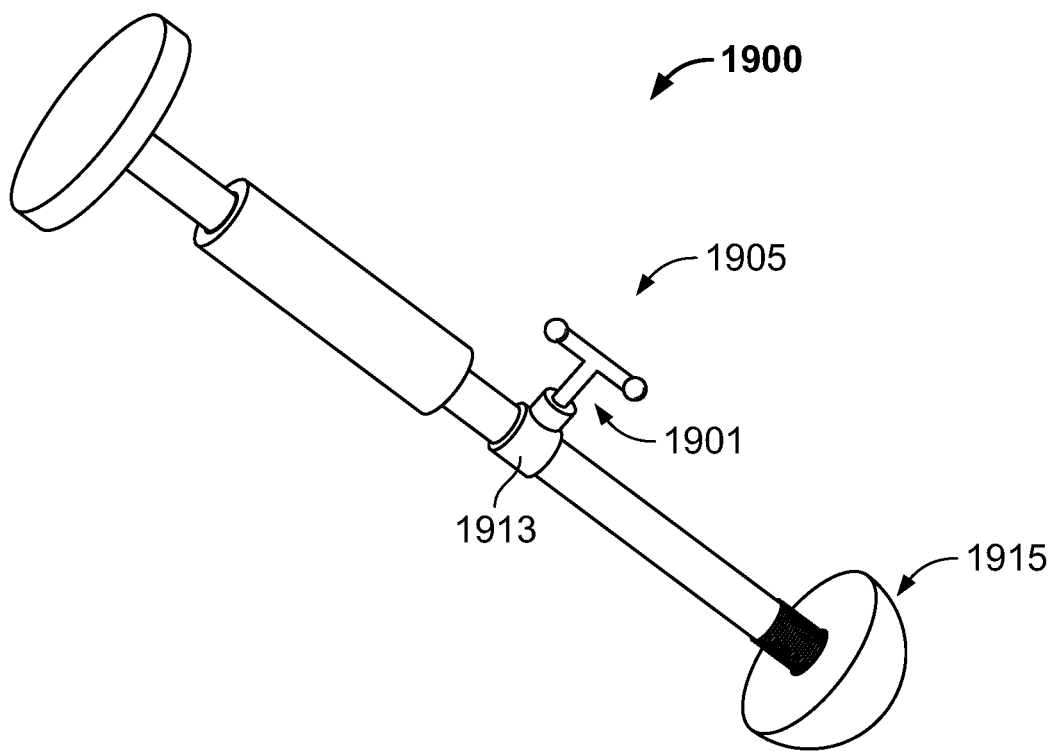
FIG. 19 is an isometric view of an acetabular implant insertion tool with a marker array attached thereto.

FIG. 19 illustrates an acetabular cup insertion tool 1900 similar to acetabular cup insertion tool 1000 of FIG. 10. Insertion tool 1900 comprises a marker array 1905 coupled to it via a coupler 1913, for example, using similar coupling techniques as described above. The array 1905 preferably includes at least two marker points (only 2 points are needed where the proper positioning of the acetabular cup (or implant) depends only on two orientation angles: abduction 332 (FIG. 3A) and anteversion 333 (FIG. 3C)).

Figure 20:
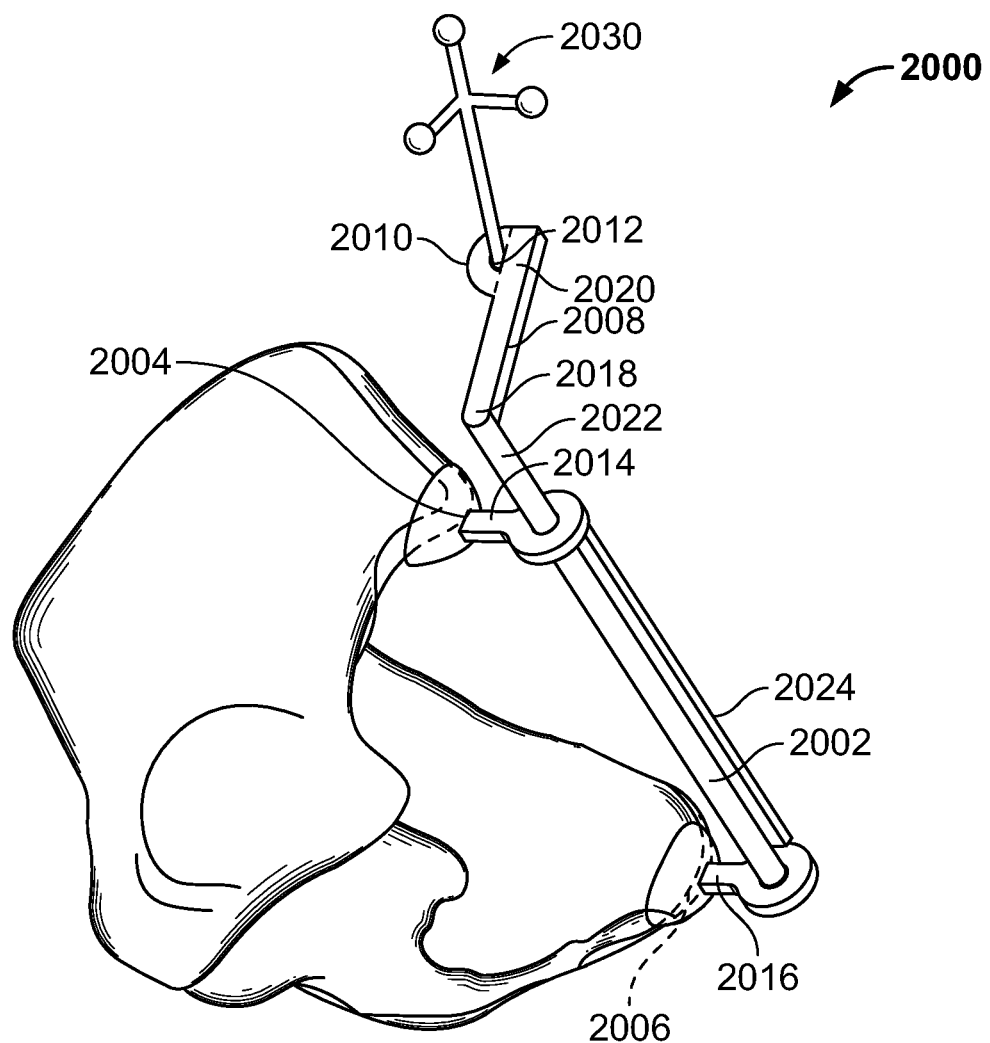
FIG. 20 is another pelvis registration device having a marker array on one arm of the device, shown in contact with a pelvis.

In FIG. 20, an embodiment of a pelvis registration device 2000 is illustrated. This device is identical to the pelvis registration device 1100 of FIG. 11, with the exception that a marker array 2030, preferably comprising at least three markers, is used instead of sensor unit 1130. In one embodiment, device 2000 is used for the same purpose as device 1100 (FIG. 11). It may be preferable, where device 2000 is used, to have a human interface sensor (e.g. a button) on the first (or reference or pelvis) sensor unit (e.g. 1711 of FIG. 17) instead of on the device 2000 so that device 2000 may be free of a communication channel.

Figure 21:
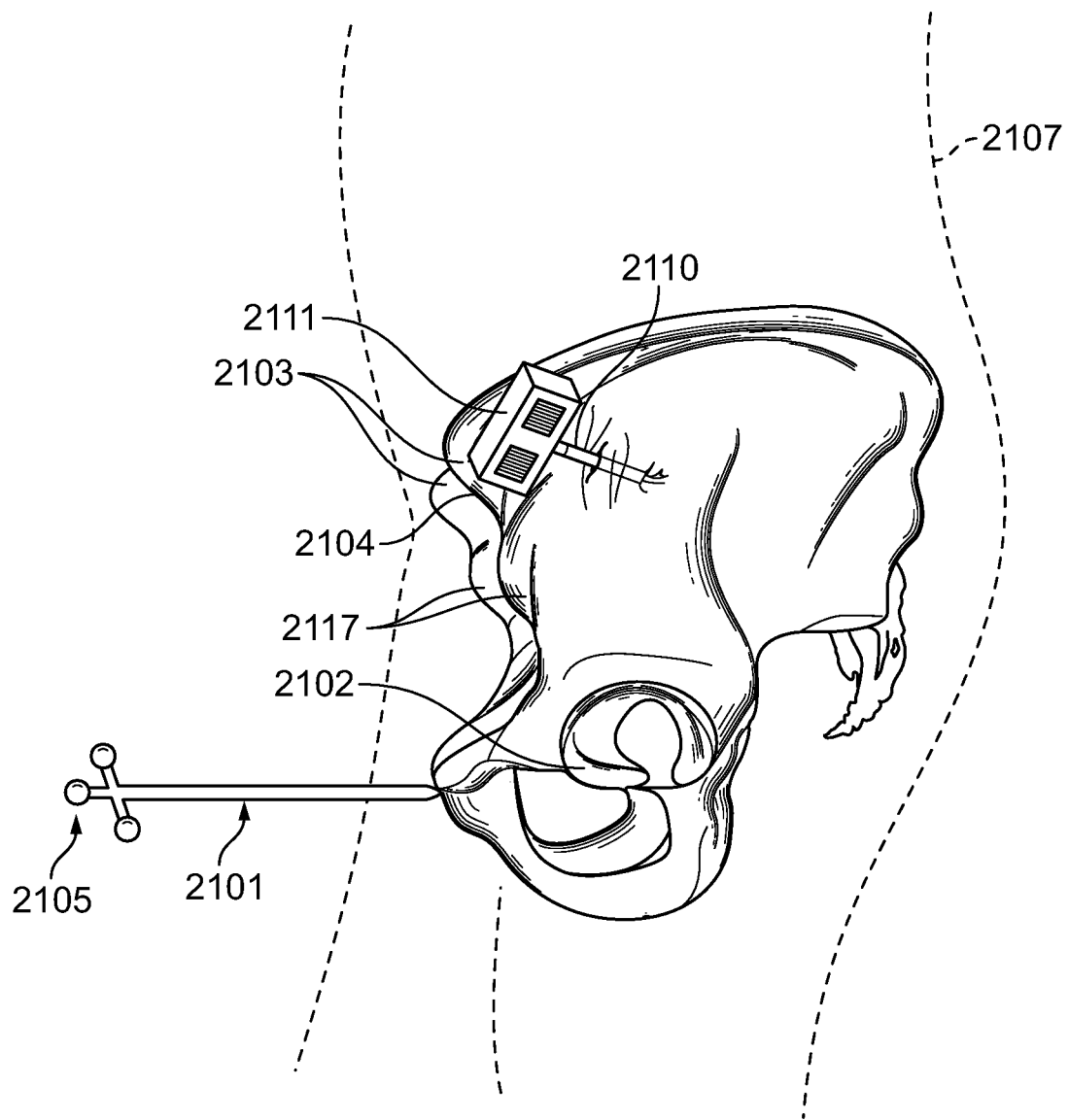
FIG. 21 is a side view of a patient's pelvis having a sensor unit attached thereto, and a stylus, having a marker array connected thereto, contacting a landmark on the pelvis.

In FIG. 21, a system is illustrated such that the location of bony landmarks (or reference locations) on the pelvis may be determined with respect to a first (or reference or pelvis) sensor unit 2111. The stylus 2101 and array 2105 may be used to contact various landmarks (or reference locations) on the pelvis (e.g. the ASIS points 2103 and the AIIS points 2117). When in contact with a bony landmark (or reference location), a button (not shown) on the sensor unit 2111 may be pushed in order to indicate that the stylus 2101 is in contact with a landmark (or reference location). In one embodiment, at least three landmarks (or reference locations) are contacted with their locations determined by measuring the array 2105 positioning using the sensor unit 2111. In another embodiment, landmarks along the femur are recorded where a femoral registration is necessary.

In an alternative embodiment, a pelvis registration device 2000 of FIG. 20 may be used to determine the bony landmarks (or reference locations) on a pelvis with respect to a first (or reference or pelvis) sensor unit 2111 by simultaneously contacting at least three landmarks (or reference locations).

Figure 22:
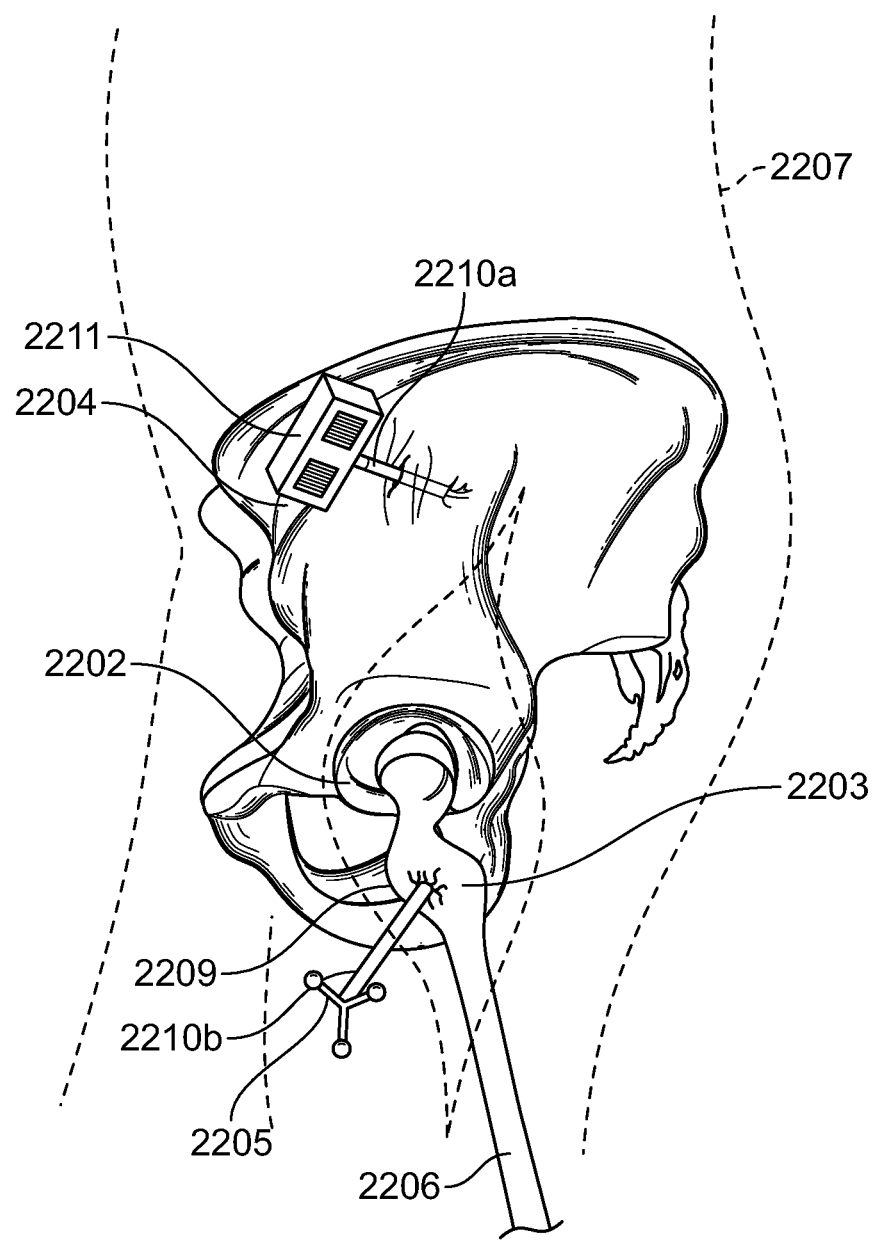
FIG. 22 is a side view of a patient's pelvis with one embodiment of the sensor unit attached thereto, and a patient's femur having a marker array attached thereto via bone screw or pin.

As previously discussed, measuring the change from pre-operative leg length (e.g. 405a of FIG. 4A) and offset (e.g. 407a of FIG. 4A) to leg length (e.g. 405b of FIG. 4B) and offset (e.g. 407b of FIG. 4B) after prosthetics have been implanted may be important. With reference to FIG. 22, in the present embodiment, a reference pre-operative leg length (e.g. 405a) and offset (e.g. 407a), may be measured by operatively connecting an array 2205 to the femur 2206 using the pin or bone screw 2210b (as described above). The first (or reference or pelvis) sensor unit 2211 may be used to determine the pre-operative reference positioning of the femur 2206 with respect to the pelvis 2204 by tracking the markers on array 2205.

Figure 23:
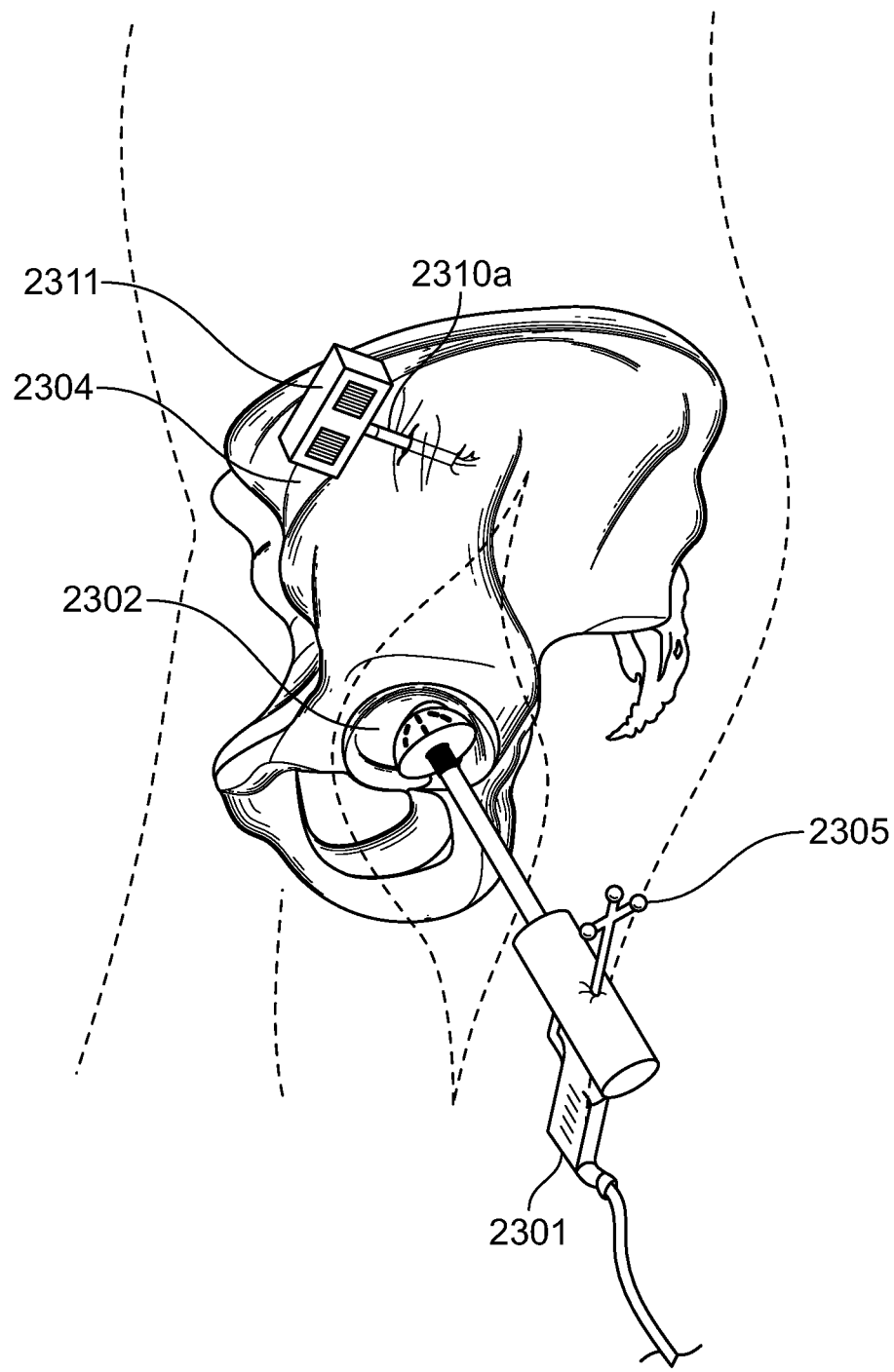
FIG. 23 is a side view of a patient's pelvis having one embodiment of a sensor unit attached thereto, and an acetabular reaming tool having a marker array attached thereto.

Reaming of the acetabulum according to the present embodiment is now discussed with reference to FIG. 23. Reaming is performed during the preparation of the acetabulum for prosthetic implantation. An exemplary tool 2301 is shown, and coupled to it is an exemplary array 2305, preferably with at least three markers, such that the first (or reference or pelvis) sensor unit 2311 is able to measure the positioning of the reaming tool by way of localizing each marker of the array 2305. The array 2305 may be coupled to the tool 2301, for example, according the coupling options as described above.

Figure 24:
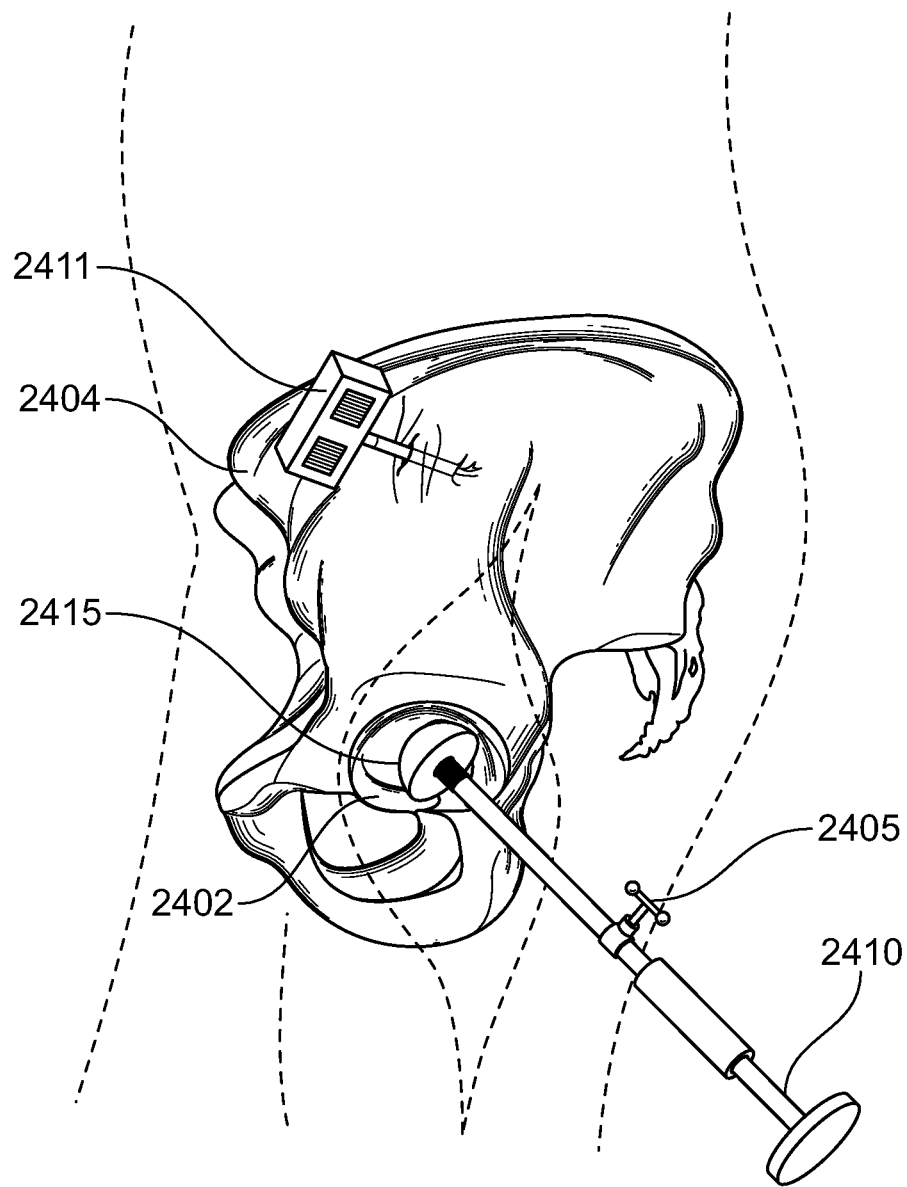
FIG. 24 is a side view of a patient's pelvis having one embodiment of a sensor unit attached thereto, and an acetabular implant insertion tool having a marker array attached thereto.

Another important consideration during hip surgery that has been discussed herein is the orientation of the acetabular implant component with respect to the pelvis. With reference to FIG. 24, an exemplary system used to determine the relative orientation of an acetabular implant 2415 with respect to the first (or reference or pelvis) sensor 2411 is discussed. The first (or reference or pelvis) sensor unit 2411 is able to track the array 2405 optically, and measure sufficient information to determine the relative position of the array 2405. The array 2405 is coupled to the insertion tool 2410 in a known (or pre-determined) relative position (for example, as described above), and the insertion tool 2410 is coupled to the acetabular implant 2415 in a known relative position. The acetabular cup may be coupled to the corresponding surgical insertion tool, for example, via mating threads. Consequently, the first (or reference or pelvis) sensor unit 2411, which is coupled (for example, as described above) to the pelvis in a known relationship to a pre-determined geometry of the pelvis 2404 (e.g. measured from a pre-operative scan of the pelvis), enables the computing device (not shown in FIG. 24) to determine the position of the acetabular implant 2415 relative to the pelvis' geometry.

Figure 25:
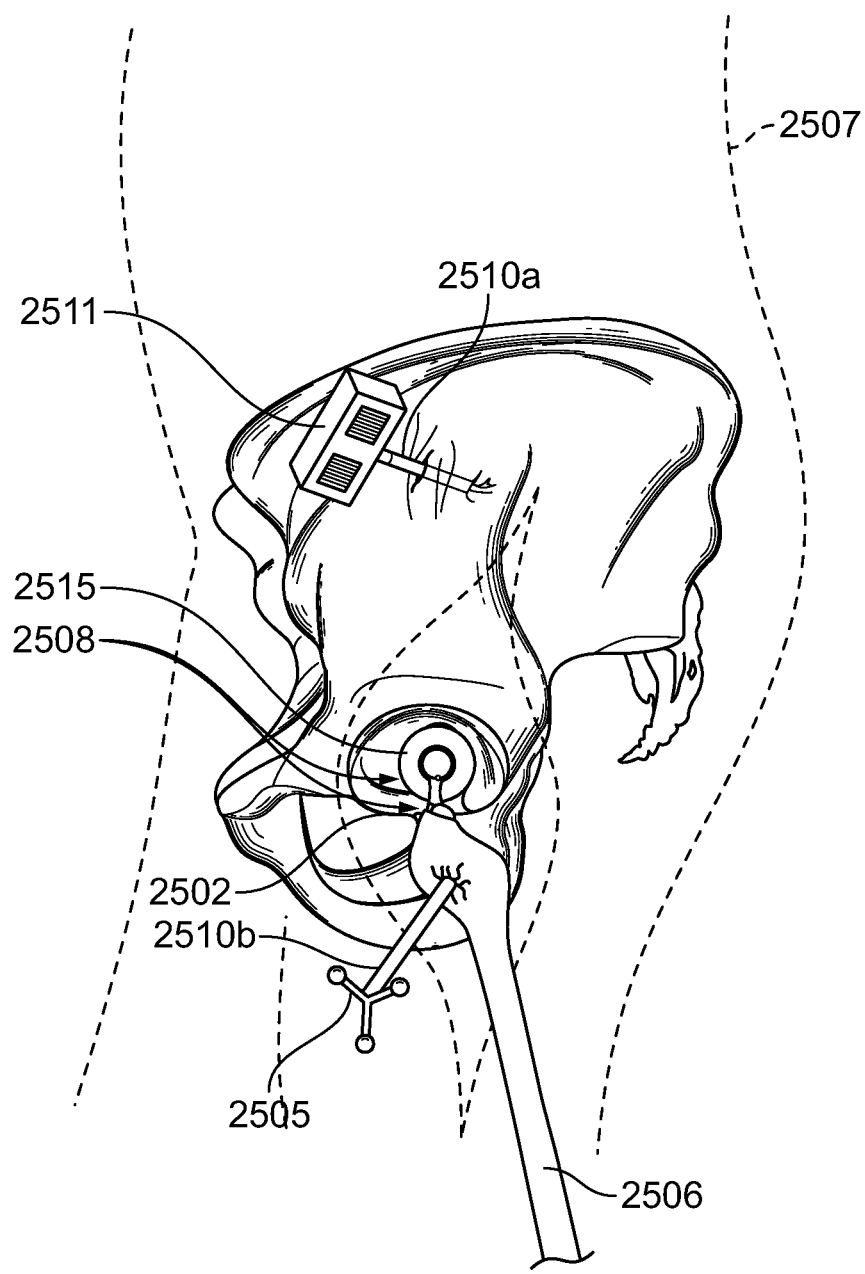
FIG. 25 is a side view of a patient's pelvis having one embodiment of a sensor unit attached thereto, and a patient's femur having a marker array attached thereto via bone screw or pin after the prosthetic femoral components have been installed.

Reference is now made to FIG. 25, which illustrates how the present embodiment may be used to measure leg length (e.g. 405b of FIG. 4B) and offset (e.g. 407b of FIG. 4B) after the artificial joint has been assembled (typically done with trial components to determine the proper sizing before implanting the permanent components). The first (or reference or pelvis) sensor unit 2511 may be used to measure the relative positioning of the marker array 2505 (marker array 2505 will typically be the same as marker array 2205 of FIG. 22). A comparison of the relative positioning of marker array 2505 (after surgery) with the relative positioning of marker array 2205 (before the surgery) may be performed in order to calculate the change in leg length and offset once the artificial joint (combination of 2508 and 2515) has been assembled.

III. Method of Use

Figure 26:
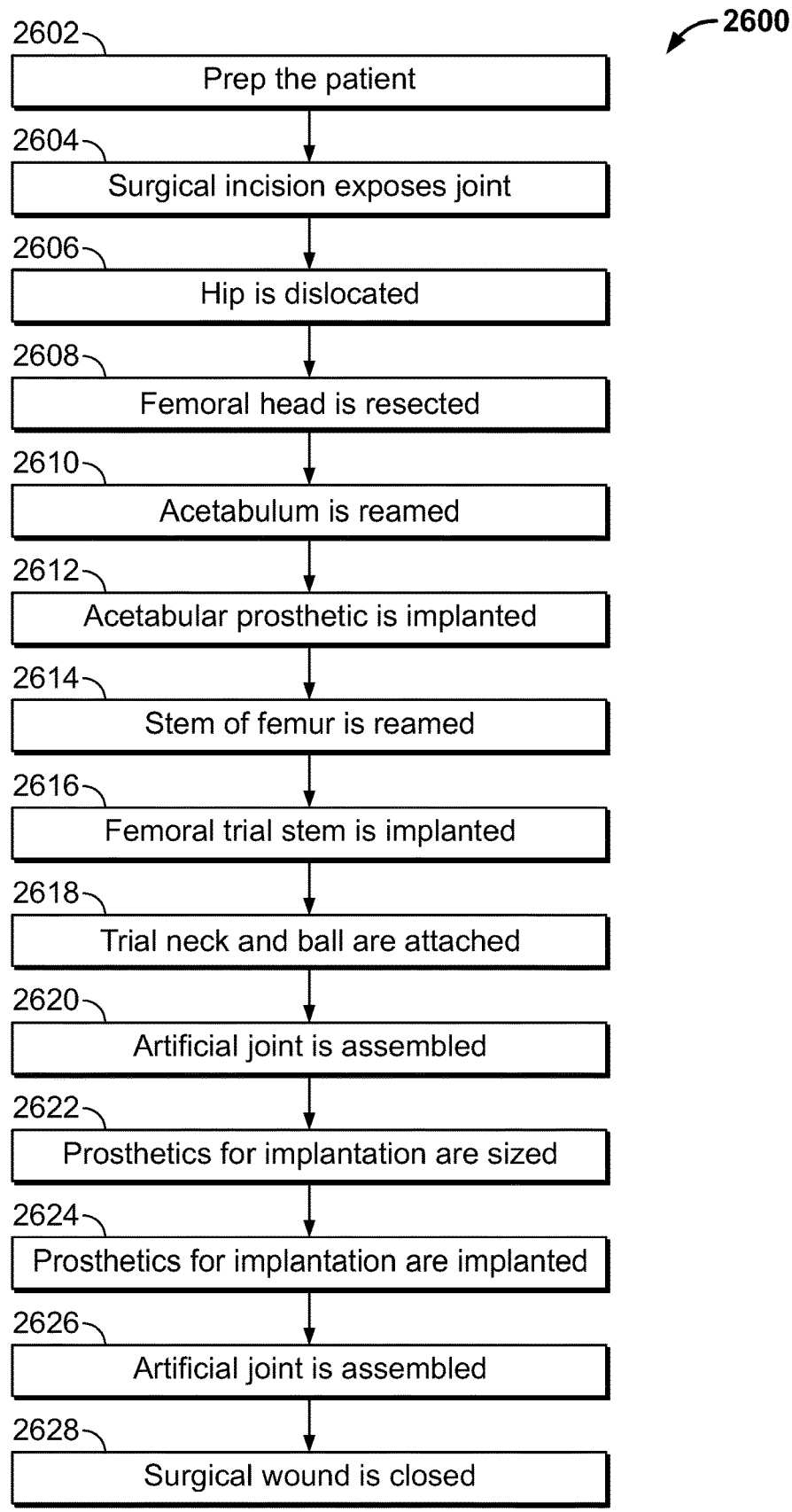
FIG. 26 is a flow chart of a method for performing THA according to one embodiment.

Reference is now made to FIG. 26, in which an example method for a hip replacement procedure is presented, in schematic form, and to FIGS. 1 and 2, in order to provide context for the methods and systems described herein. At block 2602, the patient is prepared for surgery (i.e. cleaning, sedating, positioning, etc.). The surgical procedure starts with an incision, at block 2604, which ultimately exposes the hip joint 100 (after getting through several different layers of tissue). At block 2606, the patient's hip joint is dislocated, such that the femoral head 108 no longer resides in the acetabulum 102. In total hip replacement, the head of the femur 108 is removed (or resected) as block 2608 suggests (the femoral head 108 may be resected before dislocating the joint at block 2606). Typically, the next aspect of the surgical procedure involves reaming of the acetabulum 102 (block 2610) in order prepare the acetabulum 102 for insertion of the acetabulum implant 220. Once the acetabulum is reamed, the prosthetic acetabular implant 220 may be implanted as per block 2612. The femur also requires reaming (block 2614) so that the femoral prosthetic component 211 (comprising a femoral ball and stem) may be received into the femur 210. Femoral reaming may be performed using a femoral broach. Once reaming of the femur 210 is complete, a trial femoral prosthetic may be implanted into the femur, as per block 2616. At block 2618, trial neck and ball components are used to assemble the trial femoral implant. At block 2620, the artificial joint (combination of 208 and 211) is assembled, and the patient's joint range of motion is may be tested. If the trial components do not fit well, then new trial neck and ball (of different sized) may be attached and tested until a desired fit is achieved. Once the desired fit is achieved, then actual prosthetics for implantation (as opposed to trial ones) are sized accordingly at block 2622. At block 2624, the trial femoral components are replaced by the actual prosthetics and are implanted. At block 2626, the artificial joint is assembled, and the fit of the joint is once again verified. Finally, at block 2628, the surgical wound is closed.

Figure 27:
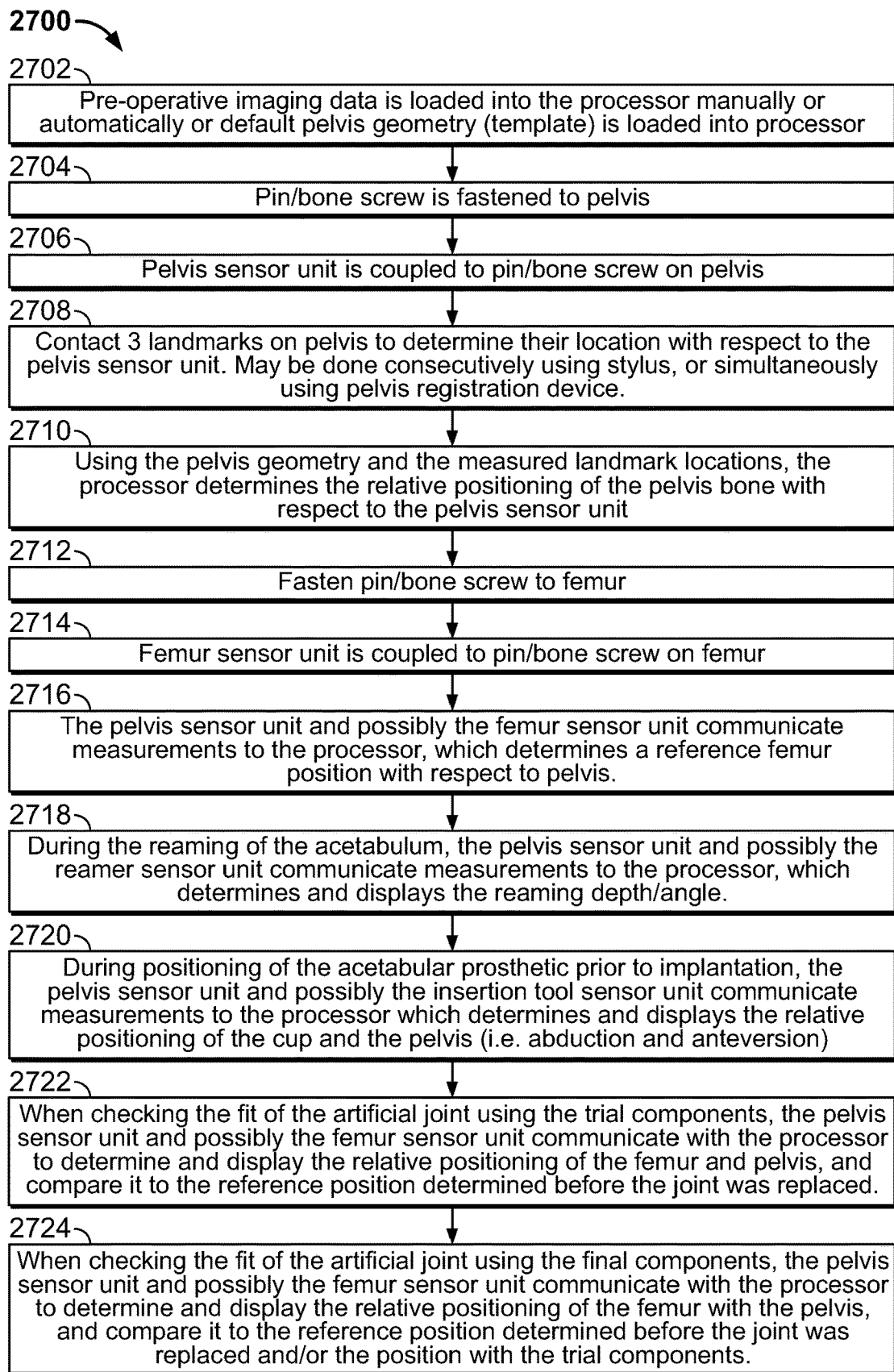
FIG. 27 is a flow chart of a method for using the system including a surgical navigation tool, in hip replacement procedures in accordance with an embodiment.

Reference is now made to FIG. 27, which illustrates a method 2700 outlining how the disclosed systems may be used in the context of a hip replacement surgery. The method 2700 of FIG. 27 is typically performed contemporaneously with the method 2600 of FIG. 26; accordingly, continuing reference is made to FIG. 26. At block 2702, which may be performed at any time prior to block 2710, but will typically be done in preparation for surgery, a pre-determined geometry of the pelvis of the patient undergoing the operation is input into the computing device. Since every patient's pelvis geometry is unique, this step is performed so that pelvic landmark locations (or reference locations) are correlated to the actual pelvis geometry by a computing device (e.g. 511 of FIG. 5). If the patient's pelvis geometry obtained via any suitable medical imaging procedure is unavailable, a default pelvis template may be used. Once the patient has been prepped (e.g. block 2602), the first (or reference or pelvis) sensor unit (e.g. 1211 of FIG. 12) is operatively connected to the pelvis (e.g. 1204 of FIG. 12), which may be achieved, for example, by connecting the first (or reference or pelvis) sensor (e.g. 1211) to a pin or bone screw (e.g. 1210) rigidly attached to the pelvis (e.g. 1204) at blocks 2704 and 2706.

At block 2708, which occurs subsequent to block 2602 (patient prepping) and prior to block 2606 (hip joint dislocation), and involves contacting at least three pelvic landmarks (or reference locations) using either a stylus and second sensor unit combination (e.g. 1201 and 1205 of FIG. 12 or 2101 and 2105 of FIG. 21) or a pelvis registration device (e.g. 1100 or 2000), and measuring the position of the landmarks (or reference locations) with respect to the first (or reference or pelvis) sensor unit (e.g. 1211). At block 2710, the locations of the landmarks (or reference locations) are correlated by a computing device (e.g. 511 of FIG. 5) with the preoperative imaging data or the default template geometry of step 2702, so that the relative positioning of the pelvis sensor unit (e.g. 1211) with respect to the pelvis (e.g. 1204) may be determined.

At blocks 2712 and 2714, a sensor unit or marker array (e.g. 1605 of FIG. 16 or 2205 of FIG. 22) is operatively connected to the patient's femur (e.g. 1606), for example, as described above. The operative connection may be done via a pin or bone screw (e.g. 1610b) fastened to the femur (e.g. 1606). At block 2716, the first (or reference or pelvis) sensor unit (e.g. 1611 of FIG. 16 or 2211 of FIG. 22) and possibly the femur sensor unit or marker array (e.g. 1605 or 2205) communicate with the computing device (e.g. 511 of FIG. 5) such that an original relative femur positioning is determined and stored while the joint is still intact. At this point in the hip replacement procedure, block 2606 (hip dislocation) may be performed.

At block 2718, which is typically performed contemporaneously with block 2610 of the hip replacement procedure (acetabular reaming), the first (or reference or pelvis) sensor unit (e.g. 1611 or 2211) and possibly the reamer sensor unit or marker array (e.g. 1405 of FIG. 14 or 2305 of FIG. 23) communicate with the computing device (e.g. 511 of FIG. 5) such that through their respective measurements, the relative positioning of the reaming tool (e.g. 1401 of FIG. 14 and 2301 of FIG. 23) and pelvis during reaming is determined and displayed to the surgeon, for example via a display (e.g. 514 of FIG. 5). This positioning data may be formatted to indicate a reaming angle and a reaming depth. Furthermore, this data may be saved to a database (e.g. 516 of FIG. 5).

At block 2720, which is performed in conjunction with block 2612 of the hip replacement procedure (implantation of acetabular implant), the first (or reference or pelvis) sensor unit (e.g. 1511 and 2411) and possibly the insertion tool sensor unit or marker array (e.g. 1505 of FIG. 15 or 2405 of FIG. 24) communicate with the computing device (e.g. 511 of FIG. 5) such that through their respective measurement, the relative positioning of the acetabular implant (e.g. 1515 of FIG. 15 and 2215 of FIG. 22) and pelvis (e.g. 1504 and 2404) during alignment is determined and displayed to the surgeon, for example, via a display (e.g.

514 of FIG. 5). This positioning data may be formatted to indicate angles of abduction and anteversion (e.g. 332 and 333 of FIGS. 3A and 3C, respectively). Furthermore, this data may be saved to a database (e.g. 516 of FIG. 5). Once the positioning is to the surgeon's satisfaction, the acetabular implant (e.g. 1515 of FIG. 15 and 2215 of FIG. 22) may be implanted (block 2612).

Blocks 2614, 2616, 2618, and 2620 may be specific to total hip replacement. Those skilled in the art will appreciate that corresponding steps in other types of hip replacement procedures or other types of orthopaedic surgeries, generally, may be appropriate depending on the nature of the surgery being performed.

At block 2722, when checking the fit of the joint with trial prosthetics (blocks 2618 and 2620), the first (or reference or pelvis) sensor unit (e.g. 1611 of FIG. 16 and 2511 of FIG. 25) and possibly the femur sensor unit or marker array (e.g. 1605 or 2505) communicate with the computing device (e.g. 511 of FIG. 5) such that the change in trial femur positioning is determined based on the stored reference femur position and the new measurements. This information may be displayed to the surgeon, for example, via a display (e.g. 514 of FIG. 5), preferably in the form of change in leg length (i.e. 405*b* minus 405*a*) and change in offset (i.e. 407*b* minus 407*a*). The surgeon may use this information to size the femoral prosthetics (step 2622). Furthermore, this information may be stored in a database (e.g. 516 of FIG. 5).

Once the femoral prosthetics for implantation are selected, they are implanted, as per block 2624, and the artificial joint is assembled, as per block 2626. At this point, it is possible to verify the positioning of the femur with respect to the joint, as suggested at block 2724. The first (or reference or pelvis) sensor unit (e.g. 1611 of FIG. 16 and 2511 of FIG. 25) and possibly the femur sensor unit or marker array (e.g. 1605 or 2505) communicate with the computing device (e.g. 511 of FIG. 5) such that the change in actual femur positioning may be determined based on the stored reference femur position and/or the trial femur measurement and the new measurements. This information is displayed to the surgeon, for example, via a display (e.g. 514 of FIG. 5), preferably in the form of change in leg length (i.e. 405*b* minus 405*a*) and change in offset (i.e. 407*b* minus 407*a*). The surgeon may use this information to verify that the resulting joint alignment is satisfactory. Furthermore, this information may be stored in a database (e.g. 516 of FIG. 5). At this point, the surgical wound may be closed (block 2628).

Figure 28A:
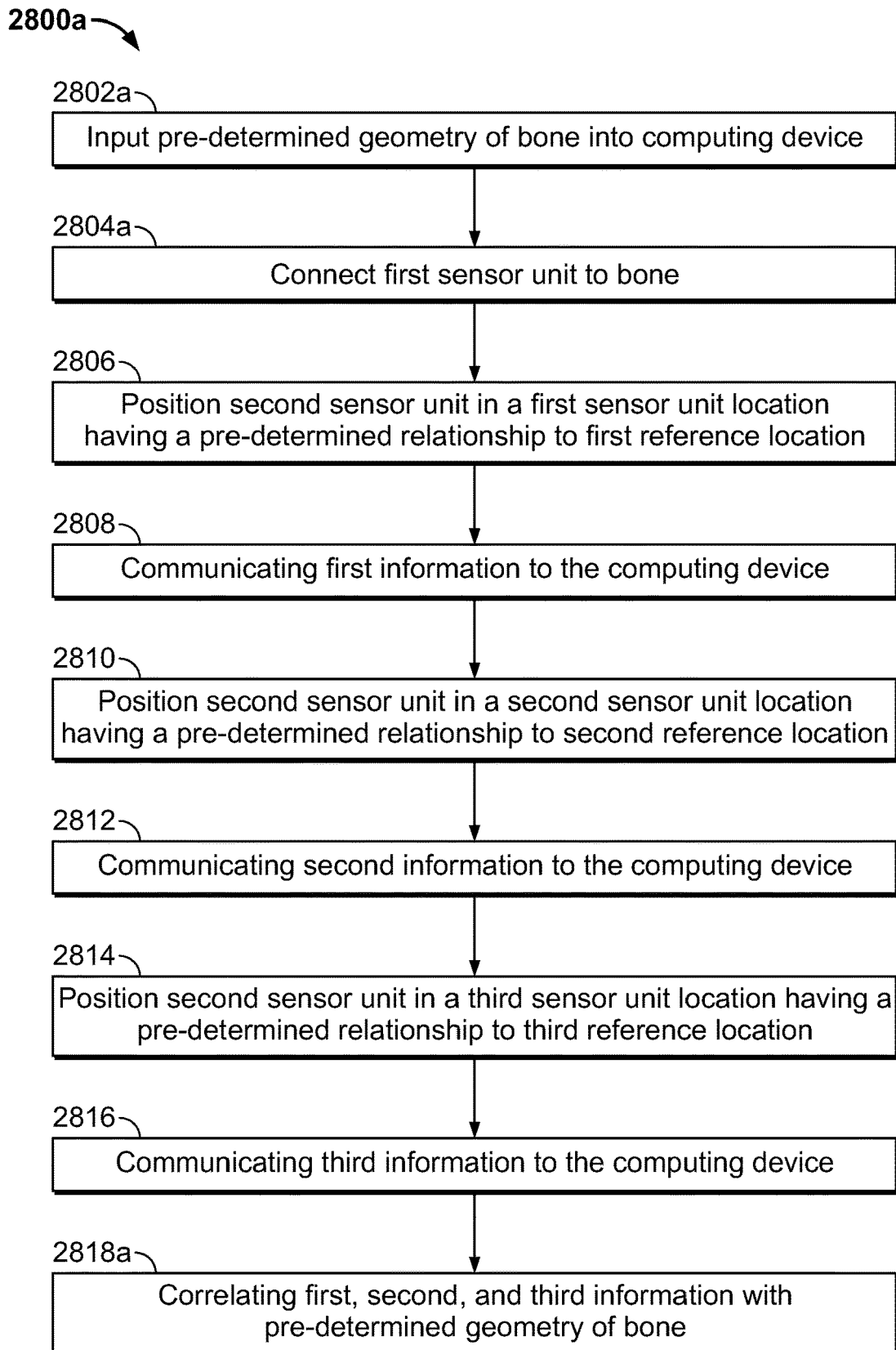
FIG. 28A is a flow chart of a method for determining a relative position of a first sensor unit with respect to a pre-determined geometry of a bone in accordance with one embodiment.
Figure 28B:
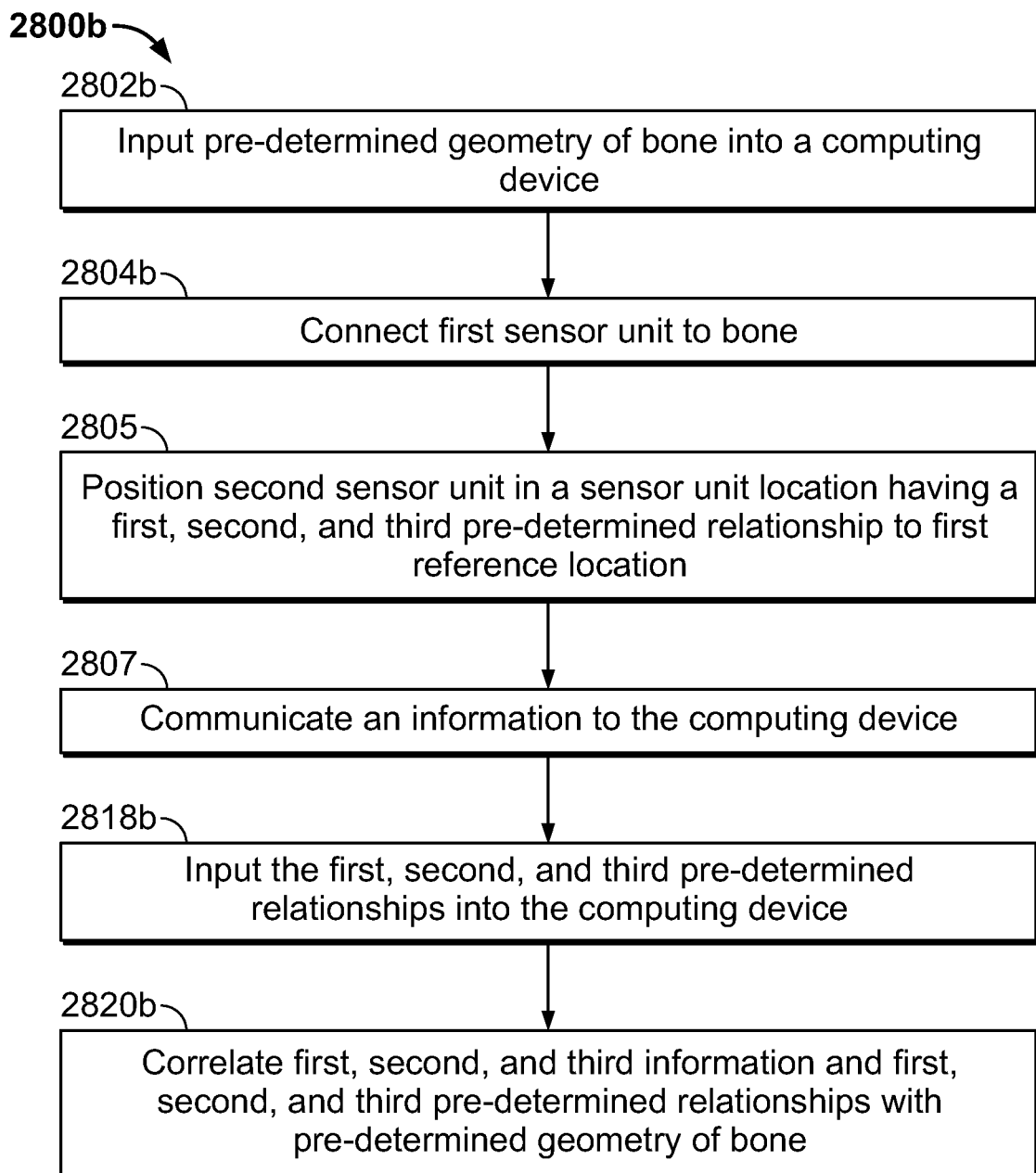
FIG. 28B is a flow chart of a method for determining a relative position of a first sensor unit with respect to a pre-determined geometry of a bone in accordance with another embodiment; and, FIG. 29 is a flow chart of a method for determining the relative positioning of a bone and a rigid body in accordance with one embodiment.

With reference to FIGS. 28A and 28B, method 2800*a*, 2800*b* for determining a relative position of a first sensor unit with respect to a pre-determined geometry of a bone is described. Reference will also be made to FIGS. 11 and 12. According to this exemplary embodiment, the bone is a patient's pelvis (e.g. 1104 and 1204). The method of FIG. 28A is applicable where, for example, a stylus (e.g. 1201) having a second sensor unit (e.g. 1205) is used to gather positioning information of bony landmarks (or reference locations) on the bone.

Specific reference is now made to FIGS. 28A and 12. At block 2802*a*, a pre-determined geometry of the bone (e.g. pelvis 1204) is input into a computing device (e.g. 511 of FIG. 5). The geometry may be pre-determined by taking measurements based on a pre-operative scan (e.g. x-ray, CT scan, and MRI) of the patient and may be input using an input device, such as a keyboard or mouse, in communication with the computing device (e.g. 511 of FIG. 5). Where a pre-operative scan of the patient (or other suitable data from which the geometry of the bone may be pre-determined or measured) is unavailable, a default bone template (e.g. pelvis template) may be used.

At block 2804*a*, a first (or reference) sensor unit 1211 is operatively connected to the bone 1204, for example, as described above. This connection may be achieved, for example, by fixing a pin or bone screw 1210 to the bone 1204 and attaching the reference sensor unit 1211 to the pin or bone screw 1210 in a known orientation.

At block 2806, a second sensor unit 1205 is positioned in a first sensor unit location having a pre-determined relationship to a first reference point. In the embodiment illustrated in FIG. 12, a stylus 1201 having the second sensor unit 1205 attached thereto in a known position is used to contact a pubic tubercle 1208 (a first reference location). While maintaining contact between the end of the stylus 1201 and the first reference location (and therefore maintaining the second sensor unit 1205 in a first sensor location), first information relating to the relative positioning of the second sensor unit (and therefore the first reference location) with respect to the reference sensor unit 1211 is communicated to the computing device (e.g. 511 of FIG. 5), as per block 2808. The information may be communicated by either the second sensor unit 1205 or the reference sensor unit 1211. Other example reference locations include, but are not limited to, ASIS points 1203, AIIS points 1217, and points along the iliac crest 1206, or the point of attachment of the ligamentum teres.

At blocks 2810 and 2812, and 2814 and 2816, respectively, similar steps are performed to the steps at blocks 2806 and 2808, except now for the second and third reference locations. For example, a stylus 1201 having the second sensor unit 1205 attached thereto may be used to contact second and third reference locations, respectively. When the stylus is in contact with the second reference location, the second sensor unit is in a second sensor location having a second pre-determined relationship to the second reference location. Similarly, when the stylus is in contact with the third reference location, the second sensor unit is in a third sensor location having a third pre-determined relationship to the third reference location.

When the second sensor unit is in the second and third sensor location, respectively, second and third information, respectively, relating to the relative positioning of the second sensor unit (and therefore to the second and third reference locations, respectively) with respect to the reference sensor 1211 is communicated to the computing device (e.g. 511 of FIG. 5). Once again, the second and third information may be communicated by either the second sensor unit 1205 or the reference sensor unit 1211. Further examples of second and third reference locations include, but are not limited to, ASIS points 1203, AIIS points 1217, and points along the iliac crest 1206. It may be desirable to use more than three reference locations to improve registration accuracy. One constraint on the selection of the reference locations is that they be separate non-collinear reference locations and that they be landmarks identifiable for the purpose of pre-determining the geometry of the bone.

At block 2818*a*, the computing device (e.g. 511 of FIG. 5) correlates the first second and third information and the first, second, and third pre-determined relationships with the pre-determined geometry stored within the computing device. The correlation allows the relative position of the bone with respect to other rigid bodies (possessing the required sensors and markers, apparent to those skilled in the art) to be determined and monitored using the first sensor unit 1211 and the second sensor unit on the rigid body.

Specific reference is now made to FIGS. 28B and 11. Method 2800b is preferably performed for the same purpose as method 2800a—to determine a relative position of a bone with respect to a reference sensor unit operatively connected to the bone. However, method 2800b differs from method 2800a in that a registration device (e.g. pelvis registration device 1100 and 2000) is used to position the second sensor unit in a known relationship to at least a first, second, and third reference location simultaneously.

At block 2802b, a pre-determined geometry of the bone (e.g. pelvis 1204) is input into a computing device (e.g. 511 of FIG. 5). The geometry may be measured based on a pre-operative scan of the patient and may be input using an input device, such as a keyboard or mouse, in communication with the computing device (e.g. 511 of FIG. 5). Where a pre-operative scan of the patient (or other suitable data from which the geometry of the bone may be measured) is unavailable, a default bone template (e.g. pelvis template) may be used.

At block 2804b, a reference sensor unit (e.g. 1211 of FIG. 12) is operatively connected to the bone 1104, for example, as described above. This connection may be achieved, for example, by fixing a pin or bone screw (e.g. 1210 of FIG. 12) to the bone 1104 and attaching the reference sensor unit (e.g. 1211 of FIG. 12) to the pin or bone screw (e.g. 1210 of FIG. 12) in a known orientation.

At block 2805, a second sensor unit is positioned in a sensor unit location. When in the sensor unit location, the second sensor unit has a first, second, and third pre-determined relationship to a first, second, and third reference location, respectively, on the bone 1104. In the exemplary embodiment illustrated in FIG. 11, the first reference location is the ASIS point 1103 shown in contact with first contact member 1117; the second reference location is the ASIS point 1103 in contact with second contact member 1106; and, the third reference point 1115 is a point along the iliac crest 1105. Reference locations may include, but are not limited to, ASIS points 1103, AIIS points (e.g. 1217 of FIG. 12), palpable points along the iliac crest 1105, and pubic tubercles 1113 (only one of which is shown).

To properly position the second sensor unit, the first, second, and third contact members 1117, 1106, 1110, respectively, are brought into contact with the first, second, and third reference locations, 1103, 1103, 1115, respectively on the bone 1104 via first, second, and third, contact points 1107, 1109, 1111, respectively on the registration device 1100.

With the second sensor unit 1130 properly positioned, information is communicated to the computing device (e.g. 511 of FIG. 5), as per block 2807. Similarly to the method 2800a of FIG. 28A, the information relates to the relative positioning of the second sensor with respect to the reference sensor unit (e.g. 1211 of FIG. 12). Once again, the information may be communicated by either the second sensor unit 1130 or the reference sensor unit (e.g. 1211 of FIG. 12).

By virtue of the known positional relationship between the second sensor unit 1130 and each of the three contact points 1107, 1109, 1111, the relative position of the bone 1104 with respect to the reference sensor unit (e.g. 1211 of FIG. 12) can be calculated from the information communicated between the second sensor unit 1130 and/or the reference sensor unit (e.g. 1211 of FIG. 12) and the computing device (e.g. 511 of FIG. 5).

At block 2818b, the first, second, and third pre-determined relationships between the sensor location and the first, second, and third reference locations, respectively, are input into the computing device (e.g. 511 of FIG. 5). At block 2820b, like at block 2820a, the computing device (e.g. 511 of FIG. 5) correlates the first second and third information with the pre-determined geometry stored within the computing device. The correlation allows the position of the bone 1104 to be determined with respect to the reference sensor unit (e.g. 1211 of FIG. 12).

Figure 29:
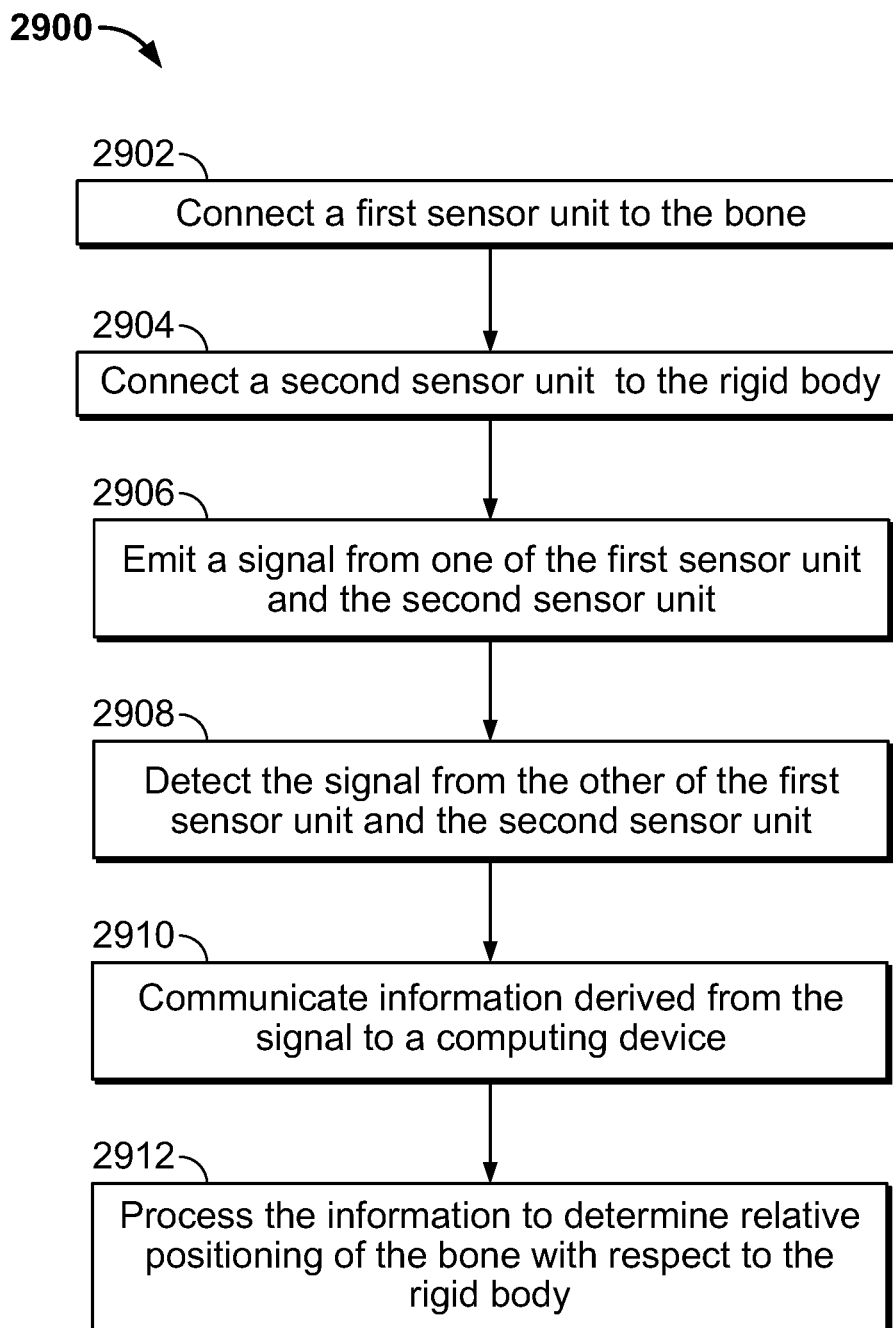

A method 2900 for determining the relative positioning of a bone with respect to a rigid body is now discussed with reference to FIG. 29. Reference will also be made to FIG. 13, in which an exemplary embodiment is illustrated wherein the bone is a pelvis 1304 of a patient 1307, and the rigid body is the femur 1306 of the patient. At block 2902, a first (or reference or pelvis) sensor unit 1311 is operatively connected to a bone (pelvis 1304), for example, as described above. The operative connection may be achieved via pin or bone screw 1310a, according to technique known to those ordinarily skilled in the art.

At block 2904, a second sensor unit (femur sensor unit 1305) is operatively connected to the rigid body (femur 1306). The operative connection may be achieved in the same manner described for the operative connection of first (or reference or pelvis) sensor unit 1311 to pelvis 1304.

At block 2906, a signal is emitted by one of (or both) the first and second sensor units, and at block 2908, the signal is detecting by the other of (or both) the first and second sensor units. The signal may, for example, be an IR signal emitted by IR emitters (see e.g. emitters 705, 715, and 725 in FIGS. 7A, 7B, and 7C) within the sensor unit. In such an embodiment, the detecting sensor (whether it be the first or second sensor unit or both) is adapted to detect IR signals.

The combination of the first and second sensor units may be selected according to the information that is desired. For example, where 6-DOF relative positioning is required, a combination of at least one optical sensor and at least three markers or emitters (preferably in a known positional relationship with one another) visible to the optical sensor may suffice, though additional optical sensors may be beneficial for field of view and accuracy.

Measurements from inertial sensors (i.e. accelerometers and gyroscopes) may be used to infer positioning information. However, determining positioning (whether angular or translational) from inertial measurements typically relies on integrating a signal, which, in the presence of noise, will result in drift in the inferred position. The drift increases as a function of time. It will be appreciated by those skilled in the art that the first and second sensor units may incorporate inertial sensors to improve the accuracy of the positioning calculated and displayed by the computing device. Furthermore, incorporating inertial sensors into the first and second sensor units may allow the line of sight between the at least one optical sensor (on the first and/or second sensor units) and the emitter(s) or marker(s) to be temporarily broken, during which time the relative positioning of the first and second sensor units may be inferred from inertial measurements.

At block, 2910, information derived from the signal (or signals) and possibly other sensed information (e.g. accelerometer measurements, gyroscope measurements, etc.) is communicated to a computing device (e.g. 511 of FIG. 5). The information derived from the signal (or signals) relates to the positional relationship between the optical sensors and the markers or emitters.

At block 2912, the information is processed to determine the relative positioning between the bone 1304 and the rigid body 1306. Optionally, the processed information may be displayed in a display (e.g. 514 of FIG. 5), for example, for a surgeon.

IV. Computer Implementation

In one embodiment, communication and/or data transmission between the various components of the present invention is accomplished over a network consisting of electronic devices connected either physically or wirelessly. Such devices (e.g., end-user devices and/or servers) may include, but are not limited to: a desktop computer, a laptop computer, a handheld device or PDA, a cellular telephone, a set top box, an Internet appliance, an Internet TV system, a mobile device or tablet, or systems equivalent thereto. Exemplary networks include a Local Area Network, a Wide Area Network, an organizational intranet, the Internet, or networks equivalent thereto. The functionality and system components of an exemplary computer and network are further explained in conjunction with FIG. 30.

Figure 30:
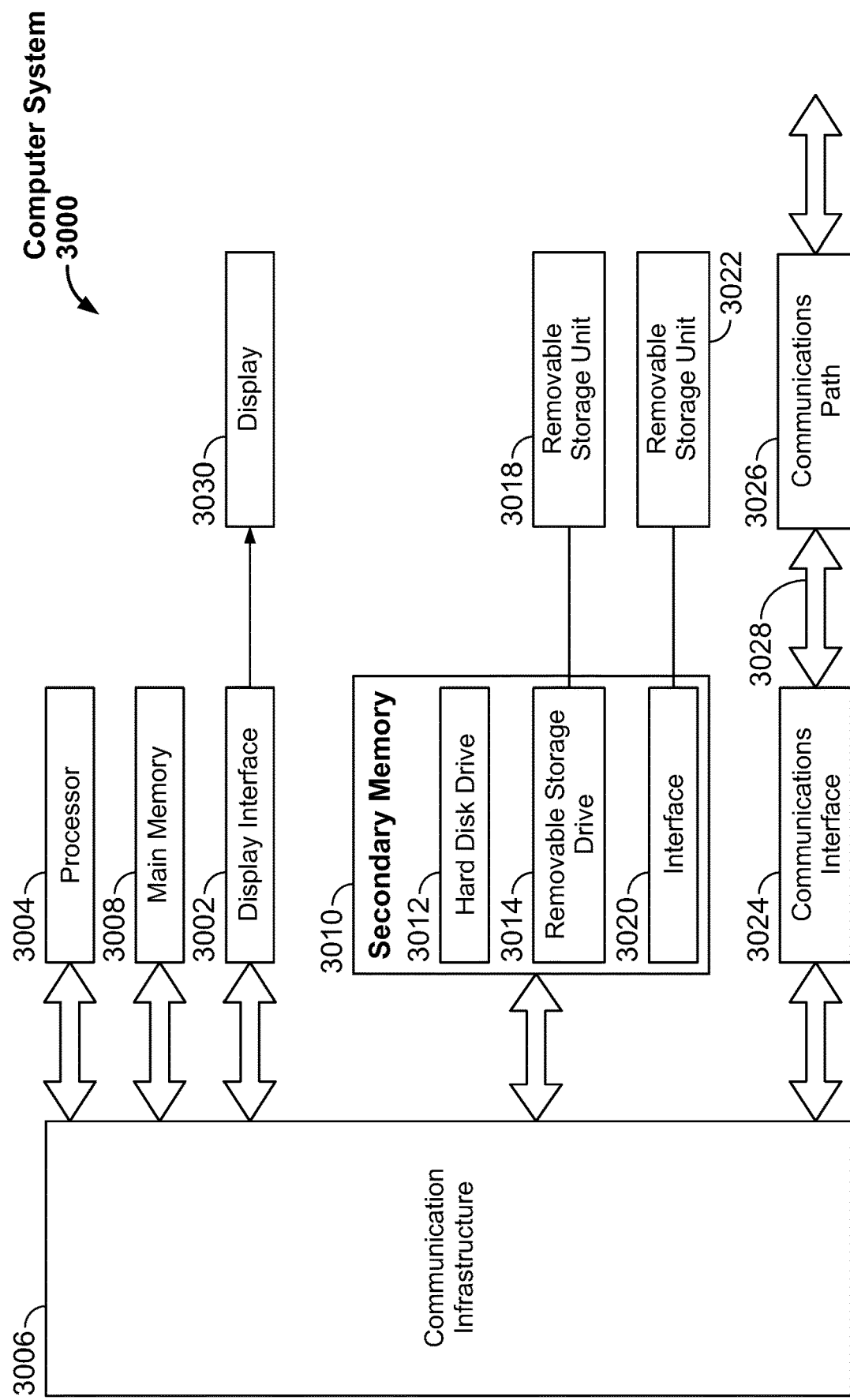
FIG. 30 is a schematic drawing of a computer system used to implement the systems and methods presented It will be appreciated that for simplicity and clarity of illustration, elements shown in the figures have not necessarily been drawn to scale. For example, the dimensions of some of the elements may be exaggerated relative to other elements for clarity. Further, where considered appropriate, similar reference numerals may be used among the figures to indicate corresponding or analogous elements (e.g. reference sensor 811 of FIG. 8 is analogous to reference sensor 1211 of FIG. 12).

In one embodiment, for example, the invention is directed toward one or more computer systems capable of carrying out the functionality described herein. For example, FIG. 30 is a schematic drawing of a computer system 3000 used to implement the methods presented above. Computer system 3000 includes one or more processors, such as processor 3004. The processor 3004 is connected to a communication infrastructure 3006 (e.g., a communications bus, cross-over bar, or network). Computer system 3000 can include a display interface 3002 that forwards graphics, text, and other data from the communication infrastructure 3006 (or from a frame buffer not shown) for display on a local or remote display unit 3030.

Computer system 3000 also includes a main memory 3008, such as random access memory (RAM), and may also include a secondary memory 3010. The secondary memory 3010 may include, for example, a hard disk drive 3012 and/or a removable storage drive 3014, representing a floppy disk drive, a magnetic tape drive, an optical disk drive, flash memory device, etc. The removable storage drive 3014 reads from and/or writes to a removable storage unit 3018. Removable storage unit 3018 represents a floppy disk, magnetic tape, optical disk, flash memory device, etc., which is read by and written to by removable storage drive 3014. As will be appreciated, the removable storage unit 3018 includes a computer usable storage medium having stored therein computer software, instructions, and/or data.

In alternative embodiments, secondary memory 3010 may include other similar devices for allowing computer programs or other instructions to be loaded into computer system 3000. Such devices may include, for example, a removable storage unit 3022 and an interface 3020. Examples of such may include a program cartridge and cartridge interface (such as that found in video game devices), a removable memory chip (such as an erasable programmable read only memory (EPROM), or programmable read only memory (PROM)) and associated socket, and other removable storage units 3022 and interfaces 3020, which allow computer software, instructions, and/or data to be transferred from the removable storage unit 3022 to computer system 3000.

Computer system 3000 may also include a communications interface 3024. Communications interface 3024 allows computer software, instructions, and/or data to be transferred between computer system 3000 and external devices. Examples of communications interface 3024 may include a modem, a network interface (such as an Ethernet card), a communications port, a Personal Computer Memory Card International Association (PCMCIA) slot and card, etc. Software and data transferred via communications interface 3024 are in the form of signals 3028 which may be electronic, electromagnetic, optical or other signals capable of being received by communications interface 3024. These signals 3028 are provided to communications interface 3024 via a communications path (e.g., channel) 3026. This channel 3026 carries signals 3028 and may be implemented using wire or cable, fiber optics, a telephone line, a cellular link, a radio frequency (RF) link, a wireless communication link, and other communications channels.

In this document, the terms "computer-readable storage medium," "computer program medium," and "computer usable medium" are used to generally refer to media such as removable storage drive 3014, removable storage units 3018, 3022, data transmitted via communications interface 3024, and/or a hard disk installed in hard disk drive 3012. These computer program products provide computer software, instructions, and/or data to computer system 3000. These computer program products also serve to transform a general purpose computer into a special purpose computer programmed to perform particular functions, pursuant to instructions from the computer program products/software. Embodiments of the present invention are directed to such computer program products.

Computer programs (also referred to as computer control logic) are stored in main memory 3008 and/or secondary memory 3010. Computer programs may also be received via communications interface 3024. Such computer programs, when executed, enable the computer system 3000 to perform the features of the present invention, as discussed herein. In particular, the computer programs, when executed, enable the processor 3004 to perform the features of the presented methods. Accordingly, such computer programs represent controllers of the computer system 3000. Where appropriate, the processor 3004, associated components, and equivalent systems and sub-systems thus serve as "means for" performing selected operations and functions. Such "means for" performing selected operations and functions also serve to transform a general purpose computer into a special purpose computer programmed to perform said selected operations and functions.

In an embodiment where the invention is implemented using software, the software may be stored in a computer program product and loaded into computer system 3000 using removable storage drive 3014, interface 3020, hard drive 3012, communications interface 3024, or equivalents thereof. The control logic (software), when executed by the processor 3004, causes the processor 3004 to perform the functions and methods described herein.

In another embodiment, the methods are implemented primarily in hardware using, for example, hardware components such as application specific integrated circuits (ASICs). Implementation of the hardware state machine so as to perform the functions and methods described herein will be apparent to persons skilled in the relevant art(s). In yet another embodiment, the methods are implemented using a combination of both hardware and software.

Embodiments of the invention, including any systems and methods described herein, may also be implemented as instructions stored on a machine-readable medium, which may be read and executed by one or more processors. A machine-readable medium may include any mechanism for storing or transmitting information in a form readable by a machine (e.g., a computing device). For example, a machine-readable medium may include read only memory (ROM); random access memory (RAM); magnetic disk storage media; optical storage media; flash memory devices;

electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact result from computing devices, processors, controllers, or other devices executing firmware, software, routines, instructions, etc.

V. Additional Embodiments

In one embodiment, there is provided a system for performing a hip replacement surgery, comprising: (1) a pelvis sensor unit configured to be coupled to a patient's pelvis; (2) a registration sensor unit; (3) an insertion tool sensor unit configured to be coupled to an acetabular insertion tool; and (4) a femur sensor unit configured to be coupled to the patient's femur. The system further comprises a computer-readable storage medium having instructions executable by at least one processing device that, when executed, cause the processing device to: (a) calculate a positional relationship between the pelvis sensor unit and the patient's pelvis based on a registration measurement between the pelvis sensor unit and the registration sensor unit, wherein the registration measurement is based on at least three reference points; (b) measure an initial positional relationship between the pelvis sensor unit and the femur sensor unit (i.e., while the native hip joint is still intact), (c) track an orientation of the acetabular insertion tool during an implantation procedure based on a positional relationship between the pelvis sensor unit and the insertion tool sensor unit, (d) calculate angles of abduction and anteversion based on the orientation of the acetabular insertion tool with respect to the pelvis, (e) provide a real-time display conveying the angles of abduction and anteversion during the implantation procedure, (f) measure a post-reduction positional relationship between the pelvis sensor unit and the femur sensor unit (i.e. during a trial or final reduction using prosthetic components), (g) calculate a change in leg position based on the initial positional relationship (between the femur sensor and the pelvis sensor), the post-reduction positional relationship (between the femur sensor and the pelvis sensor), and the positional relationship between the pelvis sensor unit and the patient's pelvis, and (h) provide a display of the change in leg position. The initial positional relationship may include an initial leg translational measurement. The initial positional relationship may include an initial leg orientation measurement. The change in leg position may be calculated based on a comparison between the initial positional relationship and the post-reduction positional relationship. The change in leg position may also be calculated based on a femur articulation measurement between the pelvis sensor unit and the femur sensor unit. The change in leg position may also include a leg length measurement, an offset measurement, and/or an anterior-posterior position measurement.

The computer-readable storage medium may further include instructions executable by at least one processing device that, when executed, cause the processing device to: (i) track a femur orientation during a leg positioning procedure based on a positional relationship between the pelvis sensor unit and the femur sensor unit; (j) provide a real-time display conveying the femur orientation during the leg positioning procedure; and/or (k) calculate a center-of-rotation of the patient's femur. The center-of-rotation may be calculated based on an acetabulum surface measurement between the pelvis sensor unit and the registration sensor unit. The center-of-rotation may be calculated based on a femur articulation measurement between the pelvis sensor unit and the femur sensor unit.

In another embodiment, there is provided a system for performing a hip replacement surgery, including (1) a pelvis sensor unit configured to be coupled to a patient's pelvis; (2) a reference sensor unit; and (3) a computer-readable storage medium having instructions executable by at least one processing device that, when executed, cause the processing device to: (a) calculate a positional relationship between the pelvis sensor unit and the patient's pelvis based on a registration measurement between the pelvis sensor unit and the reference sensor unit, wherein the registration measurement includes at least three reference points; (b) track an orientation of an acetabular insertion tool during an implantation procedure based on a positional relationship between the pelvis sensor unit and the reference sensor unit, wherein the reference sensor unit is coupled to the acetabular insertion tool during the implantation procedure, (c) calculate implant parameters based on the orientation of the acetabular insertion tool (implant parameters being, for example, cup position, change in cup position, cup orientation, or any other information based on the positional relationship), and (d) provide a real-time display of the implant parameters during the implantation procedure.

The computer-readable storage medium may further include instructions executable by at least one processing device that, when executed, cause the processing device to: (e) calculate an initial leg position based on a initial positional relationship measurement between the pelvis sensor unit and the reference sensor unit, wherein the reference sensor unit is coupled to the patient's femur, (f) measure a post-reduction leg position based on a post-reduction positional relationship between the pelvis sensor unit and the reference sensor unit, (g) calculate a change in leg position between the initial leg position and the post-reduction leg position, (h) provide a display of the change in leg position; (i) calculate a center-of-rotation of the patient's femur; (j) track a femur orientation during a leg positioning procedure based on a positional relationship between the pelvis sensor unit and the reference sensor unit when the reference sensor unit is coupled to the patient's femur; and/or (k) provide a real-time display conveying the femur orientation during the leg positioning procedure.

The initial leg position may be calculated based, in part, on an initial leg length measurement. The initial leg position may be calculated based, in part, on an initial leg orientation measurement. The initial leg position may be calculated based, in part, on a positional relationship between the pelvis sensor unit and the reference sensor unit when the reference sensor unit is coupled to the patient's femur. In an alternative embodiment, the change in leg position may be calculated based on a femur articulation measurement between the pelvis sensor unit and the reference sensor unit, wherein the reference sensor unit is coupled to the patient's femur during the femur articulation measurement. The change in leg position may include a leg length measurement, an offset measurement, and/or an anterior-posterior position measurement.

The center-of-rotation may be calculated based on an acetabulum surface measurement between the pelvis sensor unit and the reference sensor unit, wherein the reference sensor unit is brought in contact with three or more points along the acetabulum surface. The center-of-rotation may also be calculated based on a femur articulation measurement between the pelvis sensor unit and the reference sensor unit, wherein the reference sensor unit is coupled to the patient's femur during the femur articulation measurement.

In still another embodiment, there is provided a system for performing a hip replacement surgery, including (1) a pelvis sensor unit configured to be coupled to a patient's pelvis; (2) a reference sensor unit; and (3) a computer-readable storage medium having instructions executable by at least one processing device that, when executed, cause the processing device to: (a) calculate a positional relationship between the pelvis sensor unit and the patient's pelvis based on a registration measurement between the pelvis sensor unit and a reference sensor unit, wherein the registration measurement includes at least three reference points; (b) calculate an initial leg position based on a initial positional relationship measurement between the pelvis sensor unit and the reference sensor unit when the reference sensor unit is coupled to the patient's femur, (c) track a femur orientation during a leg positioning procedure based on a positional relationship between the pelvis sensor unit and the reference sensor unit, (d) provide a real-time display conveying the femur orientation during the leg positioning procedure, (e) measure a post-reduction leg position based on a positional relationship between the pelvis sensor unit and the reference sensor unit, (f) calculate a change in leg position between the initial leg position and the post-reduction leg position, and (g) provide a display of the change in leg position.

The computer-readable storage medium may further include instructions executable by at least one processing device that, when executed, cause the processing device to calculate a center-of-rotation of the patient's femur. The center-of-rotation may be calculated based on an acetabulum surface measurement between the pelvis sensor unit and the reference sensor unit, wherein the reference sensor unit is brought in contact with three or more points along the acetabulum surface. The center-of-rotation may calculated based on a femur articulation measurement between the pelvis sensor unit and the reference sensor unit, wherein the reference sensor unit is coupled to the patient's femur during the femur articulation measurement.

The change in leg position may be calculated based on a femur articulation measurement between the pelvis sensor unit and the reference sensor unit, wherein the reference sensor unit is coupled to the patient's femur during the femur articulation measurement. The change in leg position includes a leg length measurement, an offset measurement, and/or an anterior-posterior position measurement.

In still another embodiment, there is provided a computer-readable storage medium, for performing hip replacement surgery, having instructions executable by at least one processing device that, when executed, cause the processing device to: (a) calculate a positional relationship between a pelvis sensor unit and a patient's pelvis, when the pelvis sensor unit is coupled to a first point on a patient's pelvis; (b) calculate an initial leg position based on a positional relationship between the pelvis sensor unit and a sensor unit coupled to the patient's femur; (c) track an orientation of an acetabular insertion tool during an implantation procedure based on a positional relationship between the pelvis sensor unit and a sensor unit coupled to the acetabular insertion tool; (d) calculate implant parameters based on the orientation of the acetabular insertion tool; (e) provide a real-time display conveying the implant parameters during the implantation procedure; (f) track an orientation of the patient's femur during a leg positioning procedure based on a positional relationship between the pelvis sensor unit and the sensor unit coupled to the patient's femur; (g) provide a real-time display conveying the orientation of the patient's femur during the leg positioning procedure; (h) measure a post-reduction leg position based on the positional relationship between the pelvis sensor unit and the sensor unit coupled to the patient's femur; (i) calculate a change in leg position between the initial leg position and the post-reduction leg position; and (j) provide a display of the change in leg position. The implant parameters include angles of abduction and anteversion. In alternative embodiments, the computer-readable storage medium performs only one or more of the above listed functions, or performs the above listed functions in varying orders, or in parallel or serial steps.

In another embodiment, there is provide a computer-readable storage medium, for performing hip replacement surgery, having instructions executable by at least one processing device that, when executed, cause the processing device to (a) calculate a positional relationship between a pelvis sensor unit and a patient's pelvis, when the pelvis sensor unit is coupled to a first point on a patient's pelvis; (b) calculate an initial leg position based on a positional relationship between the pelvis sensor unit and a sensor unit coupled to the patient's femur; (c) track an orientation of an acetabular insertion tool during an implantation procedure based on a positional relationship between the pelvis sensor unit and a sensor unit coupled to the acetabular insertion tool; (d) calculate implant parameters based on the orientation of the acetabular insertion tool; (e) provide a real-time display conveying the implant parameters during the implantation procedure; (f) track the patient's femur during a leg positioning procedure based on a positional relationship between the pelvis sensor unit and the sensor unit coupled to the patient's femur; (g) measure a post-reduction leg position based on the positional relationship between the pelvis sensor unit and the sensor unit coupled to the patient's femur; (h) calculate a change in leg position between the initial leg position and the post-reduction leg position; and (i) provide a display of the change in leg position. The implant parameters may include angles of abduction and anteversion. The computer-readable storage may further comprise instructions executable by at least one processing device that, when executed, cause the processing device to (j) track an orientation of the patient's femur during the leg positioning procedure based on a positional relationship between the pelvis sensor unit and the sensor unit coupled to the patient's femur; and (k) provide a real-time display conveying the orientation of the patient's femur during the leg positioning procedure.

CONCLUSION

The foregoing description of the invention has been presented for purposes of illustration and description. It is not intended to be exhaustive or to limit the invention to the precise form disclosed. Other modifications and variations may be possible in light of the above teachings. The embodiments were chosen and described in order to best explain the principles of the invention and its practical application, and to thereby enable others skilled in the art to best utilize the invention in various embodiments and various modifications as are suited to the particular use contemplated. It is intended that the appended claims be construed to include other alternative embodiments of the invention; including equivalent structures, components, methods, and means.

Accordingly, it is to be understood that this invention is not limited to particular embodiments described, and as such may vary. It is also to be understood that the terminology used herein is for the purpose of describing particular embodiments only, and is not intended to be limiting.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It is to be appreciated that the Detailed Description section, and not the Summary and Abstract sections, is intended to be used to interpret the claims. The Summary and Abstract sections may set forth one or more, but not all exemplary embodiments of the present invention as contemplated by the inventor(s), and thus, are not intended to limit the present invention and the appended claims in any way.

What is claimed is:

1. A system comprising:
   an optical sensor unit comprising an optical sensor, and at least one human interface sensor configured to receive user input, wherein: the optical sensor is configured to detect light within a field of view, the field of view for aligning with a site of a procedure; and the optical sensor unit is configured to generate and communicate sensor information derived from the light received by the optical sensor;
   a bone sensor unit configured to attach to a bone for determining a first position, the first position associated with the bone, the bone sensor unit comprising at least one first light reflector configured to provide to the optical sensor unit a reflected light used to determine the first position in six degrees of freedom;
   a stylus sensor unit configured to attach to a stylus for determining a second position, the second position associated with the stylus, the stylus sensor unit comprising at least one second light reflector configured to provide to the optical sensor unit a reflected light used to determine the second position in six degrees of freedom;
   a tool sensor unit configured to attach to a surgical tool for determining a third position, the third position associated with the surgical tool, the tool sensor unit comprising at least one third light reflector configured to provide to the optical sensor unit a reflected light used to determine the third position in six degrees of freedom;
   a non-transitory computer readable storage device storing instructions, which when executed by a processor, cause the processor to perform steps comprising:
      receiving from the optical sensor unit an input for invoking a registration of the bone sensor unit to the bone;
      performing the registration to register a relative position of the bone sensor unit to the bone in response to receiving the input and first sensor information indicating references for the bone, the first sensor information derived from the reflected light of the bone sensor unit and the stylus sensor unit;
      determining a relative position of the bone and the surgical tool in six degrees of freedom in accordance with the registration and second sensor information, the second sensor information derived from the reflected light of the bone sensor unit and the tool sensor unit;
      determining display information in accordance with the relative position of the bone and the surgical tool; and
      providing the display information for presenting by a display unit.

2. The system of claim 1, wherein the bone is one of a pelvis and a femur.

3. The system of claim 1, wherein the surgical tool comprises one of a tool for joint replacement surgery, a tool for joint resurfacing surgery or a tool for joint revision surgery.

4. The system of claim 1, wherein the bone comprises a pelvis and wherein the references for the bone comprise references for the pelvis for performing the registration.

5. The system of claim 4, wherein the surgical tool comprises an acetabular insertion tool, and the relative position of the bone and the surgical tool comprises a relative position of the pelvis and the acetabular insertion tool.

6. The system of claim 1, wherein:
   the instructions configure the processor to access a pre-determined geometry for the bone, the pre-determined geometry derived from an X-ray, a computed tomography (CT) scan or a magnetic resonance imaging (MRI) scan of the bone; and
   the step of performing the registration registers the bone sensor unit and the pre-determined geometry in a known relationship using the references for the bone.

7. The system of claim 1, wherein any one or more of the at least one first light reflector, the at least one second light reflector or the at least one third light reflector comprises at least one reflective marker.

8. The system of claim 1, wherein the optical sensor comprises a stereoscopic camera.

9. The system of claim 1, wherein the optical sensor unit comprises a handheld sensor unit.

10. The system of claim 1 comprising one or both of the processor and the display unit.

11. The system of claim 1, wherein the optical sensor unit comprises the display unit.

12. The system of claim 11, wherein the optical sensor unit comprises a housing for the optical sensor and a handle shaft extending from the housing.

13. The system of claim 1, wherein the stylus sensor unit and the tool sensor unit comprise a same sensor unit.

14. A method comprising:
   using a human interface sensor of an optical sensor unit comprising an optical sensor to invoke a processor to perform a registration of a bone sensor unit to a bone from bone references indicated by a stylus coupled to a stylus sensor unit, wherein: the bone sensor unit is coupled to the bone for determining a first position, the first position associated with the bone, and the bone sensor unit comprises at least one first light reflector configured to provide to the optical sensor unit a reflected light used to determine the first position in six degrees of freedom; the optical sensor is configured to detect light within a field of view, the field of view for aligning with a site of a procedure; the optical sensor unit is configured to generate and communicate sensor information derived from the light received by the optical sensor; and the stylus sensor unit is coupled to the stylus for determining a second position, the second position associated with the stylus and the stylus sensor unit comprises at least one second light reflector to provide to the optical sensor unit a reflected light used to determine the second position in six degrees of freedom;

using the optical sensor unit to generate and communicate to the processor first sensor information derived from the reflected light from each of the bone sensor unit and the stylus sensor unit, the stylus sensor unit indicating the bone references and the first sensor information for determining a relative position of the bone and the stylus to perform the registration;

using the optical sensor unit to generate and communicate to the processor second sensor information derived from reflected light from each of the bone sensor unit and a tool sensor unit to receive display information associated with a relative position of the bone and a surgical tool, wherein: the tool sensor unit is coupled to the surgical tool for determining a third position, the third position associated with the surgical tool, and the tool sensor unit comprises at least one third light reflector configured to provide to the optical sensor unit a reflected light used to determine the third position in six degrees of freedom; and the processor is configured to: determine the relative position of the bone and the surgical tool using the registration and the second sensor information, determine the display information, and provide the display information to a display unit; and receiving the display information via the display unit.

15. The method of claim 14, wherein the optical sensor unit comprises the display unit for receiving the display information.

16. The method of claim 14, comprising holding the optical sensor unit by hand to use the optical sensor to generate and communicate either or both of the first sensor information and the second sensor information.

17. The method of claim 14 comprising any one or more of: coupling the bone sensor unit to the bone; coupling the stylus sensor unit to the stylus; and coupling the tool sensor unit to the surgical tool.

18. The method of claim 14, wherein the bone is one of a pelvis and a femur.

19. The method of claim 14, wherein the surgical tool is one of a tool for joint replacement surgery, a tool for joint resurfacing surgery and a tool for joint revision surgery.

20. The method of claim 14, wherein the bone comprises a pelvis and wherein the first sensor information is received for determining the bone references for the pelvis to perform the registration.

21. The method of claim 20, wherein the surgical tool comprises an acetabular insertion tool, and the display information is associated with a relative position of the pelvis and the acetabular insertion tool.

22. The method of claim 14 comprising providing the processor with a pre-determined geometry for the bone, the pre-determined geometry derived from an X-ray, a computed tomography (CT) scan or a magnetic resonance imaging (MRI) scan of the bone; and wherein the registration registers the bone sensor unit and the pre-determined geometry in a known relationship using the bone references.

23. The method of claim 14, wherein the optical sensor comprises a stereoscopic camera.

24. The method of claim 14, wherein the stylus sensor unit and the tool sensor unit comprise a same sensor unit.

25. A non-transitory computer readable storage device storing instructions, which when executed by a processor, cause the processor to perform steps comprising:

receiving input from at least one human interface sensor of an optical sensor unit for invoking the processor to perform a registration of a bone sensor unit to a bone, wherein: the optical sensor unit comprises an optical sensor configured to detect light within a field of view, the field of view for aligning with a site of a procedure; and the optical sensor unit is configured to generate and communicate sensor information derived from the light received by the optical sensor;

performing a registration to register a relative position of the bone sensor unit to the bone using first sensor information received from the optical sensor unit to perform the registration, the first sensor information indicating references for the bone, the first sensor information derived from reflected light from each of the bone sensor unit and a stylus sensor unit, and wherein: the bone sensor unit is coupled to the bone for determining a first position, the first position associated with the bone, and the bone sensor unit comprises at least one first light reflector configured to provide to the optical sensor unit a reflected light used to determine the first position in six degrees of freedom; and the stylus sensor unit is coupled to a stylus for identifying the references for the bone, the stylus sensor unit is coupled to the stylus for determining a second position, the second position associated with the stylus and the stylus sensor unit comprising at least one second light reflector to provide to the optical sensor unit a reflected light used to determine second position in six degrees of freedom;

determining a relative position of the bone and a surgical tool in six degrees of freedom in accordance with the registration and second sensor information, the second sensor information derived from reflected light of the bone sensor unit and a tool sensor unit, wherein the tool sensor unit is coupled to the surgical tool for determining a third position, the third position associated with the surgical tool, and the tool sensor unit comprises at least one third light reflector to provide to the optical sensor unit a reflected light used to determine the third position in six degrees of freedom;

determining display information in accordance with the relative position of the bone and the surgical tool; and providing the display information for presenting by a display unit.

26. The non-transitory computer readable storage device of claim 25, wherein the steps comprise accessing a pre-determined geometry for the bone, the pre-determined geometry derived from an X-ray, a computed tomography (CT) scan or a magnetic resonance imaging (MRI) scan of the bone; and wherein performing the registration registers the bone sensor unit and the pre-determined geometry in a known relationship using the references for the bone.

27. The non-transitory computer readable storage device of claim 25, wherein any one or more of: the optical sensor comprises a stereoscopic camera; the optical sensor unit comprises a handheld sensor unit; the optical sensor unit comprises the display unit; the optical sensor unit comprises a housing for the optical sensor and a handle shaft extending from the housing; the stylus sensor unit and the tool sensor unit comprise a same sensor unit; the bone comprises one of a pelvis and a femur; and the surgical tool is one of a tool for joint replacement surgery, a tool for joint resurfacing surgery and a tool for joint revision surgery.

28. A computer-implemented method comprising executing by a processor steps comprising:
- receiving input from at least one human interface sensor of an optical sensor unit for invoking the processor to perform a registration of a bone sensor unit to a bone, wherein: the optical sensor unit comprises an optical sensor configured to detect light within a field of view, the field of view for aligning with a site of a procedure; and the optical sensor unit is configured to generate and communicate sensor information derived from the light received by the optical sensor;
- performing a registration to register a relative position of the bone sensor unit to the bone using first sensor information received from the optical sensor unit, the first sensor information indicating references for the bone, the first sensor information derived from reflected light from each of the bone sensor unit and a stylus sensor unit, and wherein: the bone sensor unit is coupled to the bone for determining a first position, the first position associated with the bone, and the bone sensor unit comprises at least one first light reflector configured to provide to the optical sensor unit a reflected light used to determine the first position in six degrees of freedom; and the stylus sensor unit is coupled to a stylus for identifying the references for the bone, the stylus sensor unit is coupled to the stylus for determining a second position, the second position associated with the stylus and the stylus sensor unit comprising at least one second light reflector to provide to the optical sensor unit a reflected light used to determine the second position in six degrees of freedom;
- determining a relative position of the bone and a surgical tool in six degrees of freedom in accordance with second sensor information, the second sensor information derived from reflected light of the bone sensor unit and a tool sensor unit, wherein the tool sensor unit is coupled to the surgical tool for determining a third position, the third position associated with the surgical tool, and the tool sensor unit comprises at least one light third reflector to provide to the optical sensor unit a reflected light used to determine the third position in six degrees of freedom;
- determining display information in accordance with the relative position of the bone and the surgical tool; and
- providing the display information for presenting by a display unit.

29. The computer implemented method of claim 28, wherein the steps comprise accessing a pre-determined geometry for the bone, the pre-determined geometry derived from an X-ray, a computed tomography (CT) scan or a magnetic resonance imaging (MRI) scan of the bone; and wherein performing the registration registers the bone sensor unit and the pre-determined geometry in a known relationship using the references for the bone.

30. The computer implemented method of claim 28, wherein any one or more of: the optical sensor comprises a stereoscopic camera; the optical sensor unit comprises a handheld sensor unit; the optical sensor unit comprises the display unit; the optical sensor unit comprises a housing for the optical sensor and a handle shaft extending from the housing; the stylus sensor unit and the tool sensor unit comprise a same sensor unit; the bone comprises one of a pelvis and a femur; and the surgical tool is one of a tool for joint replacement surgery, a tool for joint resurfacing surgery and a tool for joint revision surgery.

* * * * *